United States Patent [19]

Sasse et al.

[11] Patent Number: 4,871,387
[45] Date of Patent: Oct. 3, 1989

[54] PYRI(MI)DYL-OXY-AND -THIO-BENZOIC ACID DERIVATIVES USEFUL AS HERBICIDES AND PLANT GROWTH REGULANTS

[75] Inventors: Klaus Sasse, Bergisch Gladbach; Reiner Fischer, Monheim; Hermann Hagemann; Hans-Joachim Santel, both of Leverkusen; Robert R. Schmidt; Kalus Lürssen, both of Bergisch Gladbach, all of Fed. Rep. of Germany

[73] Assignee: Bayer Aktiengesellschaft, Leverkusen, Fed. Rep. of Germany

[21] Appl. No.: 938,203

[22] Filed: Dec. 4, 1986

[30] Foreign Application Priority Data

Dec. 5, 1985 [DE] Fed. Rep. of Germany ....... 3543037
Jan. 24, 1986 [DE] Fed. Rep. of Germany ....... 3602016

[51] Int. Cl.[4] .................. A01N 43/40; C07D 417/00; C07D 221/02; C07D 239/02
[52] U.S. Cl. ........................................ 71/92; 71/94;
540/544; 540/545; 540/553; 540/554; 540/575;
540/600; 540/601; 544/60; 544/61; 544/114;
544/116; 544/302; 544/311; 544/312; 544/313;
544/314; 544/316; 544/317; 544/318; 546/112;
546/141; 546/142; 546/143; 546/145; 546/146;
546/147; 546/153; 546/155; 546/157; 546/291;
546/293; 546/296; 546/297; 546/300; 546/301;
546/302
[58] Field of Search ............... 544/316, 302, 311, 312,
544/313, 314, 316, 317, 318, 114, 116, 60, 61;
540/545, 544, 553, 554, 575, 600, 601; 71/92

[56] References Cited
U.S. PATENT DOCUMENTS 4,427,437 1/1984 Serban et al. ....................... 544/311

FOREIGN PATENT DOCUMENTS 0001187 3/1979 European Pat. Off. ............ 544/312

OTHER PUBLICATIONS

Chemistry of Plant Protecting Agents and Pesticides vol. 2, pp. 289-295; vol. 5, pp. 209-217, Springer-Verlag, Berlin 1970/1977.
Chemistry of Plant Protecting Agents and Pesticides vol. 2, pp. 353-354 and vol. 5, p. 318, Springer-Verlag, Berlin 1970/1977, GDR Patent No. 109, 170.

*Primary Examiner*—Mary C. Lee
*Assistant Examiner*—J. Richter
*Attorney, Agent, or Firm*—Sprung Horn Kramer & Woods

[57] ABSTRACT

New pyri(mi)dyl-oxy- or -thio-benzoic acid derivatives of the formula

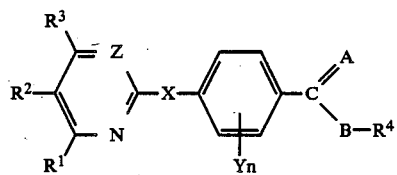

are taught which have herbicidal and plant growth regulating activity. In the formula Z can be Ch or N, X is oxygen or sulphur, A is oxygen, sulphur, a radical $R^5$—N= or a radical $R^6O$—N= and B is oxygen, sulphur, a radical $$-\underset{|}{N}-R^7 \text{ or } -\underset{|}{N}-OR^8$$

with the proviso that at least one of the radicals $R^1$, $R^2$ or $R^3$ represents alkyl or a part of a 3- to 6-membered fused carbocyclic ring.

9 Claims, No Drawings

PYRI(MI)DYL-OXY-AND -THIO-BENZOIC ACID DERIVATIVES USEFUL AS HERBICIDES AND PLANT GROWTH REGULANTS

The present invention relates to new pyri(mi)dyloxy- and -thio-benzoic acid derivatives, several processes for their preparation and their use as herbicides and growth regulators.

It is already known that certain benzoic acids and their derivatives have herbicidal properties (cf. R. Wegler, "Chemie der Pflanzenschutz- und Schadlingsbekampfungsmittel [Chemistry of Plant Protecting Agents and Pesticides]" vol. 2, pages 289–295; vol. 5, pages 209–217, Springer-Verlag, Berlin 1970/1977).

It is furthermore known that numerous pyridyl and pyrimidyl ethers and thioethers exhibit herbicidal action (cf. R. Wegler "Chemie der Pflanzenschutz- und Schadlingsbekampfungsmittel [Chemistry of Plant Protecting Agents and Pesticides]" Vol. 2, pages 353–354 and vol. 5, page 318, Springer-Verlag, Berlin 1970/1977, GDR Pat. No. 109,170). Herbicidally active benzoic acids and their pyri(mi)dyl-oxy- or -thio-substituted derivatives are also known (cf. European patent specification No. 147,477 and European patent specification No. 1,187).

The herbicidal activity of these previously-known compounds towards weeds is, however, not always satisfactory in all areas of application, as is their compatibility with important crops.

Nothing is known about the activity as growth regulator of these previously-known pyri(mi)dyl-oxy- or -thio-substituted benzoic acid derivatives.

New pyri(mi)dyl-oxy- or -thio-benzoic acid derivatives of the formula (I),

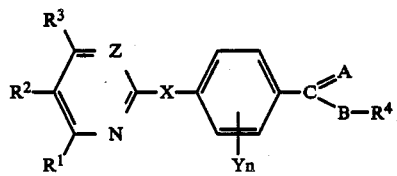

in which

R$^1$, R$^2$ and R$^3$, independently of one another, represent, in each case, hydrogen, halogen, alkyl, optionally substituted alkoxy, haloalkyl, alkenyl or optionally substituted amino or R$^1$ and R$^2$ or R$^2$ and R$^3$ together represent a fused 3- to 6-membered carbocyclic ring, with the proviso that at least one of the radicals R$^1$, R$^2$ or R$^3$ represents alkyl or a part of the 3- to 6-membered fused carbocyclic ring, Z represents a (CH) group or a nitrogen atom, X represents oxygen or sulphur, Y represents halogen, nitro, cyano, amino, alkylcarbonylamino, alkoxycarbonylamino, phenoxycarbonylalkylamino, alkyl, alkoxy or haloalkyl, where Y can be identical or different, n represents an integer from 0 to 4, A represents oxygen, sulphur, a radical R$^5$—N= or a radical R$^6$O—N=, where R$^5$ represents hydrogen, alkyl, hydroxyalkyl, alkenyl or in each case optionally substituted cycloalkyl, aryl or aralkyl, R$^6$ represents hydrogen, in each case optionally substituted alkyl or mono- or polyunsaturated alkenyl, B represents oxygen, sulphur, a radical

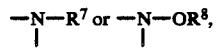

where

R$^7$ represents hydrogen, alkenyl or alkyl which is optionally substituted by halogen, cyano or a radical —D—R$^9$, where D represents oxygen, sulphur, sulphinyl or sulphonyl and R$^9$ represents hydrogen, alkyl, mono- or polyunsaturated alkenyl or in each case optionally substituted aryl or aralkyl, or —CO-alkyl, R$^8$ represents hydrogen, in each case optionally substituted alkyl or mono- or polyunsaturated alkenyl and R$^4$ represents optionally substituted saturated or unsaturated aliphatic radical, where selected substiuent are: halogen, nitro, cyano, a radical —D—R$^9$, alkoximo, the groups

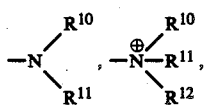

—CO—OR$^{13}$, —CO—NR$^{14}$R$^{15}$, —CS—NR$^{14}$R$^{15}$, —SO$_2$—NR$^{14}$R$^{15}$; cycloalkyl, aryl or a 5- or 6-membered heterocycle, R$^4$ further represents in each case optionally substituted cycloalkyl, aryl or a 5- to 7-membered heterocycle, where D and R$^9$ have the abovementioned meaning, R$^{10}$ represents hydrogen or alkyl, R;hu 11 represents alkyl, acyl, alkylsulphonyl, arylsulphonyl or in each case optionally substituted aryl or aralkyl or R$^{10}$ and R$^{11}$, together with the nitrogen to which they are bound, also represent a 5- to 7-membered heterocycle, R$^{12}$ represents alkyl, R$^{13}$ represents alkyl, R$^{14}$ and R$^{15}$, independently of one another, in each case represent hydrogen, alkyl, cycloalkyl or in each case optionally substituted aryl or aralkyl or R$^{14}$ and R$^{15}$, together with the nitrogen to which they are bound, represent a 5- to 7-membered heterocycle or R$^4$, together with R$^5$ and B or with R$^6$ and B or with R$^7$ and B or with R$^8$ and B or with A and B, can form a 5- or 6-membered ring, have now been found.

It has furthermore been found that the new pyri(mi)dyl-oxy- and -thio-benzoic acid derivatives of the formula (I),

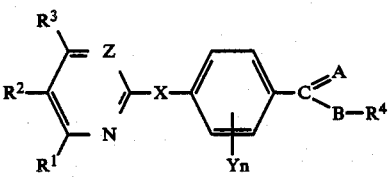

in which $R^1$, $R_2$ and $R_3$, independently of one another, in each case represent hydrogen, halogen, alkyl, optionally substituted alkoxy, haloalkyl, alkenyl or optionally substituted amino or $R^1$ and $R^2$ or $R^2$ and $R^3$ together represent a fused 3- to 6-membered carbocyclic ring, with the proviso that at least one of the radicals $R^1$, $R^2$ or $R^3$ represents alkyl or a part of the 3- to 6-membered fused carbocyclic ring, Z represents a (CH) group or a nitrogen atom, X represents oxygen or sulphur, Y represents halogen, nitro, cyano, amino, alkylcarbonylamino, alkoxycarbonylamino, phenoxycarbonylamino, alkyl, alkoxy or haloalkyl, where Y can be identical or different, n represents an integer from 0 to 4, A represents oxygen, sulphur, a radical $R^5$—N= or a radical $R^6$O—N=, where $R^5$ represents hydrogen, alkyl, hydroxyalkyl, alkenyl, in each case optionally substituted cycloalkyl, aryl or aralkyl, $R^6$ represents hydrogen, in each case optionally substituted alkyl or mono- or poly-unsaturated alkenyl, B represents oxygen, sulphur, a radical

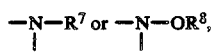

where $R^7$ represents hydrogen, alkyl which is optionally substituted by halogen, cyano or a radical —D—$R^9$, or alkenyl, where D represents oxygen, sulphur, sulphinyl or sulphonyl, and $R^9$ represents hydrogen, alkyl, mono- or polyunsaturated alkenyl or in each case optionally subsituted aryl or aralkyl, or —CO-alkyl, $R^8$ represents hydrogen, in each case optionally substituted alkyl or mono- or poly-unsaturated alkenyl and $R^4$ represents optionally substituted saturated or unsaturated aliphatic radical, where selected substituent are: halogen, nitro, cyano, a radical —D—$R^9$, alkoximo, the groups

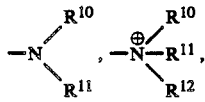

—CO—$OR^{13}$, —CO—$NR^{14}R^{15}$, —CS—$CR^{14}R^{15}$, —$SO_2$—$NR^{14}R^{15}$, cycloalkyl, aryl or a 5- or 6-membered heterocycle:

$R^4$ furthermore represents in each case optionally substituted cycloalkyl, aryl or a 5- to 7-membered heterocycle, where D and $R^9$ have the abovementioned meaning, $R^{10}$ represents hydrogen or alkyl, $R^{11}$ represents alkyl, acyl, alkylsulphonyl, arylsulphonyl or in each case optionally substituted aryl or aralkyl or $R^{10}$ and $R^{11}$, together with the nitrogen to which they are bound, also represent a 5- to 7-membered heterocycle, $R^{12}$ represents alkyl, $R^{13}$ represents alkyl, $R^{14}$ and $R^{15}$, independently of one another, in each case represent hydrogen, alkyl, cycloalkyl or in each case optionally substituted aryl or aralkyl or $R^{14}$ and $R^{15}$, together with the nitrogen to which they are bound, represent a 5- to 7-membered heterocycle or $R^4$, together with $R^5$ and B or with $R^6$ and B or with $R^7$ and B or with $R^8$ and B of with A and B, can form a 5- or 6-membered ring, are obtained according to the processes described below:

(A-$a_1$) compounds of the formula (I), in which A represents oxygen, are obtained, when benzoic acid derivatives of the formula (II),

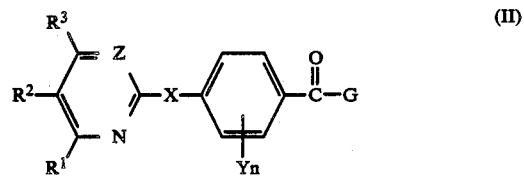

in which $R^1$, $R^2$, $R^3$, Z, X, Y and n have the abovementioned meaning and

G represents halogen, a radical

or —O—$SO_2$aryl or imidazolyl, are reacted with compounds of the formula (III),

 (III)

in which B and $R^4$ have the abovementioned meaning, if appropriate in the presence of a diluent and if appropriate in the presence of an acid binder, or (A-$a_2$) compounds of the formula (I), in which A represents sulphur, are obtained when thiobenzoyl chlorides of the formula (IV),

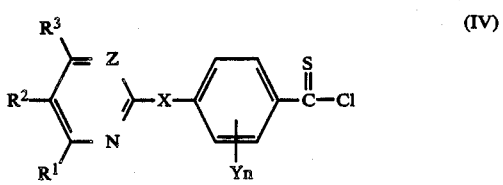

in which $R^1$, $R^2$, $R^3$, Z, X, Y and n have the abovementioned meaning, are reacted with compounds of the formula (III),

 (III)

in which B and $R^4$ have the abovementioned meaning, if appropriate in the presence of a diluent and in the presence of an acid binder, or (A-$a_3$) compounds of the formula (I), in which A and B represent sulphur, are obtained when dithiobenzoic acids of the formula (V),

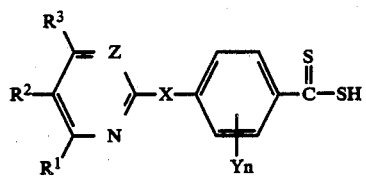 (V)

in which $R^1$, $R^2$, $R^3$, Z, X, Y and n have the abovementioned meaning, are reacted ($a_3$-α) with alkylating agents of the formula (VI)

$$L-R^{4-1} \quad (VI)$$

in which $R^{4-1}$ represents optionally substituted alkyl or aralkyl and L represents halogen or the radical $R^{4-1}$—O—SO$_2$—O—, in the presence of a diluent and if appropriate in the presence of an acid binder, or ($a_3$-β) with olefines of the formula (VII),

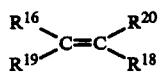 (VII)

in which
$R^{16}$, $R^{18}$, $R^{19}$ and $R^{20}$, independently of one another, in each case represent hydrogen, nitro, cyano, in each case optionally substituted alkyl, cycloalkyl or aryl, or a radical —COOR$^{13}$, —CO—NR$^{14}$R$^{15}$, —C-S—NR$^{14}$R$^{15}$, —SO$_2$—NR$^{14}$R$^{15}$ or the radical —D—R$^9$ or
$R^{16}$ and $R^{20}$ together form a third carbon-carbon bond, where D, $R^9$, $R^{13}$, $R^{14}$ and $R^{15}$ have the abovementioned meaning, in the presence of a diluent and if appropriate in the presence of a catalyst, or (A-$a_4$) compounds of the formula (I) in which A represents sulphur and B represents the radical

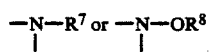

are obtained when
($a_4$-α) dithiobenzoic acid derivatives of the formula (Va),

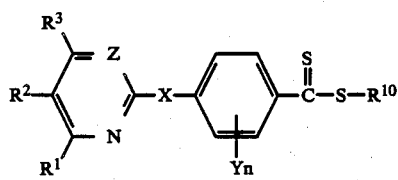 (Va)

in which
$R^1$, $R^2$, $R^3$, Z, X, Y and n have the abovementioned meaning and
$R^{10}$ represents hydrogen or alkyl, particularly hydrogen or C$_1$-C$_4$-alkyl,
are reacted with amines of the formula (VIIIa) or hydroxylamines of the formula (VIIIb),

 (VIIIa)

or

 (VIIIb)

in which $R^4$, $R^7$ and $R^8$ have the abovementioned meaning, if appropriate in the presence of a diluent and if appropriate in the presence of a catalyst, or when ($a_4$-β) benzimide chlorides of the formula (IXa),

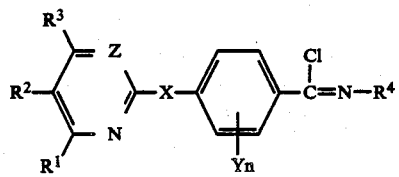 (IXa)

in which $R^1$, $R^2$, $R^3$, $R^4$, Z, X, Y and n have the abovementioned meaning, are reacted with hydrogen sulphide in the presence of a diluent or when ($a_4$-γ) benzoic acid amides of the formula (Ia)

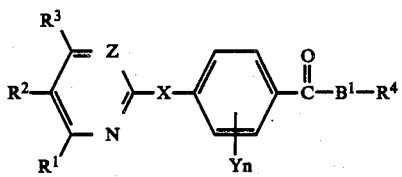 (Ia)

in which
$R^1$, $R^2$, $R^3$, $R^4$, Z, X, Y and n have the abovementioned meaning and
$B^1$ represents the radical

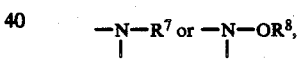

are reacted with sulphurizing agents, if appropriate in the presence of a diluent, or (A-$a_5$) compounds of the formula (I), in which A represents a radical $R^5$—N=, are obtained when ($a_5$-α) benzimide chlorides of the formula (IXb),

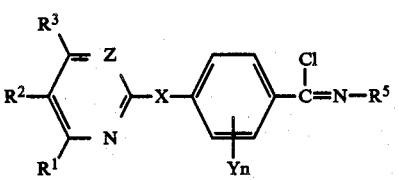 (IXb)

in which $R^1$, $R^2$, $R^3$, $R^5$, Z, X, Y and n have the abovementioned meaning, are reacted with compounds of the formula (III)

$$H-B-R^4 \quad (III)$$

in which B and $R^4$ have the abovementioned meaning, if appropriate in the presence of a diluent and in the presence of an acid binder, or when ($a_5$-β) thiobenzamides of the formula (X)

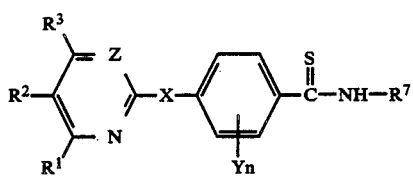

in which $R^1$, $R^2$, $R^3$, $R^7$, Z, X, Y and n have the above-mentioned meaning, are reacted with alkylating agents of the formula (VI),

L—$R^{4-1}$ (VI)

in which $R^{4-1}$ and L have the abovementioned meaning, if appropriate in the presence of a diluent and if appropriate in the presence of an acid binder, or (A-a$_6$) compounds of the formula (I), in which A represents the radical $R^6$—O—N=, are obtained when (a$_6$-α) hydroximic acid halides of the formula (XIa),

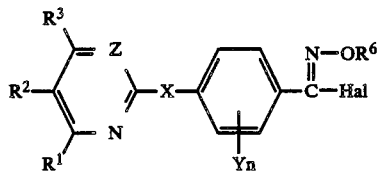

in which
$R^1$, $R^2$, $R_3$, $R^6$, Z, X, Y and n have the abovementioned meaning and
Hal represents chlorine or bromine,
are reacted with compounds of the formula (III),

H—B—$R^4$ (III)

in which B and $R^4$ have the abovementioned meaning, if appropriate in the presence of a diluent and in the presence of an acid binder, or when (a$_6$-β) hydroxamic acids of the formula (XIb),

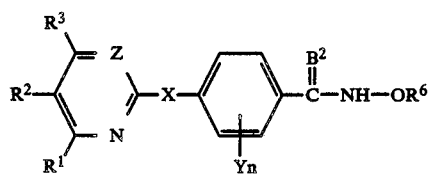

in which
$R^1$, $R^2$, $R^3$, $R^6$, Z, X, Y and n have the abovementioned meaning and
$B^2$ represents oxygen or sulphur,
are reacted with alkylating agents of the formula (VI),

L—$R^{4-1}$ (VI)

in which L and $R^{4-1}$ have the abovementioned meaning, if appropriate in the presence of a diluent and if appropriate in the presence of an acid binder, or when (a$_6$-γ) thiobenzoic acid esters of the formula (Ib),

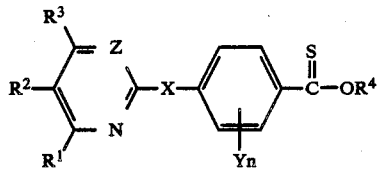

in which $R^1$, $R^2$, $R^3$, $R^4$, Z, X, Y and n have the above-mentioned meaning, are reacted with hydroxylamines of the formula (XII), $R^6$—O—$NH_2$ (XII)

in which $R^6$ has the abovementioned meaning, if appropriate in the presence of a diluent, or (A-a$_7$) compounds of the formula (I), in which $R^4$, A and B together form a heterocyclic ring, are obtained when (a$_7$-α) benzonitriles of the formula (XIII),

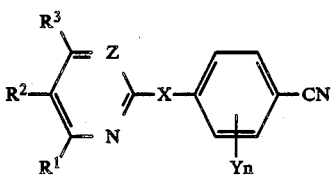

in which $R^1$, $R^2$, $R^3$, Z, X, Y and n have the abovementioned meaning, are reacted with 2- or 3-hydroxyalkylamines of the formula (XIV)

HO—$Alk^1$—$NH_2$ (XIV)

in which $Alk^1$ represents an optionally substituted $C_2$-$C_3$-alkylene chain, where selected substituents are: fluorine, chlorine, $C_1$-$C_3$-arlkyl, $C_1$-$C_3$-alkoxy, hydroxy-$C_1$-$C_3$-alkyl, $C_3$-$C_6$-cycloalkyl or phenyl which is optionally substituted by fluorine, chlorine, methyl, ethyl, methoxy or trifluoromethyl, if appropriate in the presence of a diluent and in the presence of a catalyst, to form the compounds of the formula (Ic),

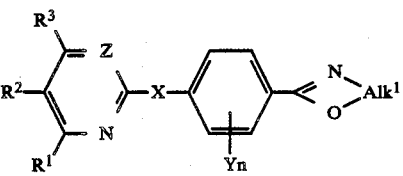

in which $R^1$, $R^2$, $R^3$, $Alk^1$, Z, X, Y and n have the abovementioned meaning, or when (a$_7$-β) thiobenzamides of the formula (Xa)

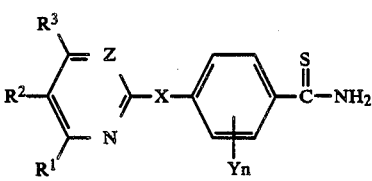

in which $R^1$, $R^2$, $R^3$, Z, X, Y and n have the abovementioned meaning, are reacted with α-halocarbonyl derivatives of the formula (XV), $$\text{Hal}-\underset{R^{22}}{\overset{|}{\text{CH}}}-\underset{O}{\overset{\|}{\text{C}}}-R^{21} \qquad (XV)$$

in which
Hal represents chlorine or bromine,
$R^{21}$ and $R^{22}$, independently of one another, represent hydrogen, alkyl, cycloalkyl or optionally substituted aryl,
if appropriate in the presence of a diluent and in the presence of an acid binder, to form compounds of the formula (Id), (Id) — structure with $R^3$, $R^2$, $R^1$, Z, N, X, Yn, and N=C with $R^{21}$, $R^{22}$, S in which $R^1$, $R^2$, $R^3$, $R^{21}$, $R^{22}$, Z, X, Y and n have the abovementioned meaning, of when
(a7-γ) hydroxamic acids of the formula (Ib-1), (Ib-1) — structure with $R^3$, $R^2$, $R^1$, Z, N, X, Yn, C(=O)—NOH in which $R^1$, $R^2$, $R^3$, Z, X, Y and n have the abovementioned meaning, are reacted with bifunctional alkylating agents of the formula (VIa), $$L^1-\text{Alk}^2-L^2 \qquad (VIa)$$

in which $L^1$ and $L^2$ represent chlorine or bromine and $\text{Alk}^2$ represents an optionally substituted $C_2$- or $C_3$-alkylene chain, where selected substituents are: $C_1$–$C_3$-alkyl, $C_3$–$C_6$-cycloalkyl or phenyl which is optionally substituted by fluorine, chlorine, methyl, ethyl, methoxy or trifluoromethyl, if appropriate in the presence of a diluent and in the presence of an acid binder, or when
(a7-δ) benzamide oximes of the formula (XVI), (XVI) — structure with $R^3$, $R^2$, $R^1$, Z, N, X, Yn, C(=N—OH)—$NH_2$ in which $R^1$, $R^2$, $R^3$, Z, X, Y and n have the abovementioned meaning, are reacted with acylating agents of the formula (XVII), $$G-\overset{O}{\overset{\|}{C}}-R^{4\text{-}2} \qquad (XVII)$$

in which
G has the abovementioned meaning and
$R^{4\text{-}2}$ represents a radical $R^4$ which has been shortened by one carbon atom, where $R^4$ has the abovementioned meaning, and particularly represents alkyl which is optionally substituted by halogen, aryl or the radical —D—$R^9$, cycloalkyl or optionally substituted aryl,
if appropriate in the presence of a diluent and if appropriate in the presence of an acid binder, and the compounds of the formula (XVIa), (XIVa) — structure with $R^3$, $R^2$, $R^1$, Z, N, X, Yn, C(=N—OH)—NH—C(=O)—$R^{4\text{-}2}$ in which $R^1$, $R^2$, $R^3$, $R^{4\text{-}2}$, Z, X, Y and n have the abovementioned meaning, which are thus obtained are reacted with dehydrating agents to form the pyri(mi)dyloxy- or -thiobenzoic acid derivatives of the formula (Ie), (Ie) — structure with $R^3$, $R^2$, $R^1$, Z, N, X, Yn, C(=N—O)—(N=)—$R^{4\text{-}2}$ (oxadiazole ring)

in which $R^1$, $R^2$, $R^3$, $R^{4\text{-}2}$, Z, X, Y and n have the abovementioned meaning, (B) pyri(mi)dyl-oxy- and thiobenzoic acid derivatives of the formula (I) are obtained when
(B-$b_1$) pyri(mi)dine derivatives of the formula (XVIII)

(XVIII) — structure with $R^3$, $R^2$, $R^1$, Z, N, and Hal in which
$R^1$, $R^2$, $R^3$ and Z have the abovementioned meaning and
Hal represents chlorine or bromine,
are reacted with 4-hydroxy or 4-mercapto-benzoic acid derivatives of the formula (XIX), (XIX) — structure H—X—(phenyl with Yn)—C(=A)—B—$R^4$ in which X, Y, n, A, B and $R^4$ have the abovementioned meaning, if appropriate in the presence of a diluent and in the presence of an acid binder, or when
(B-$b_2$) 2-mercapto-pyri(mi)dines of the formula (XX)

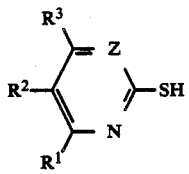

(XX)

in which $R^1$, $R^2$, $R^3$ and Z have the abovementioned meaning, are reacted with 4-halobenzoic acid derivatives of the formula (XXI),

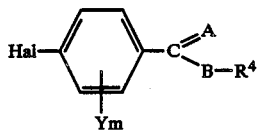

(XXI)

in which
$R^4$, A, B and Y have the abovementioned meaning,
m represents 1, 2 or 3 and
Hal represents chlorine or bromine,
if appropriate in the presence of a diluent and in the presence of an acid binder, or (C) compounds of the formula (I) are obtained from other compounds of the formula (I) by exchange of a substituent Y when (C-$c_1$) compounds of the formula (I), in which Y represents hydrogen in the 3- and/or 5-position, is converted to such compounds of the formula (I), in which Y represents chlorine or bromine, by reaction with a halogenating agent in the presence of a diluent and if appropriate in the presence of a catalyst, or when (C-$c_2$) compounds of the formula (I), in which Y represents nitro, are converted to such compounds of the formula (I), in which Y represents amino by reaction with reducing agents according to known processes, and (C-$c_3$) if appropriate, these amino-substituted compounds of the formula (I) (Y=represents amino) are acylated in a generally conventional fashion using acid chlorides of the formula (XXII),

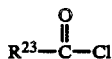

(XXII)

in which $R^{23}$ represents $C_1$-$C_4$-alkyl, $C_1$-$C_4$-alkoxy or di-$C_1$-$C_4$-alkylamine, or using methyl or ethyl isocyanate, or when (C-$c_4$) compounds of the formula (I), in which Y represents amino, are converted into such compounds of the formula (I), in which Y represents halogen or cyano, by reaction with nitrous acid or with an alkyl nitrite, particularly methyl nitrite or ethyl nitrite, if appropriate in the presence of a catalyst, according to known processes, or (D) compounds of the formula (I), in which $R^3$ represents the radical —O—$R^{24}$ or —$NR^{25}R^{26}$, where $R^{24}$, $R^{25}$ and $R^{26}$ have the meaning mentioned below, are obtained when pyri(mi)dyl-oxy- and -thio-benzoic acid derivatives of the formula (If),

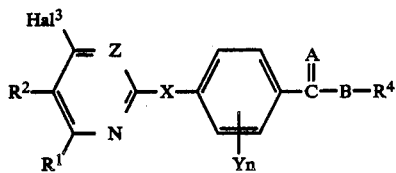

(If)

in which
$R^1$, $R^2$, $R^4$, Z, X, Y, n, A and B have the abovementioned meaning and
$Hal^3$ represents fluorine, chlorine or bromine,
are reacted with alcohols of the formula (XXIII),

H—O—$R^{24}$ (XXIII)

in which $R^{24}$ represents $C_1$-$C_4$-alkyl which is optionally substituted by fluorine, chlorine or methoxy, or $C_2$-$C_4$-alkenyl, if appropriate in the presence of a diluent and in the presence of an acid binder, or are reacted with ammonia, primary or secondary amines of the formula (XXIV)

(XXIV)

in which
$R^{25}$ and $R^{26}$, independently of one another, in each case represent hydrogen or $C_1$-$C_4$-alkyl, or
$R^{25}$ and $R^{26}$, together with the N atom, can also form a 5- to 7-membered heterocyclic ring,
in the presence of a diluent and in the presence of an acid binder.

Finally it has been found that the new pyri(mi)-dyloxy- and -thiobenzoic acid derivatives of the formula (I) have herbicidal, particularly also selective herbicidal, properties and, in addition, also have plant growth-regulating properties.

Surprisingly, the pyri(mi)dyloxy- and -thiobenzoic acid derivatives of the formula (I) according to the invention exhibit clearly improved general herbicidal activity towards weeds than the pyridyl and pyrimidyl ethers and thioethers, known from the state of the art, which are similar compounds chemically and regarding their action.

In addition, the compounds of the formula (I) according to the invention exhibit plant growth-regulating activity.

The pyri(mi)dyloxy- and -thiobenzoic acid derivatives according to the invention are generally defined by means of the formula (I). Compounds of the formula (I),
in which
$R^1$, $R^2$ and $R^3$, independently of one another in each case represent hydrogen, fluorine, chlorine, bromine, alkyl having 1 to 6 carbon atoms, alkenyl having 2 to 6 carbon atoms, alkoxy which is optionally substituted by $C_2$-$C_4$-alkenyl or $C_1$-$C_2$-alkoxy, alkylamino, dialkylamino having 1 to 4 carbon atoms in each of the individual alkyl moieties, where, in the case of dialkylamino, the alkyl substituents can form a 5- to 7-membered heterocyclic ring with the nitrogen atom to which they are bound, or amino, alkenylamino or dialkenylamino having 3 to 4 carbon atoms in each of the individual alkenyl moieties, or trifluoromethyl or $R^1$ and $R^2$ or $R^2$ and $R^3$ together represent a 5- or 6-membered carbocyclic ring, with the proviso that at least one of the radicals $R^1$, $R^2$ or $R^3$ represents alkyl having 1 to 6 carbon atoms, trifluoromethyl or a part of the fused 5- or 6-membered carbocyclic ring, Z represents a group of a nitrogen atom, X represents oxygen or sulphur, Y represents fluorine, chlorine, bromine, iodine, nitro, cyano or amino, alkyl, alkoxy, haloalkyl, alkylcarbonylamino or alkoxycarbonylamino, in each case with 1 to 4 carbon atoms in the alkyl moiety and, in the case of haloalkyl having 1 to 5 halogen atoms, where halogen represents fluorine, chlorine, bromine or iodine, or phenoxycarbonylamino, where Y can be identical or different, n represents an integer 0, 1, 2, 3 or 4, A represents oxygen, sulphur, a radical $R^5$—N= or a radical $R^6O$—N=, where $R^5$ represents hydrogen, alkyl, hydroxyalkyl or alkoxyalkyl, in each case having 1 to 4 carbon atoms in the individual alkyl moieties, alkenyl having 3 to 4 carbon atoms, cycloalkyl having 3 to 7 carbon atoms which is optionally substituted by fluorine, chlorine, bromine, $C_1$-$C_4$-alkyl or $C_1$-$C_4$-alkoxy, phenyl, benzyl or phenethyl which are in each case optionally substituted by fluorine, chlorine, bromine, iodine, $C_1$-$C_4$-alkyl, $C_1$-$C_4$-alkoxy, $C_1$-$C_4$-alkylthio, $C_1$-$C_4$-alkylsulphinyl, $C_1$-$C_4$-alkylsulphonyl, or halo-$C_1$-$C_4$-alkylsulphonyl, $R^6$ represents hydrogen or alkyl having 1 to 4 carbon atoms or alkenyl having 3 to 4 carbon atoms, B represents oxygen, sulphur or a radical

where $R^7$ represents hydrogen, alkyl, having 1 to 4 carbon atoms, which is optionally substituted by fluorine, chlorine, bromine, iodine, cyano, a radical —D—$R^9$, or alkenyl having 2 to 4 carbon atoms, where D represents oxygen, sulphur, sulphinyl or sulphonyl and $R^9$ represents hydrogen, alkyl having 1 to 4 carbon atoms, alkenyl having 3 to 4 carbon atoms, in each case optionally substituted phenyl, benzyl or phenethyl, where fluorine, chlorine, bromine, $C_1$-$C_4$-alkyl or $C_1$-$C_4$-alkoxy are selected as phenyl substituents, $R^4$ represents in each case optionally substituted alkyl having 1 to 12 carbon atoms, in each case mono- or polyunsaturated alkenyl or alkinyl having in each case up to 12 carbon atoms, where selected substituents in each case are: fluorine, chlorine, cyano, alkoximino having 1 to 4 carbon atoms in the alkyl moiety, cycloalkyl, having 3 to 6 carbon atoms, which is optionally substituted by $C_1$-$C_4$-alkyl and/or fluorine and/or chlorine, phenyl which is optionally substituted by fluorine, chlorine, bromine, nitro, trifluoromethyl, $C_1$-$C_4$-alkyl, $C_1$-$C_4$-alkoxy, $C_1$-$C_4$-alkylthio, $C_1$-$C_4$-alkylsulphinyl or $C_1$-$C_4$-alkylsulphonyl, a 5- or 6-membered heterocycle which can contain 1 to 3 further heteroatoms from the series comprising oxygen and/or sulphur and/or nitrogen, a radical —D—$R^9$, a radical

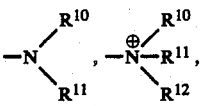

—CO—$OR^{13}$, —CO—$NR^{14}R^{15}$, —CS—$NR^{14}R^{15}$, —$SO_2$—$NR^{14}R^{15}$;

where

D and $R^9$ have the abovementioned meaning, $R^{10}$ represents hydrogen or alkyl having 1 to 4 carbon atoms, $R^{11}$ represents alkyl having 1 to 4 carbon atoms, acyl, alkylsulphonyl having 1 to 4 carbon atoms or phenylsulphonyl or $R^{10}$ and $R^{11}$, together with the nitrogen to which they are bound, represent a 5- to 7-membered heterocycle, $R^{12}$ represents alkyl having 1 to 4 carbon atoms, $R^{13}$ represents alkyl having 1 to 4 carbon atoms, $R^{14}$ and $R^{15}$, in each case independently of one another, represent hydrogen or alkyl having 1 to 6 carbon atoms or $R^{14}$ and $R^{15}$, together with the nitrogen to which they are bound, represent a 5- or 6-membered heterocycle, or $R^4$, furthermore, represents cycloalkyl, having 3 to 8 carbon atoms, which is optionally substituted by fluorine, chlorine, $C_1$-$C_4$-alkyl, $C_1$-$C_4$-alkoxy, $C_2$-$C_4$-alkenyl and/or halo-$C_1$-$C_4$-alkyl where halo represents 1 to 5 fluorine and/or chlorine atoms, optionally substituted phenyl, where selected substituents are: fluorine, chlorine, bromine, $C_1$-$C_4$-alkyl, halo-$C_1$-$C_4$-alkyl where halo represents 1 to 5 fluorine and/or chlorine and/or bromine atoms, or a radical —$D^1$—$R^{17}$, where $D^1$ represents oxygen, sulphur, sulphinyl or sulphonyl, $R^{17}$ represents hydrogen, $C_1$-$C_4$-alkyl, halo-$C_1$-$C_4$-alkyl where halo represents 1 to 5 fluorine and/or chlorine atoms, $C_3$-$C_4$-alkenyl, a radical —CO—O—$C_1$-$C_4$-alkyl,

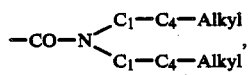

sulphonamide which is optionally mono- or disubstituted on the nitrogen by $C_1$-$C_4$-alkyl, $R^4$, furthermore, represents a 5- to 7-membered heterocycle which can contain 1 to 3 identical or different heteroatoms from the series comprising oxygen, nitrogen or sulphur and which is optionally substituted by fluorine, chlorine, bromine, iodine, $C_1$-$C_4$-alkyl, halo-$C_1$-$C_4$-alkyl where halo represents 1 to 5 identical or different fluorine, chlorine, bromine or iodine atoms, amino, alkylamino or dialkylamino having 1 to 4 carbon atoms in each of the individual alkyl moieties, by nitro, cyano, the radical —D—$R^9$ (with the same meaning for D and $R^9$ as above), the radical —CO—O—$C_1$-$C_4$-alkyl, CO—NH—$C_1$-$C_4$-alkyl or —CO—N($C_1$-$C_4$-alkyl)$_2$, and which can contain carbocyclic or further heterocyclic fused rings, or $R^4$, together with $R^5$, $R^6$, $R^7$ or $R^8$ and B, or together with A and B, forms a 5- or 6-membered ring, are preferred.

Compounds of the formula (I), in which $R^1$, $R^2$ and $R^3$, independently of one another, in each case represent hydrogen, fluorine, chlorine, bromine, alkyl having 1 to 4 carbon atoms, alkoxy which is optionally substituted by $C_2$-$C_4$-alkenyl or $C_1$-$C_2$-alkoxy, alkylamino, dialkylamino having 1 to 4 carbon atoms in each of the individual alkyl moieties, where, in the case of dialkylamino, the alkyl substituents, together with the nitrogen atom to which they are bound, can form a 5- to 7-membered heterocyclic ring, amino, alkenylamino or dialkenylamino having 3 to 4 carbon atoms in each of the individual alkenyl moieties, alkenyl having 2 to 6 carbon atoms, or trifluoromethyl, or $R^1$ and $R^2$ or $R^2$ and $R^3$ together represent a 5- or 6-membered carbocyclic ring, with the proviso that at least one of the radicals $R^1$, $R^2$ or $R^3$ represents alkyl having 1 to 4 carbon atoms, trifluoromethyl or a part of the fused 5- or 6-membered carbocyclic ring, Z represents a (CH) group or a nitrogen atom, X represents oxygen or sulphur, Y represents fluorine, chlorine, bromine, iodine, nitro, amino, alkyl, alkoxy, haloalkyl, alkylcarbonylamino, alkoxycarbonylamino having, in each case, 1 to 3 carbon atoms in the alkyl moiety and, in the case of haloalkyl, having 1 to 3 identical or different halo atoms where halo represents fluorine, chlorine, bromine or iodine, or phenoxycarbonylamino, where Y can be identical or different, n represents an integer 0, 1, 2, 3 or 4, A represents oxygen, sulphur, a radical $R^5$—N= or a radical $R^6$O—N=, where $R^5$ represents hydrogen, alkyl or hydroxyalkyl having 1 to 4 carbon atoms in each case, alkenyl having 3 to 4 carbon atoms, cycloalkyl having 3 to 6 carbon atoms which is optionally mono- or tri-substituted, identically or differently, by fluorine, chlorine, bromine, $C_1$-$C_2$-alkyl or $C_1$-$C_2$-alkoxy, phenyl, benzyl or phenethyl which are, in each case, optionally mono- to tri-substituted, identically or differently by fluorine, chlorine, bromine, iodine, $C_1$-$C_2$-alkyl, $C_1$-$C_2$-alkoxy, $C_1$-$C_2$-alkylthio, $C_1$-$C_2$-alkylsulphinyl, $C_1$-$C_2$-alkylsulphonyl or halo-$C_1$-$C_2$-alkylsulphonyl, $R^6$ represents hydrogen or alkyl having 1 to 4 carbon atoms, B represents oxygen, sulphur or a radical

where $R^7$ represents hydrogen, alkyl, having 1 to 4 carbon atoms, which is optionally mono- to tri-substituted, identically or differently, by fluorine, chlorine, bromine, iodine, cyano, alkenyl having 2 to 4 carbon atoms or a radical —D—$R^9$, where D represents oxygen, sulphur or sulphonyl and $R^9$ represents hydrogen, alkyl having 1 to 4 carbon atoms, alkenyl having 3 to 4 carbon atoms, in each case optionally mono- to tri-, identically or differently substituted phenyl, benzyl or phenethyl, where fluorine, chlorine, bromine, $C_1$-$C_2$-alkyl or $C_1$-$C_2$-alkoxy are selected as phenyl substituents, $R^4$ represents optionally mono- to penta-, identically or differently, substituted alkyl having 1 to 10 carbon atoms, in each case optionally mono- to penta-, identically or differently, substituted mono- or polyunsaturated alkenyl or alkinyl having up to 10 carbon atoms in each case, where selected substituents in each case are: fluorine, chlorine, cyano, alkoximino having 1 to 4 carbon atoms in the alkyl part, cycloalkyl, having 3 to 6 carbon atoms, which is optionally mono- to tri-substituted, identically or differently, by $C_1$-$C_4$-alkyl, phenyl which is optionally mono- to tri-substituted, identically or differently, by fluorine, chlorine, bromine, iodine, nitro, trifluoromethyl, $C_1$-$C_2$-alkyl, $C_1$-$C_2$-alkoxy, $C_1$-$C_2$-alkylthio, $C_1$-$C_2$-alkylsulphinyl or $C_1$-$C_4$-alkylsulphonyl, a 5- or 6-membered heterocycle which can contain 1 to 3 heteroatoms from the series comprising oxygen and/or sulphur and/or nitrogen, a radical —D—$R^9$, a radical

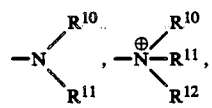

—CO—$OR^{13}$, —CO—$NR^{14}R^{15}$, —CS—$NR^{14}R^{15}$, where

D and $R^9$ have the abovementioned meaning, $R^{10}$ represents hydrogen or alkyl having 1 to 4 carbon atoms, $R^{11}$ represents alkyl having 1 to 4 carbon atoms or acyl, $R^{10}$ and $R^{11}$, together with the nitrogen to which they are bound, represents a 5- to 6-membered heterocycle, $R^{12}$ represents alkyl having 1 to 4 carbon atoms, $R^{13}$ represents alkyl having 1 to 4 carbon atoms, $R^{14}$ and $R^{15}$, in each case independently of one another, represent hydrogen or alkyl having 1 to 6 carbon atoms or $R^{14}$ and $R^{15}$, together with the nitrogen to which they are bound, represent a 5- or 6-membered heterocycle, or $R^4$, furthermore, represents cycloalkyl, having 3 to 7 ring carbon atoms, which is optionally mono- to tri-substituted, identically or differently, by fluorine, chlorine or $C_1$-$C_4$-alkyl, $C_1$-$C_4$-alkoxy, $C_2$-$C_4$-alkenyl or halo-$C_1$-$C_2$-alkyl where halo represents 1 to 3 fluorine and/or chlorine atoms, optionally mono- to tri-, identically or differently, substituted phenyl, where selected substituents are: fluorine, chlorine, bromine, $C_1$-$C_4$-alkyl, trifluoromethyl, or a radical —$D^1$—$R^{17}$, where $D^1$ represents oxygen, sulphur, sulphinyl or sulphonyl, $R^{17}$ represents hydrogen or $C_1$-$C_4$-alkyl, $R^4$, furthermore, represents a 5- to 7-membered heterocycle which can contain 1 to 3 identical or different heteroatoms from the series comprising oxygen, nitrogen or sulphur and which is optionally mono- to tri-substituted, identically or differently, by fluorine, chlorine, bromine, iodine, $C_1$-$C_2$-alkyl, halo-$C_1$-$C_2$-alkyl where halo represents 1 to 3 identical or different fluorine or chlorine atoms, amino, alkylamino or dialkylamino having 1 to 2 carbon atoms in each individual alkyl moiety, by nitro, cyano, or a $C_1$-$C_4$-alkoxy radical, $C_1$-$C_4$-alkylthio radical or $C_1$-$C_4$-alkylsulphonyl radical, or $R^4$, together with $R^5$, $R^6$, $R^7$ or $R^8$ and B or together with A and B, forms a 5- or 6-membered ring, are particularly preferred.

The group of compounds of the formula (I), in which

R[1], R[2] and R[3], independently of one another, in each case represent hydrogen, fluorine, chlorine, bromine, alkyl having 1 to 4 carbon atoms, alkoxy which is optionally substituted by $C_2$-$C_4$-alkenyl or $C_1$-$C_2$-alkoxy, alkylamino, dialkylamino having 1 to 4 carbon atoms in each of the individual alkyl moieties, where, in the case of dialkylamino, the alkyl substituents, together with the nitrogen atom to which they are bound, can form a 5- to 7-membered heterocyclic ring, amino, alkenylamino or dialkenylamino having 3 to 4 carbon atoms in each of the individual alkenyl moieties, alkenyl having 2 to 6 carbon atoms, trifluoromethyl, or R[1] and R[2] or R[2] and R[3] together represent a 5- or 6-membered carbocyclic ring, with the proviso that at least one of the radicals R[1], R[2] or R[3] represents alkyl having 1 to 4 carbon atoms, trifluoromethyl or a part of the fused 5- or 6-membered carbocyclic ring, Z represents a nitrogen atom, X represents oxygen or sulphur, Y represents fluorine, chlorine, bromine, iodine, nitro, amino, alkyl, alkoxy, haloalkyl, alkylcarbonylamino, alkoxycarbonylamino having, in each case, 1 to 3 carbon atoms in the alkyl moiety and, in the case of haloalkyl, having 1 to 3 halo atoms where halo represents fluorine, chlorine, bromine and/or iodine, or phenoxycarbonylamino, where Y can be identical or different, n represents an integer 0, 1, 2 or 3, A represents oxygen or sulphur, B represents oxygen, sulphur or a radical

where

R[7] represents hydrogen, alkyl, having 1 to 4 caron atoms, which is optionally mono- to trisubstituted, identically or differently, by fluorine, chlorine, bromine, iodine, cyano or alkenyl having 2 to 4 carbon atoms, R[4] represents in each case optionally mono- to penta-, identically or differently, substituted alkyl having 1 to 10 carbon atoms, in each case mono- or polyunsaturated alkenyl or alkinyl having up to 10 carbon atoms in each case, where selected substituents in each case are: fluorine, chlorine, cyano, alkoximino having 1 to 4 carbon atoms in the alkyl moiety, cycloalkyl, having 3 to 6 carbon atoms, which is optionally substituted by $C_1$-$C_4$-alkyl, phenyl which is optionally substituted by fluorine, chlorine, bromine, iodine, nitro, trifluoromethyl, $C_1$-$C_2$-alkyl, $C_1$-$C_2$-alkoxy, $C_1$-$C_2$-alkylthio, $C_1$-$C_2$-alkylsulphinyl or $C_1$-$C_4$-alkylsulphonyl, a 5- or 6-membered heterocycle which can contain 1 to 3 heteroatoms from the series comprising oxygen and/or sulphur and/or nitrogen, a radical —D—R[9], a radical

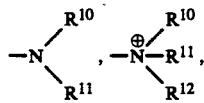

—CO—OR[13], —CO—NR[14]R[15], —CS—NR[14]R[15], where

D represents oxygen, sulphur or sulphonyl and

R[9] represents hydrogen, alkyl having 1 to 4 carbon atoms, alkenyl having 3 to 4 carbon atoms, in each case optionally mono- to tri-, identically or differently, substituted phenyl, benzyl or phenethyl, where fluorine, chlorine, bromine, $C_1$-$C_2$-alkyl or $C_1$-$C_2$-alkoxy are selected as phenyl substituents, R[10] represents hydrogen or alkyl having 1 to 4 carbon atoms, R[11] represents alkyl having 1 to 4 carbon atoms or acyl, R[10] and R[11], together with the nitrogen to which they are bound, represent a 5- or 6-membered heterocycle, R[12] represents alkyl having 1 to 4 carbon atoms, R[13] represents alkyl having 1 to 4 carbon atoms, R[14] and R[15], in each case independently of one another, represent hydrogen or alkyl having 1 to 6 carbon atoms or R[14] and R[15], together with the nitrogen to which they are bound, represent a 5- or 6-membered heterocycle, or R[4], furthermore, represents cycloalkyl, having 3 to 6 carbon atoms, which is optionally mono- to tri-substituted, identically or differently, by fluorine, chlorine or $C_1$-$C_4$-alkyl, $C_1$-$C_4$-alkoxy, $C_2$-$C_4$-alkenyl or halo-$C_1$-$C_2$-alkyl, where halo represents 1 to 3 fluorine and/or chlorine atoms, benzyl, phenethyl, optionally mono- to tri-, identically or differently, substituted phenyl, where selected substituents are: fluorine, chlorine, bromine, $C_1$-$C_4$-alkyl or trifluoromethyl, or a radical —D[1]—R[17], where D[1] represents oxygen, R[17] represents hydrogen or $C_1$-$C_4$-alkyl, R[4], furthermore, represents a 5- or 7-membered heterocycle which can contain 1 to 3 identical or different heteroatoms from the series comprising oxygen, nitrogen or sulphur and which is optionally mono- to tri-substituted, identically or differently, by fluorine, chlorine, bromine, iodine, $C_1$-$C_2$-alkyl, halo-$C_1$-$C_2$-alkyl where halo represents 1 to 3 identical or different fluorine or chlorine atoms, amino, alkylamino or dialkylamino having 1 to 2 carbon atoms in each of the individual alkyl moieties, nitro, cyano, $C_1$-$C_4$-alkoxy, $C_1$-$C_4$-alkylthio or $C_1$-$C_4$-alkylsulphonyl, or R[4], together with R[5], R[6], R[7] or R[8] and B or together with A and B, forms a 5- or 6-membered ring, is very particularly preferred.

The compounds in which R[1], R[2], R[3], Z, X, Y, n, B, R[7], R[4], D, R[9], R[10], R[11], R[12], R[13], R[14], R[15], D[1] and R[17] have the abovementioned very particularly preferred definition and in which A represents oxygen are a particularly preferred group of compounds of the formula (I).

A further very particularly preferred group of compounds of the formula (I) are those in which R[1], R[2] and R[3], independently of one another, in each case represent hydrogen, fluorine, chlorine, bromine, alkyl having 1 to 4 carbon atoms, alkoxy which is optionally substituted by $C_2$-$C_4$-alkenyl or $C_1$-$C_2$-alkoxy, alkylamino, dialkylamino having 1 to 4 carbon atoms in each of the individual alkyl moeities, where, in the case of dialkylamino, the alkyl substituents, together with the nitrogen atom to which they are bound, can form a 5- or 7-membered heterocyclic ring, amino, alkenylamino or dialkenylamino having 3 to 4 carbon atoms in each of the individual alkenyl moieties, alkenyl having 2 to 6 carbon atoms or trifluoromethyl or $R^1$ and $R^2$ or $R^2$ and $R^3$ together represent a 5- or 6-membered carbocyclic ring, with the proviso that at least one of the radicals $R^1$, $R^2$ or $R^3$ represents alkyl having 1 to 4 carbon atoms, trifluoromethyl or a part of the fused 5- or 6-membered carbocyclic ring, Z represents a nitrogen atom, X represents oxygen or sulphur, Y represents fluorine, chlorine, bromine, iodine, nitro, amino, alkyl, alkoxy, haloalkyl, alkylcarbonylamino, alkoxycarbonylamino having 1 to 3 carbon atoms in the alkyl moieties in each case and, in the case of haloalkyl, having 1 to 3 halo atoms, where halo represents fluorine, chlorine, bromine and/or iodine, or phenoxycarbonylamino, where Y can be identical or different, n represents an integer 0, 1, 2 or 3, A represents a radical $R^5$—N= or a radical $R^6O$—N=, where $R^5$ represents hydrogen, alkyl or hydroxyalkyl having 1 to 14 carbon atoms in each case or alkenyl having 3 to 4 carbon atoms, $R^6$ represents hydrogen or alkyl having 1 to 4 carbon atoms, B represents oxygen, sulphur or a radical

where $R^7$ represents hydrogen, alkyl, having 1 to 4 carbon atoms, which is optionally mono- to tri-substituted, identically or differently, by fluorine, chlorine, bromine, iodine, cyano or alkenyl having 2 to 4 carbon atoms, $R^4$ represents in each case optionally mono- to penta-, identically or differently, substituted alkyl having 1 to 10 carbon atoms, in each case mono- or polyunsaturated alkenyl or alkinyl having up to 10 carbon atoms in each case, where selected substituents in each case are: fluorine, chlorine, cyano, alkoximino having 1 to 4 carbon atoms in the alkyl moiety, cycloalkyl, having 3 to 6 carbon atoms, which is optionally mono- or tri-substituted, identically or differently, by $C_1$–$C_4$-alkyl, phenyl which is optionally mono- to tri-substituted, identically or differently, by fluorine, chlorine, bromine, iodine, nitro, trifluoromethyl, $C_1$–$C_2$-alkyl, $C_1$–$C_2$-alkoxy, $C_1$–$C_2$-alkylthio, $C_1$–$C_2$-alkylsulphinyl or $C_1$–$C_4$-alkylsulphonyl, a 5- or 6-membered heterocycle which can contain 1 to 3 heteroatoms from the series comprising oxygen and/or sulphur and/or nitrogen, a radical —D—$R^9$, where D represents oxygen, sulphur or sulphonyl and $R^9$ represents hydrogen, alkyl having 1 to 4 carbon atoms, alkenyl having 3 to 4 carbon atoms, in each case optionally mono- to tri-, identically or differently, substituted phenyl, benzyl or phenethyl, where fluorine, chlorine, bromine, $C_1$–$C_2$-alkyl or $C_1$–$C_2$-alkoxy are selected as phenyl substituents, $R^4$, furthermore, represents cycloalkyl, having 3 to 6 carbon atoms, which is optionally mono- to tri-substituted, identically or differently, by fluorine, chlorine or $C_1$–$C_4$-alkyl, optionally mono- to tri-, identically or differently, substituted phenyl, where selected substituents are: fluorine, chlorine, bromine, $C_1$–$C_4$-alkyl, or trifluoromethyl, or a radical —$D^1$—$R^{17}$, where $D^1$ represents oxygen, $R^{17}$ represents hydrogen or $C_1$–$C_4$-alkyl, $R^4$, furthermore, represents a 5- to 7-membered heterocycle which can contain 1 to 3 identical or different heteroatoms from the series comprising oxygen, nitrogen or sulphur and which is optionally mono- to trisubstituted, identically or differently, by fluorine, chlorine, bromine, iodine, $C_1$–$C_2$-alkyl, halo-$C_1$–$C_2$-alkyl where halo represents 1 to 3 identical or different fluorine or chlorine atoms, by amino, alkylamino or dialkylamino having 1 to 2 carbon atoms in each of the individual alkyl moieties, by nitro, cyano, $C_1$–$C_4$-alkoxy, $C_1$–$C_4$-alkylthio or $C_1$–$C_4$-alkylsulphonyl, or $R^4$, together with $R^5$, $R^6$, $R^7$ or $R^8$ and B or together with A and B, forms a 5- or 6-membered ring.

Another very particularly preferred group of compounds of the formula (I) are those in which Z represents a (CH) group, $R^1$, $R^2$, and $R^3$, independently of one another, in each case represent hydrogen, methyl, ethyl, fluorine, chlorine, bromine, amino or methylamino, X represents sulphur, Y represents fluorine, chlorine, bromine, methyl or methoxy, n represents 0, 1 or 2, A represents oxygen or sulphur, B represents oxygen or a radical

where $R^7$ represents hydrogen, methyl or ethyl, and $R^4$ represents $C_1$- to $C_6$-alkyl.

Extremely preferred compounds of the formula (I) are those in which

Z represents nitrogen, $R^1$, $R^2$ and $R^3$, independently of one another in each case represent hydrogen, methyl, ethyl, chlorine, amino or methylamino, X represents sulphur, Y represents fluorine, chlorine, amino, nitro, methyl or methoxy, n represents 0, 1 or 2, A represents oxygen or sulphur, B represents oxygen or a radical

$R^7$ represents hydrogen or methyl and $R^4$ represents optionally mono- to penta-, identically or differently, substituted alkyl having 1 to 8 carbon atoms, where selected substituents are: fluorine, chlorine, trifluoromethyl, methoxy and cyano, $R^4$ furthermore represents optionally mono- to tri-, identically or differently, substituted alkenyl or alkinyl having in each case 3 to 6 carbon atoms, where selected substituents are in each case fluorine and chlorine, or represents cyclopropyl, cyclopentyl or cyclohexyl which are optionally substituted by methyl or ethyl.

If, for example, 4-(4,6-dimethylpyrimidyl-2-oxy)-benzoyl chloride and tert.butylamine are used as starting materials, then the course of the reaction of the process (A-a₁) according to the invention can be represented by means of the following scheme:

the invention can be represented by means of the following scheme:

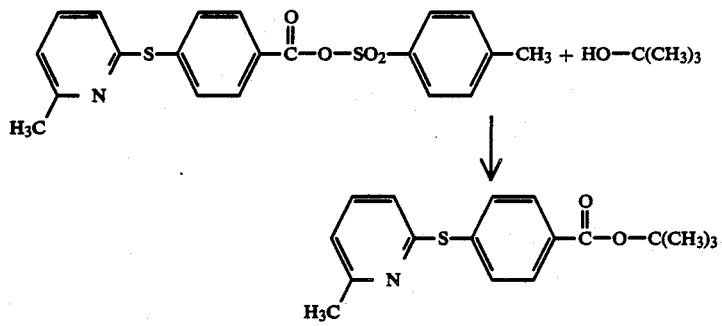

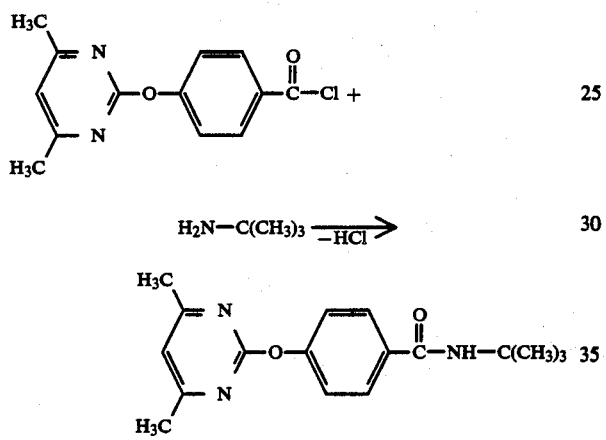

If, for example, the mixed anhydride of 4-(4-methyl-pyrimidyl-2-mercapto)-benzoic acid and ethyl carbonate and 1,1-dimethyl-2-hydroxyethylamine or O-methyl-N-isopropyl-hydroxylamine are used as starting materials, then the course of the reaction of the process (A-a₁) according to the invention can be represented by means of the following scheme:

If, for example, 4-(4,5-dimethyl-pyrimidyl-2-mercapto)-benzoyl imidazole and tert.-butanethiol are used as starting materials, then the course of the reaction of the process (A-a₁) according to the invention can be represented by means of the following scheme:

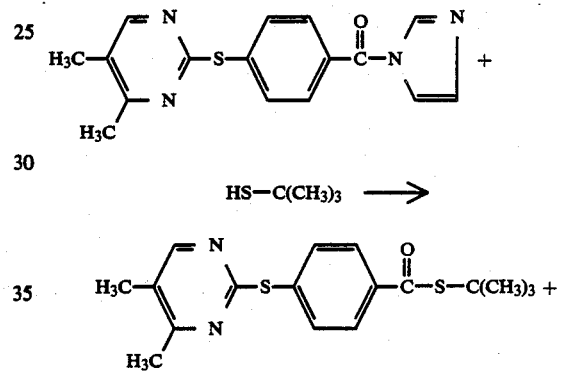

If, for example, 4-(4,6-dimethyl-pyrimidyl-2-mercapto)-thiobenzoyl chloride and acetone cyanohydrin are

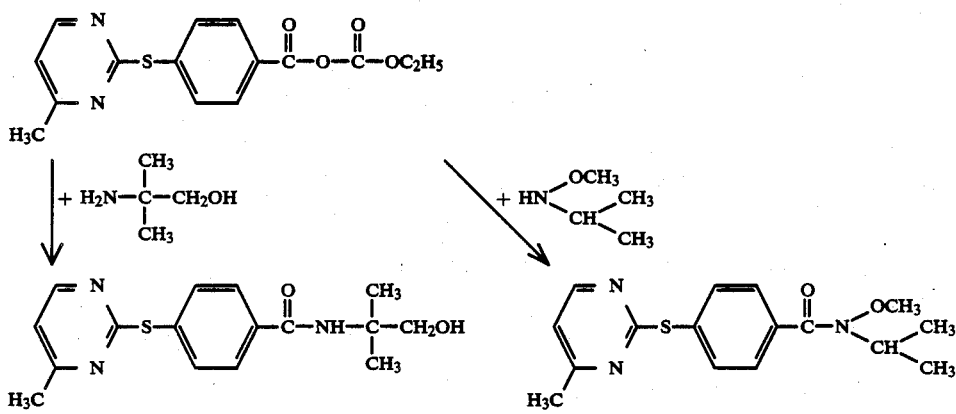

If, for example, the mixed anhydride of 4-(6-methyl-pyridyl-2-mercapto)-benzoic acid and p-toluene-sulphonic acid and tert.butanol are used as starting materials, then the course of the process (A-a₁) according to used as starting materials, then the course of the reaction of the process (A-a₂) according to the invention can be represented by the following scheme:

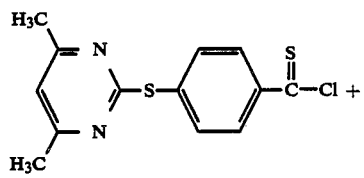

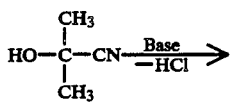

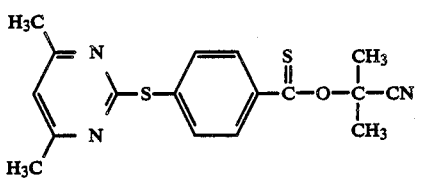

If, for example, 4-(4,6-dimethyl-pyrimidyl-2-oxy)-dithiobenzoic acid and isopropyl bromide are used as starting materials, then the course of the reaction of the process (a$_3$-α) according to the invention can be represented by means of the following scheme:

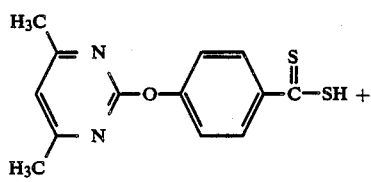

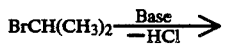

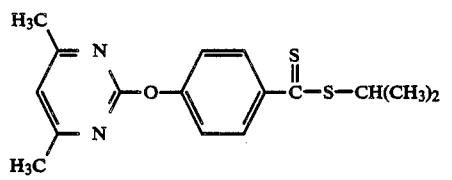

If, for example, 4-(4,6-dimethyl-pyrimidyl-2-oxy)-dithiobenzoic acid and acrylonitrile are used as starting materials, then the course of the reaction of the process (a$_3$-β) according to the invention can be represented by means of the following scheme:

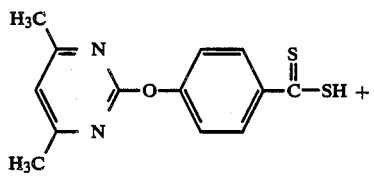

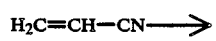

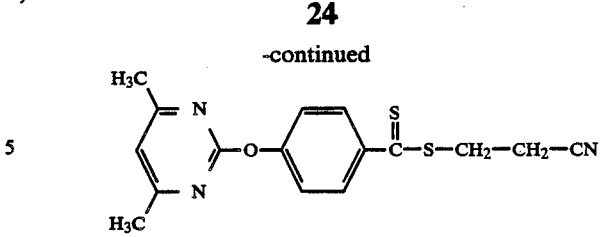

If, for example, 4-(4,6-dimethyl-pyrimidyl-2-oxy)-dithiobenzoic acid and 3-chloroaniline are used as starting materials, then the course of the reaction of the process (a$_4$-α) according to the invention can be represented by means of the following scheme:

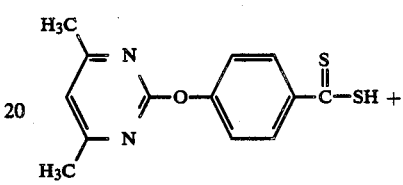

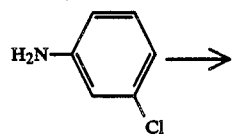

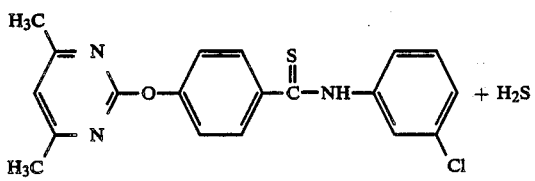

If, for example, 4-(4,6-dimethyl-pyrimidyl-2-mercapto)-N-methyl-benzimide chloride and hydrogen sulphide are used as starting materials, then the course of the reaction of the process (a$_4$-β) according to the invention can be represented by means of the following scheme:

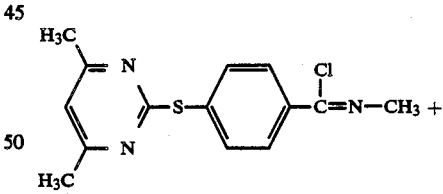

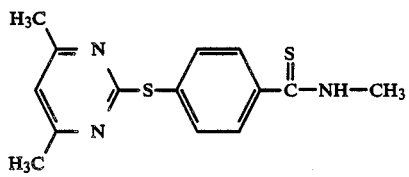

If, for example, N-tert.-butyl-4-(4,6-dimethyl-pyrimidyl-2-mercapto)-benzamide and the Lawesson reagent 2,4-bis-(4-methoxy-phenyl)-2,4-dithiono-1,2,3,4-dithiadiphosphetane are used as starting materials, then the course of the reaction of the process (a$_4$-γ) according to the invention can be represented by means of the following scheme:

If, for example, N-tert.-butyl-4-(4,6-dimethyl-pyrimidyl-2-mercapto)-benzimide chloride and ethanol or ethanethiol or dimethylamine or N,O-dimethylhydroxylamine are used as starting materials, then the courses of the reactions of the process (a₅-α) according to the invention can be represented by means of the following scheme:

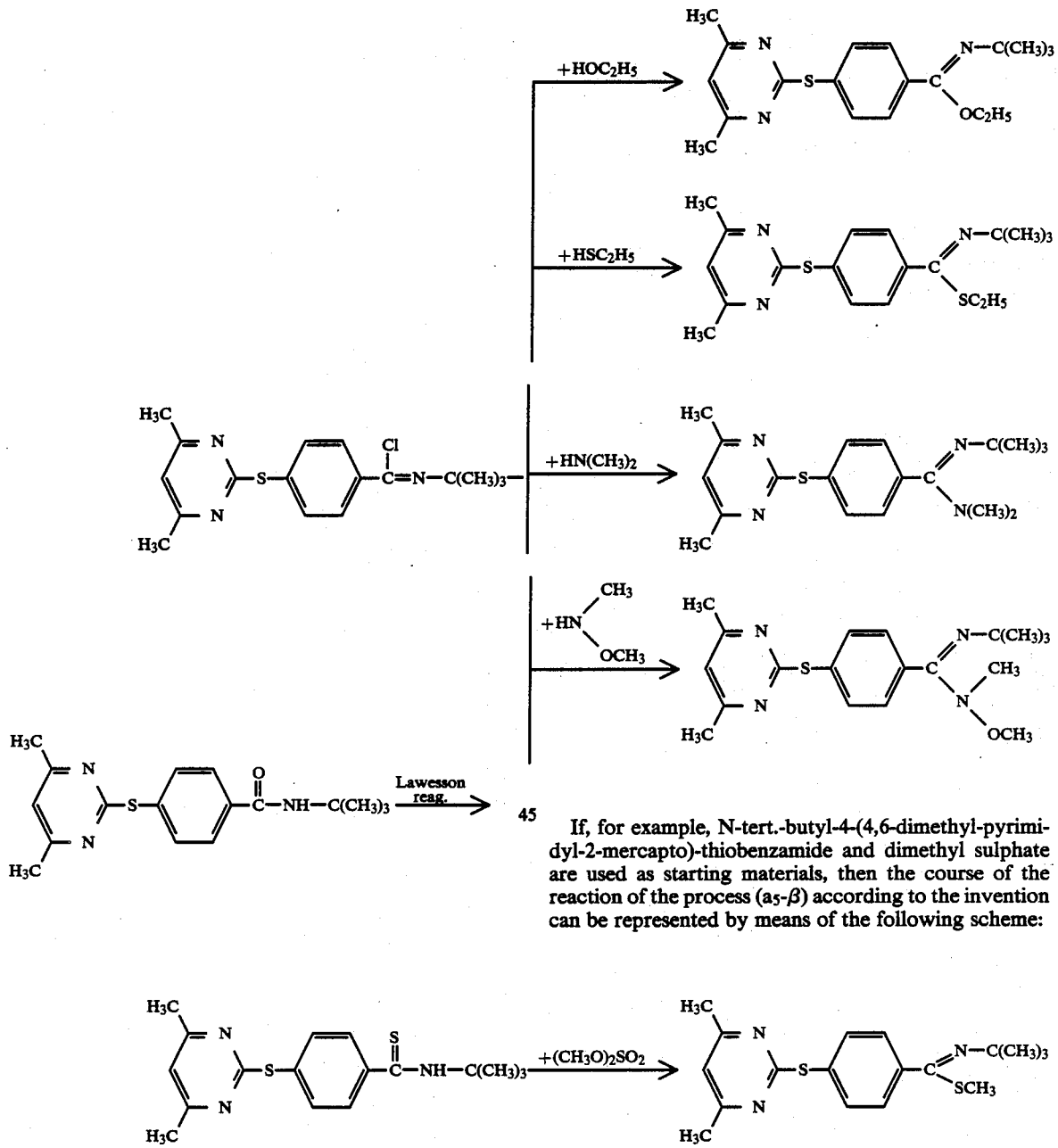

If, for example, N-tert.-butyl-4-(4,6-dimethyl-pyrimidyl-2-mercapto)-thiobenzamide and dimethyl sulphate are used as starting materials, then the course of the reaction of the process (a₅-β) according to the invention can be represented by means of the following scheme:

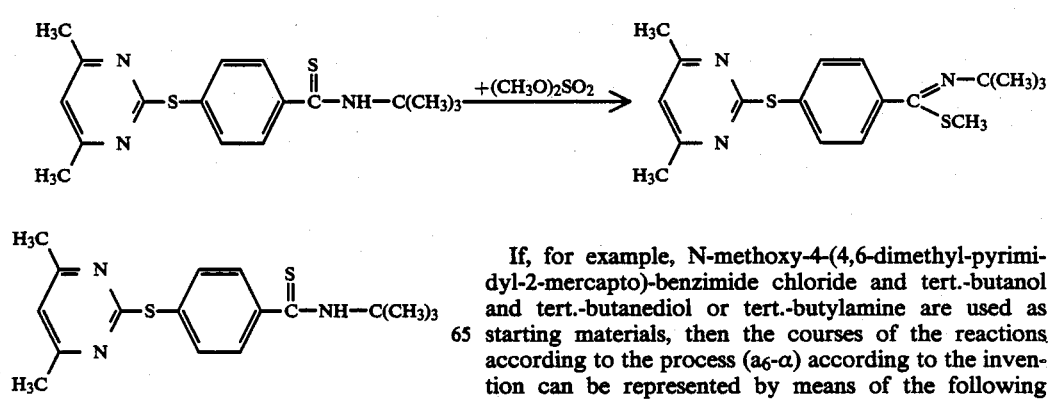

If, for example, N-methoxy-4-(4,6-dimethyl-pyrimidyl-2-mercapto)-benzimide chloride and tert.-butanol and tert.-butanediol or tert.-butylamine are used as starting materials, then the courses of the reactions according to the process (a₆-α) according to the invention can be represented by means of the following scheme:

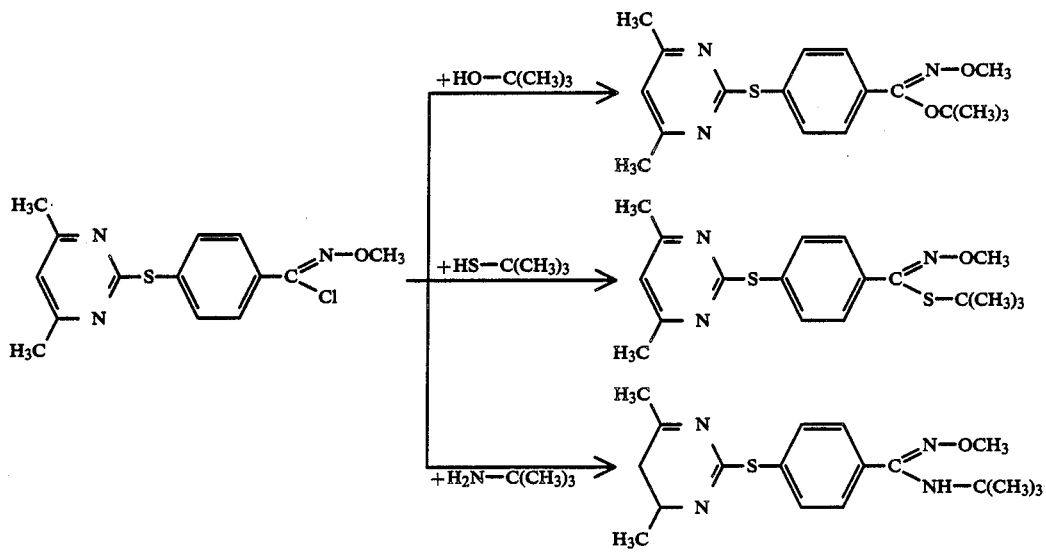

If, for example, 0-methyl 4-(4,6-dimethyl-pyrimidyl-2-mercapto)-benzohydroxamate and allyl bromide are used as starting materials, then the course of the reaction of the process (a6-β) according to the invention can be represented by means of the following scheme:

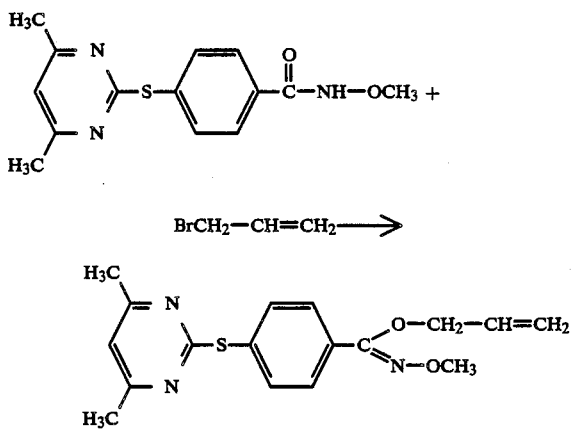

If, for example, 0-methyl 4-(4,6-dimethyl-pyrimidyl-2-mercapto)-thiobenzoate and 0-methylhydroxylamine are used as starting materials, then the course of the reaction of the process (a6-γ) according to the invention can be represented by means of the following scheme:

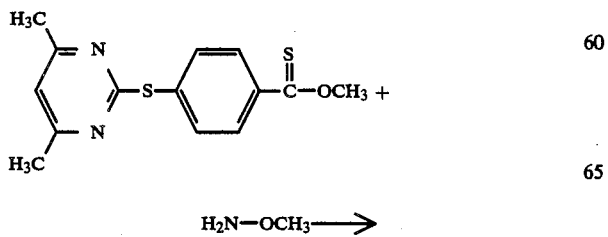

-continued

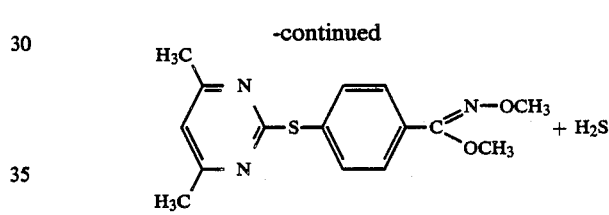

If, for example, 4-(4,6-dimethyl-pyrimidyl-2-mercapto)-benzonitrile and 2-methyl-2-amino-propanol are used as starting materials, then the course of the reaction of the process (a7-α) according to the invention can be represented by means of the following scheme:

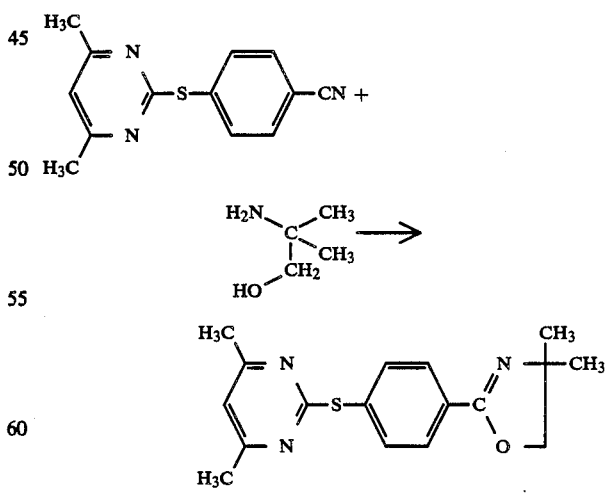

If, for example, 4-(4,6-dimethyl-pyrimidyl-2-mercapto)-thiobenzamide and bromopinacolone are used as starting materials, then the course of the reaction of the process (a7-β) according to the invention can be represented by means of the following scheme:

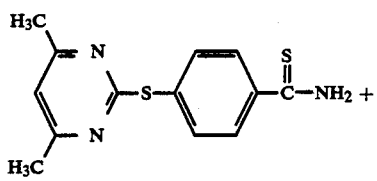

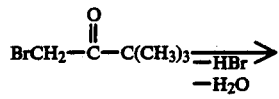

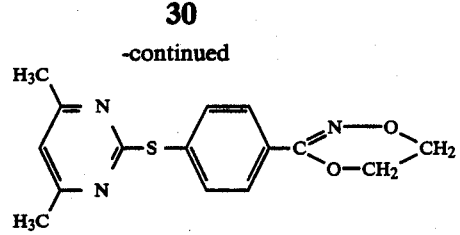

If, for example, 4-(4,6-dimethyl-pyrimidyl-2-mercapto)-benzamide oxime and pivaloyl chloride are used as starting materials, then the course of the reaction of the process (a7-δ) according to the invention can be represented by means of the following scheme:

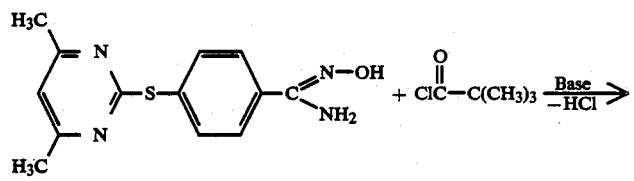

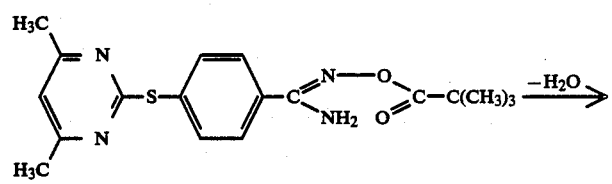

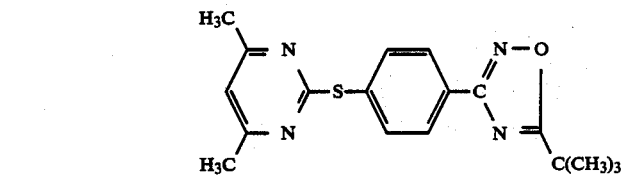

If, for example, 2-chloro-4,6-dimethyl-pyrimidine and N-tert.-butyl-4-mercapto-benzamide are used as starting materials, then the course of the reaction of the process (B-b1) according to the invention can be represented by means of the following scheme:

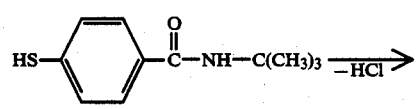

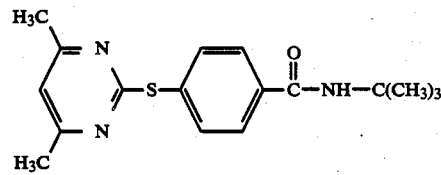

If, for example, 4-(4,6-dimethyl-pyrimidyl-2-mercapto)-benzohydroxamic acid and 1,2-dibromoethane are used as starting materials, then the course of the reaction of the process (a7-γ) according to the invention can be represented by means of the following scheme:

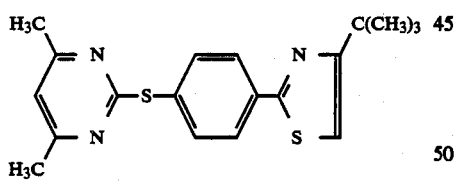 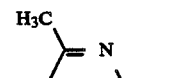

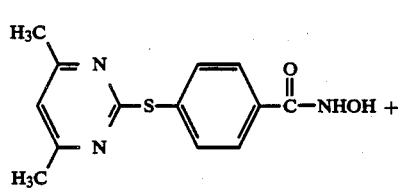

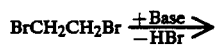

If, for example, 2-mercapto-4,6-dimethyl-pyrimidine and N-tert.-butyl-4-chloro-3-nitro-benzamide are used as starting materials, then the course of the reaction of the process (B-b₂) according to the invention can be represented by means of the following scheme:

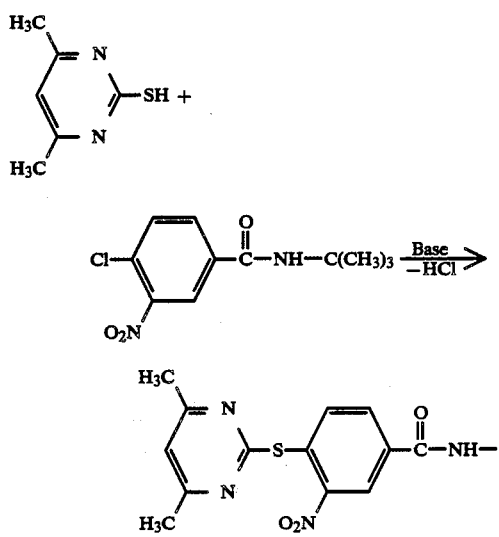

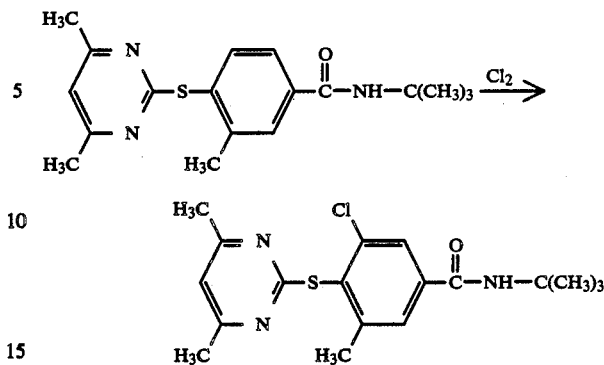

If, for example, N-tert.-butyl-4-(4,6-dimethyl-pyrimidyl-2-mercapto)-3-nitro-benzamide is reduced using hydrogen to form the corresponding amino compound and if this is reacted with acetyl chloride or nitrous acid and copper chloride, then the courses of the reactions of the processes (C-c₂), (C-c₃) and (C-c₄)) according to the invention can be represented by means of the following scheme:

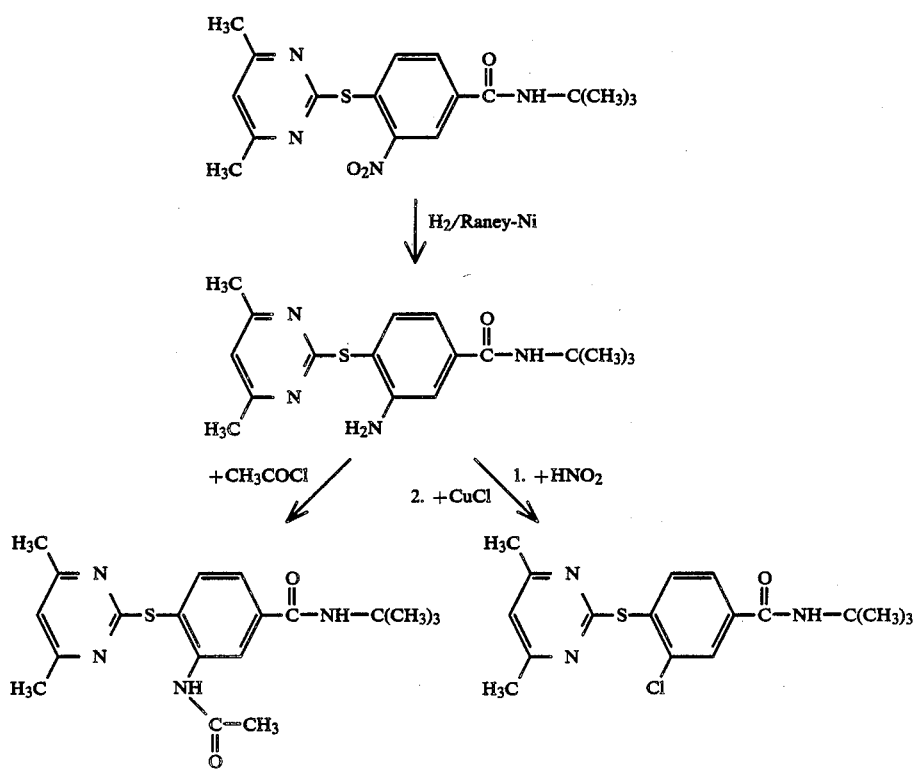

If, for example, N-tert.-butyl-4-(4,6-dimethyl-pyrimidyl-2-mercapto)-3-methyl-benzamide and chlorine are used as starting materials, then the course of the reaction of the process (C-c₁) according to the invention can be represented by means of the following scheme:

If, for example, N-tert.-butyl-4-(4-chloro-6-methyl-pyrimidyl-2-mercapto)-benzamide and ammonia are used as starting materials, then the course of the reaction of the process (D) according to the invention can be represented by means of the following scheme:

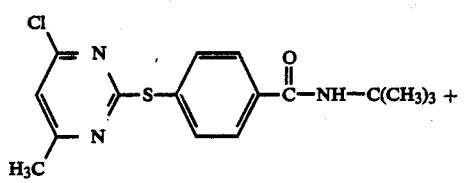

$NH_3 \xrightarrow{-HCl}$

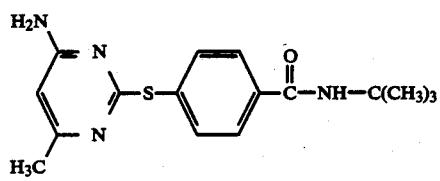

The benzoic acid derivatives which are required to carry out the process (A-$a_1$) according to the invention are generally defined by means of the formula (II).

In this formula (II), $R^1$, $R^2$, $R^3$, Z, X, Y and n preferably or particularly preferably represent the radicals which have already been mentioned in connection with the description of the substances of the formula (I) according to the invention as being preferable or particularly preferable for these substituents. Very particularly preferably, the abovementioned substituents of the formula (II) represent the corresponding radicals of the formula (I) which are listed as being very particularly preferred. G preferably represents chlorine, $C_1$–$C_2$-alkoxycarbonyloxy, toluenesulphonyloxy or benzenesulphonyloxy.

The starting compounds of the formula (II) are not yet known. They are obtained when carboxylic acid derivatives of the formula (XXV)

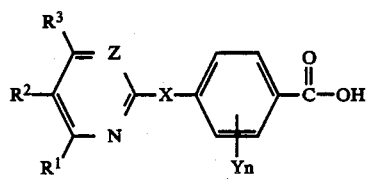
(XXV)

in which $R^1$, $R^2$, $R^3$, Z, X, Y and n have the abovementioned meaning, or their metal salts, particularly their alkali metal or alkaline earth metal salts or their tert.-ammonium salts, are reacted with inorganic acid halides, particularly phosgene, thionyl chloride, phosphoroxy chloride or phosphorous trichloride, or with alkyl chlorocarbonates, particularly methyl or ethyl chlorocarbonates,
or with arylsulphonyl chlorides, particularly benzene- or toluenesulphonyl chloride,
or with imidazole or a reactive derivative from it,
in a conventional fashion at temperatures between 0° C. to 100° C., if appropriate in the presence of a diluent, such as, for example, tetrahydrofuran, and if appropriate in the presence of an acid binder, such as, for example, triethylamine.

The mixed anhydrides of the formula (II), (that is to say G represents O—CO—O alk or —O—SO$_2$—aryl) need not be isolated in pure form, but can be subjected to process (A-$a_1$) in situ.

The carboxylic acid derivatives of the formula (XXV) are also not yet known.

They are obtained when pyr(mi)dine derivatives of the formula (XVIII),

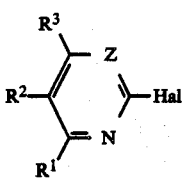
(XVIII)

in which
$R^1$, $R^2$, $R^3$ and Z have the abovementioned meaning, and
Hal represents chlorine or bromine, are reacted with 4-hydroxy- or 4-mercapto-benzonitriles of the formula (XXVI),

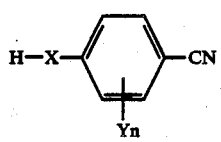
(XXVI)

in which X, Y and n have the abovementioned meaning, if appropriate in the presence of a diluent, such as, for example, sulpholane, and in the presence of an acid binder, such as, for example, potassium hydroxide, at temperatures between 30° and 150° C. to form the pyri(-mi)dyl-oxy- or thio-benzonitriles of the formula (XIII), of the formula (XIII),

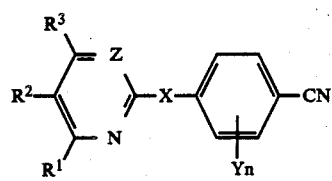
(XIII)

in which $R^1$, $R^2$, $R^3$, Z, X, Y and n have the abovementioned meaning, and these are saponified under acidic or alkaline conditions according to conventional methods, or are reacted with 4-hydroxy- or 4-mercaptobenzoic acid esters of the formula (XIXa),

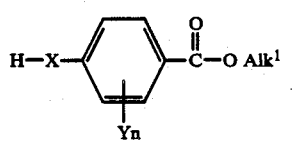
(XIXa)

in which
X, Y and n have the abovementioned meaning and
$Alk^1$ represents alkyl, particularly methyl or ethyl,
if appropriate in the presence of a diluent, such as, for example, sulpholane, and in the presence of an acid binder, such as, for example, potassium hydroxide, at temperatures between 30° and 150° C. to form the pyri(-mi)dyl-oxy- or thiobenzoic acid esters of the formula (Ig)

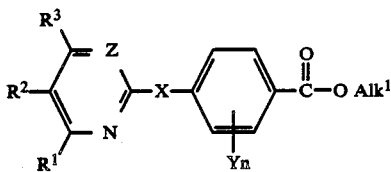

(Ig)

in which $R^1$, $R^2$, $R^3$, Z, X, Y, n and $Alk^1$ have the abovementioned meaning, and these are saponified under alkaline conditions according to conventional methods.

The pyri(mi)dine derivatives of the formula (XVIII) are known or can be prepared in simple fashion according to known methods, for example by reacting 2-hydroxy-pyridines or 2-hydroxypyrimidines of the formula (XXVIIa),

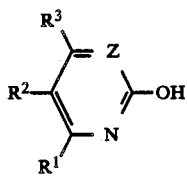

(XXVIIa)

in which $R^1$, $R^2$, $R^3$, and Z have the abovementioned meaning, with inorganic acid halides, such as, for example, phosphoroxy chloride or phosphorus pentachloride, if appropriate in the presence of a diluent, such as, for example toluene of tetrachloromethane, or by reacting 2-aminopyridines or 2-aminopyrimidines of the formula (XXVIIb),

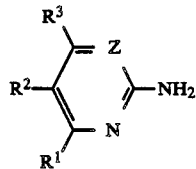

(XXVIIb)

in which $R^1$, $R^2$, $R_3$, and Z have the abovementioned meaning, in a conventional fashion with nitrous acid in the presence of hydrohalic acids.

The 2-hydroxy-pyridines and -pyrimidines of the formula (XXVIIa) and the 2-amino-pyridines and -pyrimidines of the formula (XXVIIb) are generally known compounds of organic chemistry.

Some of the 4-hydroxy- or 4-mercapto-benzonitriles of the formula (XXVI) are known.

Both the known and the unknown 4-hydroxy- or 4-mercapto-benzonitriles of the formula (XXVI) are obtained, for example, by dehydrating 4-hydroxy- or 4-mercapto-benzamides of the formula

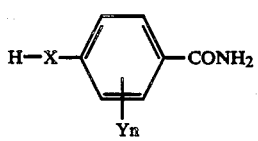

(XXVIa)

in a conventional fashion.

The 4-hydroxy- or 4-mercapto-benzamides of the formula (XXVIa) are known or can be prepared according to known processes.

The 4-hydroxy- or 4-mercaptobenzoic acid esters of the formula (XIXa) are described below in the description of the starting materials for process (B-b$_1$).

The compounds which are furthermore required to carry out the process (A-a$_1$) according to the invention are generally defined by means of the formula (III).

In the formula (III), B and $R^4$ preferably or particularly preferably represent the radicals which have already been mentioned in connection with the description of the substances of the formula (I) according to the invention as being preferred or particularly preferred for these substituents.

The starting compounds of the formula (III) are known compounds, such as, for example, alcohols, phenols, mercaptans, thiophenols, amines or hydroxylamines, or can be prepared according to known methods.

The thiobenzoyl chlorides which are required to carry out the process (A-a$_2$) according to the invention are generally defined by means of the formula (IV).

In the formula (IV), $R^1$, $R^2$, $R^3$, Z, X, Y and n preferably or particularly preferably represent the radicals which have already been mentioned in connection with the description of the substances of the formula (I) according to the invention as being preferable or particularly preferably.

The thiobenzoyl chlorides of the formula (IV) are not yet known. They can be prepared according to known methods, by reacting dithiobenzoic acids of the formula (V)

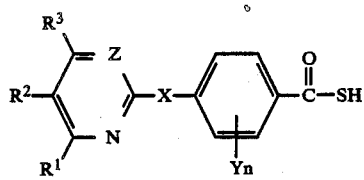

in which $R^1$, $R^2$, $R^3$, Z, X, Y and n have the abovementioned meaning, in a conventional fashion with thionyl chloride or phosgene (cf. Houben-Weyl, Methoden der organischen Chemie [Methods of Organic Chemistry], vol. E5, page 620, Georg Thieme Verlag Stuttgart 1985).

The compounds of the formula (III) which are furthermore required to carry out the process (A-a$_2$) according to the invention have already been described in process (A-a$_1$).

The dithiobenzoic acids which are required to carry out the process (A-a$_3$) according to the invention are generally defined by means of the formula (V).

In the formula (V), $R^1$, $R^2$, $R^3$, Z, X, Y and n preferably or particularly preferably represent the radicals which have already been mentioned in connection with the description of the substances of the formula (I) according to the invention as being preferred or particularly preferred for these substituents.

The dithiobenzoic acids of the formula (V) can be prepared according to known processes (cf. Houben-Weyl, Methoden der organischen Chemie [Methods of Organic Chemistry], vol. IX, page 747, Georg Thieme Verlag Stuttgart 1955) from Grignard compounds of the formula (XXVIII),

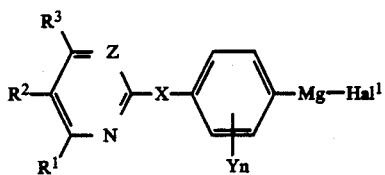

(XXVIII)

in which
R$^1$, R$^2$, R$^3$, Z, X, Y and n have the abovementioned meaning and
Hal$^1$ represents halogen, particularly chlorine or bromine,
by reacting with carbon disulphide in the presence of a diluent, such as, for example, diethyl ether or tetrahydrofuran, at temperatures from −30° C. to +50° C., or dithiobenzoic acids of the formula (V) are obtained when bis-thiobenzoyl disulphides of the formula (XXIX),

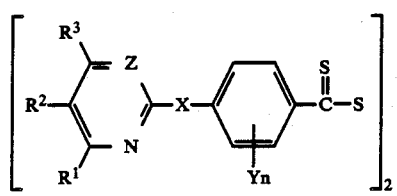

(XXIX)

in which R$^1$, R$^2$, R$^3$, Z, X, Y and n have the abovementioned meaning, are reduced using base metals, such as, for example, zinc or iron, in the presence of mineral acids or alkalis in water or aqueous alcohols at temperatures from 0° to 100° C.

Grignard compounds of the formula (XXVIII) can be prepared according to known methods.

Bis-thiobenzoyl disulphides of the formula (XXIX) are obtained when pyri(mi)dine derivatives of the formula (XVIII),

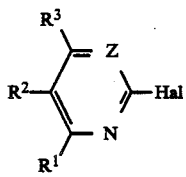

(XVIII)

in which R$^1$, R$^2$, R$^3$, Z and Hal have the abovementioned meaning, are reacted with bis-[4-hydroxy-(4-mercapto)-thiobenzoyl] disulphides of the formula (XXX),

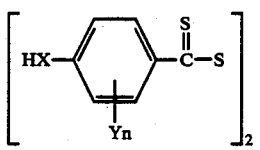

(XXX)

in which X, Y and n have the abovementioned meaning, if appropriate in the presence of a diluent, such as, for example, sulpholane, and in the presence of an acid binder, such as, for example, potassium hydroxide, at temperatures between +30° C. and +130° C.

The compounds of the formula (XXX) are known substances and can be prepared according to known methods (cf. Houben-Weyl, Methoden der organischen Chemie [Methods of Organic Chemistry], vol. IX, page 748 or vol. E5, pages 899 et seq., page 915, Georg Thieme Verlag Stuttgart 1955/1985).

The alkylating agents which are furthermore required to carry out the process (A-a$_3$)/version ($\alpha$) according to the invention are generally defined by means of the formula (VI).

In the formula (VI), R$^{4-1}$ preferably represents C$_1$–C$_{12}$-alkyl or phenyl-C$_1$–C$_5$-alkyl, L preferably represents chlorine, bromine, or iodine, p-toluenesulphonyloxy, methoxysulphonyloxy or ethoxysulphonyloxy. The alkylating agents of the formula (VI) are generally known compounds of organic chemistry.

The olefines which are required to carry out the process (A-a$_3$)/version ($\beta$) according to the invention are generally defined by means of the formula (VII).

In the formula (VI), R$^{16}$, R$^{18}$, R$^{19}$ and R$^{20}$, in each case independently of one another, preferably represent hydrogen, alkyl, having 1 to 10 carbon atoms, which is optionally mono- or poly-substituted, identically or differently, by fluorine, chlorine, bromine, C$_1$–C$_4$-alkoxy or halo-C$_1$–C$_4$-alkyl, cycloalkyl, having 3 to 6 carbon atoms, which is optionally mono- to tri-substituted, identically or differently, by methyl, ethyl, fluorine and chlorine, phenyl which is optionally mono- to penta-substituted, identically or differently, by fluorine, chlorine, bromine, nitro, trifluoromethyl, methyl, ethyl, methoxy or methylthio, nitro, cyano, —COOR$^{13}$, —CONR$^{14}$R$^{15}$, —CSR$^{14}$R$^{15}$, —SO$_2$NR$^{14}$R$^{15}$ or the radical D—R$^9$, where R$^{13}$, R$^{14}$, R$^{15}$, D and R$^9$ preferably have the meaning which has already been mentioned in the description of the substances of the formula (I) according to the invention as being preferable for these substituents, or R$^{16}$ and R$^{20}$ together denote a further C—C bond. The olefines of the formula (VII) are generally known compounds of organic chemistry.

The dithiobenzoic acid derivatives which are required to carry out the process (A-a$_4$)/version ($\alpha$) according to the invention are generally defined by means of the formula (Va). In the formula (Va), R$^1$, R$^2$, R$^3$, Z, X, Y and n preferably represent the radicals which have already been mentioned in connection with the description of the substances of the formula (I) according to the invention as being preferable for these substituents, and R$^{10}$ preferably represents hydrogen or C$_1$–C$_4$-alkyl.

The dithiobenzoic acid derivatives of the formula (Va), in which R$^{10}$ represents alkyl, are compounds according to the invention and can be obtained according to process (A-a$_3$)/version ($\alpha$). Compounds of the formula (Va), in which R$^{10}$ represents hydrogen, correspond to the compounds of the formula (V) and can be obtained according to the process which is described there.

The amines or hydroxylamines which are furthermore required to carry out the process (A-a$_4$)/version ($\alpha$) according to the invention are generally defined by means of the formulae (VIIIa) or (VIIIb). In the formulae (VIIIa) or (VIIIb), R$^4$, R$^7$ and R$^8$ preferably or particularly preferably represent the radicals which have already been mentioned in connection with the description of the substances of the formula (I) according to the invention as being preferable or particularly preferable for these substituents.

The amines or hydroxylamines of the formulae (VIIIa) or (VIIIb) are generally known compounds of organic chemistry.

The benzimide chlorides which are required to carry out the process (A-a4)/version (β) according to the invention are generally defined by means of the formula (IXa). In the formula (IXa), $R^1$, $R^2$, $R^3$, $R^4$, Z, X, Y and n preferably or particularly preferably represent the radicals which have already been mentioned in connection with the description of the substances of the formula (I) according to the invention as being preferable or particularly preferable for these substituents.

The benzimide chlorides of the formula (IXa) are not yet known.

They are obtained when benzamides of the formula (Ih),

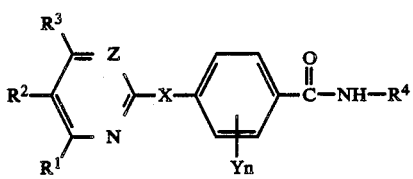

in which $R^1$, $R^2$, $R^3$, $R^4$, Z, X, Y and n have the above-mentioned meaning, are reacted with inorganic acid chlorides, such as, for example, phosphoroxy chloride, phosphorous pentachloride, thionyl chloride or phosgene, in the presence of a diluent, such as, for example, toluene or dichloromethane, at temperatures between 0° and +100° C.

The benzamides of the formula (Ih) are compounds according to the invention and can be obtained according to process (A-a1).

The benzamides which are required as starting meterials to carry out the process (A-a4)/version (υ) according to the invention are generally defined by means of the formula (Ia). In the formula (Ia), $R^1$, $R^2$, $R^3$, $R^4$, Z, X, Y, n and $B^1$ preferably or particularly preferably represent the radicals which have already been mentioned in the description of the substances of the formula (I) according to the invention as being preferable or particularly preferable for these substituents.

The benzamides of the formula (Ia) are compounds according to the invention and can be obtained according to process (A-a1).

Sulphurizing agents are required as starting materials to carry out the process (A-a4)/version (υ) according to the invention. All sulphurizing agents which can conventionally be used for such reactions are suitable, and the decasulphide of phosphorus ($P_4S_{10}$) or 2,4-bis-(4-methoxy-phenyl)-2,4-dithiono-1,3,2,4-dithiadiphosphetane (Lawesson reagent) are preferably used. The sulphurizing agents are generally known componds of inorganic or organic chemistry.

The benzimide chlorides which are required as starting materials to carry out the process (A-a5)/version (α) according to the invention are generally defined by means of the formula (IXb). In the formula (IXb), $R^1$, $R^2$, $R^3$, $R^5$, Z, X, Y and n preferably or particularly preferably represent the radicals which have already been mentioned in connection with the description of the substances of the formula (I) according to the invention as being preferred for these substituents.

The benzimide chlorides of the formula (IXb) are not yet known. They are obtained analogously to the process which has already been described for the preparation of the compounds of the formula (IXa).

The compounds of the formula (III) which are furthermore required as starting materials to carry out the process (A-a5)/version (α) according to the invention have already been described in the description of the preparation process (A-a1).

The thiobenzamides which are required as starting materials to carry out the process (A-a5)/version (β) according to the invention are generally defined by means of the formula (X). In the formula (X), $R^1$, $R^2$, $R^3$, $R^7$, Z, X, Y and n preferably or particularly preferably represent the radicals which have already been mentioned in connection with the description of the substances of the formula (I) according to the invention as being preferred for these substituents.

Thiobenzamides of the formula (X) are obtained when hydrogen sulphide is added in a conventional fashion to pyri(mi)dyl-oxy- or thiobenzonitriles of the formula (XIII),

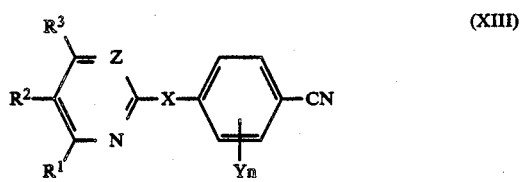

in which $R^1$, $R^2$, $R^3$, Z, X, Y and n have the abovementioned meaning and if appropriate in the presence of a diluent, such as, for example, pyridine, and a base, such as, for example, sodium methylate or sodium ethylate, pyridine or triethylamine.

The preparation of the pyri(mi)dyl-oxy- or -thiobenzonitriles of the formula (XIII) has already been described above in the description of the carboxylic acid derivatives of the formula (XXV).

The alkylating agents which are furthermore required as starting materials to carry out the process (A-a5)/version β according to the invention are generally defined by means of the formula (VI) and have already been described in the description of the process (A-a3)/version α.

The hydroximyl halides which are required as starting materials to carry out the process (A-a6)/version α according to the invention are generally defined by means of the formula (XIa). In the formula (XIa), $R^1$, $R^2$, $R^3$, $R^6$, Z, X, Y and n preferably or particularly preferably represent the radicals which have already been mentioned in connection with the description of the substances of the formula (I) according to the invention as being preferable or particularly preferable for these substituents, and Hal preferably represents chlorine or bromine.

The hydroximyl halides of the formula (XI) are obtained according to known methods, for example by halogenation of the corresponding aldoximes (cf. Houben-Weyl, Methoden der organischen Chemie [Methods of Organic Chemistry], vol. 5/3, page 638 et seq. Georg Thieme Verlag Stuttgart 1962).

The compounds of the formula (III) which are furthermore required as starting materials to carry out the process (A-a6)/version (α) according to the invention have already been described above.

The hydroxamic acids which are furthermore required as starting materials to carry out the process (A-a6)/version β according to the invention are generally defined by means of the formula (XIb). In the formula (XIb), $R^1$, $R^2$, $R^3$, $R^6$, Z, X, Y and n preferably or particularly preferably represent the radicals which have already been mentioned in connection with the description of the substances of the formula (I) according to the invention as being preferable or particularly preferable for these substituents, and $B^2$ represents oxygen or sulphur.

The hydroxamic acids of the formula (XIb) are obtained when either benzoic acid derivatives of the formula (II),

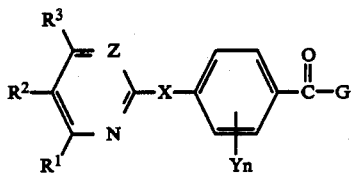

in which $R^1$, $R^2$, $R^3$, Z, X, Y, n and G have the abovementioned meaning, or thiobenzoyl chlorides of the formula (IV),

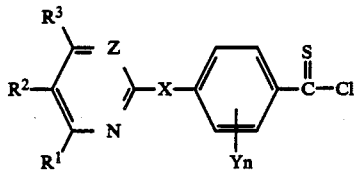

in which $R^1$, $R^2$, $R^3$, Z, X, Y and n have the abovementioned meaning, or dithiobenzoic acids of the formula (V),

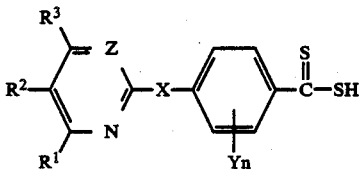

in which $R^1$, $R^2$, $R^3$, Z, X, Y and n have the abovementioned meaning, are reacted with hydroxylamines of the formula (XII).

in which $R^6$ has the abovementioned meaning, if appropriate in the presence of a diluent, such as, for example, toluene, tetrahydrofuran or dioxane, and if appropriate in the presence of an acid binder, such as, for example, triethylamine, at temperatures between 0° and +100° C.

The alkylating agents of the formula (VI) which are furthermore required as starting materials to carry out the process (A-$a_6$)/version β according to the invention have already been described above.

The thiobenzoic acid esters which are required as starting materials to carry out the process (A-$a_6$)/version γ according to the invention are generally defined by means of the formula (Ib). In the formula (Ib), $R^1$, $R^2$, $R^3$, $R^4$, Z, X, Y and n preferably or particularly preferably represent the radicals which have already been mentioned in connection with the description of the substances of the formula (I) according to the invention as being preferable or particularly preferable for these substituents.

The thiobenzoic acid esters of the formula (Ib) are compounds according to the invention and can be obtained according to process (A-$a_2$).

The hydroxylamines which are furthermore required as starting materials to carry out the process (A-$a_6$)/version γ are generally defined by means of the formula (XII). In the formula (XII), $R^6$ preferably represents hydrogen or alkyl having 1 to 4 carbon atoms.

The hydroxylamines of the formula (XII) are generally known compounds of organic chemistry.

The benzonitriles which are required as starting materials to carry out the process (A-$a_7$)/version α according to the invention are generally defined by means of the formula (XIII) and have already been described in the description of the process (A-$a_1$).

The 2- or 3-hydroxyalkylamines which are furthermore required as starting materials to carry out the process (A-$a_7$)/version α according to the invention are generally defined by means of the formula (XIV). In the formula (XIV), $Alk^2$ preferably represents ethanediyl or propanediyl which is optionally mono- to tri-substituted, identically or differently, by methyl, ethyl, methoxy, ethoxy, fluorine or chlorine.

The 2- or 3-hydroxyalkylamines are generally known compounds of organic chemistry.

The thiobenzamides which are required as starting materials to carry out the process (A-$a_7$)/version β according to the invention are generally defined by means of the formula (Xa). In the formula (Xa), $R^1$, $R^2$, $R^3$, Z, X, Y and n preferably or particularly preferably represent the radicals which have already been mentioned in connection with the description of the substances of the formula (I) according to the invention as being preferable or particularly preferable for these substituents.

The thiobenzamides of the formula (Xa) have already been described in the description of the thiobenzamides of the formula (X) in process (A-$a_5$)/version (β).

The α-halocarbonyl derivatives which are furthermore required as starting materials to carry out the process (A-$a_7$)/version β according to the invention are generally defined by means of the formula (XV). In the formula (XV), $R^{21}$ and $R^{22}$, independently of one another, preferably represent hydrogen, $C_1$–$C_6$-alkyl or phenyl which is optionally mono- to tri-substituted, identically or differently, by fluorine, chlorine, bromine, methyl, ethyl, methoxy, ethoxy or trifluoromethyl, and Hal represents chlorine or bromine.

The hydroxamic acids which are required as starting materials to carry out the process (A-$a_7$)/version γ according to the invention are generally defined by means of the formula (XIb-1). In the formula (XIb-1), $R^1$, $R^2$, $R^3$, Z, X, Y and n preferably or particularly preferably represent the radicals which have already been mentioned in connection with the description of the substances of the formula (I) according to the invention as being preferable or particularly preferable for these substituents.

The hydroxamic acids of the formula (XIb-1) have already been described above in the description of the compounds of the formula (XIb) (process A-$a_6$)/version γ.

The bifunctional alkylating agents which are furthermore required as starting materials to carry out the process (A-$a_7$)/version γ according to the invention are generally defined by means of the formula (VIa). In the formula (VIa), $Alk^2$ preferably represents in each case ethanediyl or propanediyl which are each optionally substituted by methyl, ethyl, cyclopentyl, cyclohexyl or phenyl which is optionally substituted by fluorine, chlorine, methyl, methoxy or trifluoromethyl, and $L^1$ and $L^2$ represent chlorine or bromine.

The bifunctional alkylating agents of the formula (VIa) are generally known compounds of organic chemistry.

The benzamide oximes which are required as starting materials to carry out the process (A-a$_7$)/version δ according to the invention are generally defined by means of the formula (XVI). In the formula (XVI), $R^1$, $R^2$, $R^3$, Z, X, Y and n preferably or particularly preferably represent the radicals which have already been mentioned in connection with the description of the substances of the formula (I) according to the invention as being preferred or particularly preferred for these substituents.

The benzamide oximes of the formula (XVI) are obtained when, for example, benzonitriles of the formula (XIII),

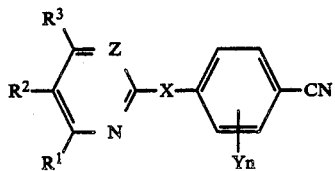

in which $R^1$, $R^2$, $R^3$, Z, X, Y and n have the abovementioned meaning, are reacted with hydroxylamine in conventional fashion, if appropriate in the presence of diluents, such as, for example, ethanol, at temperatures between 0° and +100° C., or when hydroximyl chlorides of the formula (XIa-1),

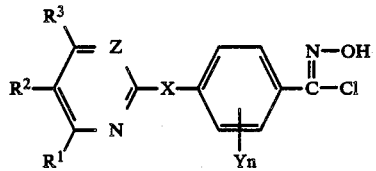

in which $R^1$, $R^2$, $R^3$, Z, X, Y and n have the abovementioned meaning, are reacted with ammonia in a conventional fashion, if appropriate in the presence of an inert diluent, such as, for example, tetrahydrofuran, at temperatures between 0° and +100° C. (cf. Houben-Weyl, Methoden der organischen Chemie [Methods of Organic Chemistry], vol. X/4, page 211, Georg Thieme Verlag Stuttgart 1968).

The benzonitriles of the formula (XIII) and the hydroximyl chlorides of the formula (XIa-1) have already been described above.

The acylating agents which are furthermore required to carry out the process (A-a$_7$)/version δ according to the invention are generally defined by means of the formula (XVII). In the formula (XVII), $R^{4-2}$ preferably represents $C_1$–$C_{10}$-alkyl which is optionally substituted by halogen or the radical —D—$R^9$ (meaning for D and $R^9$ as above), $C_3$–$C_6$-cycloalkyl or phenyl which is optionally substituted by fluorine, chlorine, nitro, trifluoromethyl, methyl, ethyl or methoxy.

The pyri(mi)dine derivatives which are required as starting materials to carry out the process (B-b$_1$) according to the invention are generally defined by means of the formula (XVIII). In the formula (XVIII), $R^1$, $R^2$, $R^3$ and Z preferably or particularly preferably represent the radicals which have already been mentioned in connection with the description of the substances of the formula (I) according to the invention as being preferred or particularly preferred for these substituents.

The following compounds may particularly be mentioned as examples of these substances:
2-chloro-4-methyl-pyridine
2-chloro-6-methyl-pyridine
2-chloro-4,6-dimethyl-pyridine
2-chloro-4-methyl-pyrimidine
2-chloro-4-ethyl-pyrimidine
2-chloro-5-methyl-pyrimidine
2-chloro-5-ethyl-pyrimidine
2-chloro-5-propyl-pyrimidine
2-chloro-5-isopropyl-pyrimidine
2,4-dichloro-6-methyl-pyrimidine
2-chloro-4-methoxy-6-methyl-pyrimidine
2-chloro-4-amino-6-methyl-pyrimidine
2-chloro-4-methylamino-6-methyl-pyrimidine
2-chloro-4-dimethylamino-6-methyl-pyrimidine
2-chloro-4,5-dimethyl-pyrimidine
2-chloro-4-methyl-5-ethyl-pyrimidine
2-chloro-4-ethyl-5-methyl-pyrimidine
2-chloro-4,6-dimethyl-pyrimidine
2-chloro-4-methyl-6-trifluoromethyl-pyrimidine
2-chloro-4-methyl-6-ethyl-pyrimidine
2,5-dichloro-4,6-dimethyl-pyrimidine
2-chloro-5-bromo-4,6-dimethyl-pyrimidine
2,5-dichloro-4-methoxy-6-methyl-pyrimidine
2,5-dichloro-4-methylmercapto-6-methyl-pyrimidine
2-chloro-4,5,6-trimethyl-pyrimidine
2-chloro-5-ethyl-4,6-dimethyl-pyrimidine
2-chloro-4,5-cyclopenteno-pyrimidine
2-chloro-4,5-cyclopenteno-6-methyl-pyrimidine
2-chloro-4,5-cyclohexeno-pyrimidine
2-chloro-4,5-cyclohexeno-6-methyl-pyrimidine
2-chloro-quinazoline
2,6-dichloroquinazoline
2-chloro-4-methyl-quinazoline The pyri(mi)dine derivatives of the formula (XVIII) have already been described above in the description of the process (A-a$_1$).

The 4-hydroxy- or 4-mercapto-benzoic acid derivatives which are furthermore required as starting materials to carry out the process (B-b$_1$) according to the invention are generally defined by means of the formula (XIX). In the formula (XIX), X, Y, n, A, B and $R^4$ preferably or particularly preferably represent the radicals which have already been mentioned in connection with the description of the substances of the formula (I) according to the invention as being preferred or particularly preferred.

Some of the 4-hydroxy- or 4-mercapto-benzoic acid derivatives of the formula (XIX) are known.

Both the known and the unknown compounds of the formula (XIX) are obtained according to known methods. Thus, 4-hydroxy- and 4-mercaptobenzoic acid esters are obtained by esterification of the corresponding free acids using alcohols in the presence of strong acids according to conventional methods, cf., for example, process (A-a$_3$)/version (α); corresponding amides are obtained from the acids by reaction with amines, such as, for example, amines of the formula (VIIIa) or hydroxylamines of the formula (VIIIb), in the presence of dehydrating agents, such as, for example, phosphorus-(III) chloride,, and if appropriate in the presence of diluents at temperatures between 0° and +100° C.; and 4-hydroxy-dithiobenzoic acid esters are obtained by reaction of phenols with carbon disulphide in the presence of strong alkalis, such as, for example, sodium hydroxide or potassium hydroxide, and subsequent S-alkylation using the abovementioned alkylating agents according to the reaction conditions mentioned in process (A-$a_3$)/version ($a$). 4-Mercaptobenzoic acid derivatives can be prepared from appropriate 4-amino-benzoic acid derivatives by diazotization using nitrous acid, reaction with sodium disulphide and subsequent reduction of the disulphides which are produced, for example using zinc in an acidic medium, in a conventional fashion at temperatures between 0° and +100° C.

The 2-mercapto-pyri(mi)dines which are required as starting materials to carry out the process (B-$b_2$) according to the invention are generally defined by means of the formula (XX). In the formula (XX), $R^1$, $R^2$, $R^3$ and Z preferavly or particularly preferably represent the radicals which have already been mentioned in connection with the description of the substances of the formula (I) according to the invention as being preferred or particularly preferred.

The 2-mercapto-pyri(mi)dines of the formula (XX) are known or can be prepared according to known methods, for example by reacting $\beta$-dicarbonyl compounds with thioureas, 2-hydroxy-pyri(mi)dines with phosphorus-V sulphide or reacting the Lawesson reagent or 2-halo-pyri(mi)dines with metal salts of hydrogen sulphide, such as, for example, sodium sulphide, in a conventional fashion.

The compounds which are furthermore required as starting materials to carry out the process (B-$b_2$) according to the invention are generally defined by means of the formula (XXI). In the formula (XXI), A, B, $R^4$, Y and n preferably or particularly preferably represent the radicals which have already been mentioned in connection with the description of the substances of the formula (I) according to the invention as being preferred or particularly preferred for these substituents, and Hal represents chlorine or bromine and m preferably represents 1, 2 or 3.

The 4-halo-benzoic acid derivatives of the formula (XXI) are known or can be prepared according to known methods, for example from the free acids or from the corresponding acid halides by reaction with the desired nucleophiles, cf. the methods specified in the description of the compounds of the formula (XIX).

The reactions according to the process (B-$b_2$) here only proceed in a desired fashion when the halogen in the compounds of the formula (XXI) is activated by additional electron-withdrawing substituents in the aromatic radical. Suitable substituents for such activation are particularly fluorine, chlorine, bromine, nitro, cyano or trifluoromethyl.

Particularly suitable reaction components of the formula (XXI) for the process (B-$b_2$) are the following compounds:
3,4,5-trichloro-benzoic acid
3,5-dichloro-4-fluoro-benzoic acid
pentachlorobenzoic acid
3-nitro-4-chloro-benzoic acid
3,5-dinitro-4-chloro-benzoic acid
3-cyano-4-chloro-benzoic acid
4-chloro-3-trifluoromethyl-benzoic acid The compounds which are required as starting materials to carry out the process (C-$c_1$) to (C-$c_4$) according to the invention are generally defined by means of the formula (I), they are compounds according to the invention and can be obtained according to the preparation processes described above.

The halogenating agents which are furthermore required as starting materials to carry out the process (C-$c_1$) according to the invention are generally known compounds of organic chemistry. Preferably, chlorine or bromine in elementary form are used. If appropriate, the process according to the invention is carried out in the presence of a catalyst. All catalysts which are conventionally used for such aromatic electrophilic substituents, such as Lewis acids (aluminum-II chloride), can be employed as catalysts.

The reducing agents which are furthermore required as starting materials to carry out the process (C-$c_2$) according to the invention are generally known compounds. Preferably, metals, such as iron, zinc or tin, or metal salts, such as iron-II salts or tin-II salts, particularly the chlorides, or compounds of sulphur, such as sulphides, sulphites or dithionites, are used.

The acid chlorides which are furthermore required as starting materials to carry out the process (C-$c_3$) according to the invention are generally defined by means of the formula (XXII). In the formula (XXII), $R^{23}$ preferably represents methyl, ethyl, methoxy, ethoxy, dimethylamino, diethylamino or methylethylamino. The compounds of the formula (XXII) are generally known compounds of organic chemistry.

The nitrous acid or alkyl nitrites, particularly methyl nitrite or ethyl nitrite, which are furthermore required as starting materials to carry out the process (C-$c_4$) according to the invention are generally known compounds.

Particularly preferably, the following substituents are converted to one another by means of process (C): hydrogen to chlorine or bromine; nitro to amino; amino to chlorine, bromine or cyano and amino to methylcarbonylamino or ethylcarbonylamino.

The compounds of the formula (I), in which $R^3$ denotes fluorine, chlorine or bromine and which are required as starting materials to carry out the process (D) according to the invention are generally defined by means of the formula (If). The compounds of the formula (If) are compounds according to the invention and can be obtained according to processes A to C. In the formula (If), $R^1$, $R^2$, $R^4$, Z, X, A, B, Y and n preferably or particularly preferably represent the radicals which have already been mentioned in connection with the description of the substances according to the invention as being preferred ior particularly preferred.

$R^{3-1}$ preferably represents methoxy, ethoxy, amino, methylamino, ethylamino, dimethylamino or ethylamino.

The alcohols or primary and secondary amines which are furthermore required as starting materials to carry out the process (D) according to the invention are generally defined by means of the formula (XXIII) or (XXIV). In the formula (XXIII), $R^{24}$ preferably represents methyl or ethyl, in the formula (XXIV), $R^{25}$ and $R^{26}$, independently of one another, preferably represent hydrogen, methyl or ethyl.

The alcohols of the formula (XXIII), the primary and secondary amines of the formula (XXIV) and ammonia are generally known compounds or organic chemistry.

Suitable diluents to carry out the process (A-$a_1$) according to the invention are inert organic solvents.

Preferably, hydrocarbons, such as benzine, benzene, toluene, xylene and tetraline, furthermore halohydrocarbons, such as methylene chloride, chloroform, carbon tetrachloride, chlorobenzene and o-dichlorobenzene, in addition ketones, such as acetone and methyl isopropyl ketone, moreover ethers, such as diethyl ether, tetrahydrofuran and dioxane, additionally carboxylic acid esters, such as ethyl acetate, and also very polar solvents, such as dimethyl sulphoxide and sulpholane, are used.

In the case where G in the formula (II) represents halogen and where the stability to hydrolysis of the acid halide allows it, the reaction can also be carried out in the presence of water.

If alcohols or amines in liquid form are used as reaction component of the formula (III), then these can, particularly advantageously, be employed simultaneously as diluents in appropriate excess.

The process (A-$a_1$) according to the invention is, if appropriate, carried out in the presence of an acid binder. As such, all conventional inorganic or organic bases are suitable. Preferably, tertiary amines, such as triethylamine, pyridine and N,N-dimethyl-aniline, furthermore alkaline earth metal oxides, such as magnesium oxide and calcium oxide, in addition alkali metal and alkaline earth metal carbonates, such as sodium carbonate, potassium carbonate and calcium carbonate, are used. However, alcohols, phenols, mercaptans and thiophenols can also be employed in the form of their previously prepared metal compounds. If the reaction component of the formula (III) has basic properties (B represents —N—$R^7$ or —N—$OR^8$), then this can also be employed as an acid binder in appropriate excess.

This reaction temperatures can be varied within a relatively wide range when the process (A-$a_1$) according to the invention is carried out. If the process is carried out without solvent and acid binder, then the components are in general initially allowed to react at temperatures between −20° C. and +20° C. and then heated to temperatures between 70° and 200° C. If the process is carried out in the presence of a diluent and an acid binder, then the reaction temperatures, in general, are between −20° C. and +100° C., preferably between 0° C. and 50° C.

The process according to the invention is, in general, carried out under standard pressure.

To carry out the process (A-$a_1$) according to the invention, 1.0 to 5.0 moles, preferably 1.0 to 2.0 moles, of compound of the formula (III) and, if appropriate, 1.0 to 3.0, preferably 1.0 to 2.0, moles of acid binder are, in general, employed per mole of benzoic acid derivative of the formula (II).

On carrying out the process (A-$a_1$) according to the invention, it is possible to do without previous preparation of the benzoyl halides (in the formula (III), G represents halogen) and to react the free acids with the compounds of the formula (III) in the presence of a water-binding agent, such as, for example, the inorganic acid halides, such as phosphorus trichloride or phosphoroxy chloride, which can be used for the preparation of the benzoyl halides.

The work-up occurs according to conventional methods. In general, in the preparation process according to the invention, the precipitated salts are removed and the reaction mixture which remains is concentrated by stripping off the diluent. If the process is carried out in the presence of water or water-miscible solvents, then the reaction mixture can be diluted with water, the mixture which results filtered off under suction or extracted with an organic solvent which is slightly miscible with water, the organic layer is washed, concentrated and the residue remaining, if appropriate, subjected to conventional purification processes.

Inert organic solvents or polar solvents are also suitable as diluents for carrying out the preparation process (A-$a_2$). Preferably, the solvents which are mentioned in the preparation process (A-$a_1$) are used.

All organic or inorganic bases which can conventionally be used are suitable as acid binder for carrying out the preparation process (A-$a_2$). Preferably, the bases mentioned for process (A-$a_1$) are used.

The reaction temperatures can be varied within a relatively wide range in the preparation process (A-$a_2$). In general, the process is carried out at temperatures between −20° C. and +100° C., preferably between 0° C. and 50° C.

The process (A-$a_2$) according to the invention is, in general, carried out at standard pressure.

To carry out the process (A-$a_2$) according to the invention, 1.0 to 5.0 moles, preferably 1.0 to 2.0 moles, of compound of the formula (III) and 1.0 to 5.0 moles, preferably 1.0 to 2.0 moles, of acid binder are, in general, employed per mole of thiobenzoyl chloride of the formula (IV). The reaction is carried out and the reaction products of the formula (I) are worked up and isolated in a generally conventional fashion (cf. Houben-Weyl, Methoden der organischen Chemie [Methods of Organic Chemistry], vol. E5, pages 792, 907, 1246, Georg Thieme Verlag Stuttgart 1985).

Inert organic solvents are suitable as diluent for carrying out the processes (A-$a_3$)/versions ($\alpha$) and ($\beta$) according to the invention.

To these belong particularly aliphatic or aromatic, if appropriate halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethyl acatamide, N-methylformanilide, N-methylpyrrolidone or hexamethylphosphoric acid triamide, esters, such as ethyl acetate, sulphoxides or sulphones, such as dimethyl sulphoxide or sulpholane, or alcohols, such as methanol, ethanol or propanol.

All conventional inorganic or organic bases are suitable as acid binder for carrying out the process (A-$a_3$)/version ($\alpha$) according to the invention. Preferably, tertiary amines, such as triethylamine, pyridine or N,N-dimethylaniline, alkaline earth metal oxides, such as magnesium oxide and calcium oxide, alkali metal and alkaline earth metal carbonates such as sodium carbonate, potassium carbonate or calcium carbonate, such as sodium carbonate, potassium carbonate or calcium carbonate, alkali metal hydroxides, alkali metal hydrides or alkali metal alcoholates, such as sodium hydroxide or potassium hydroxide, sodium hydride, sodium methylate or potassium t-butylate, are used.

The process (A-$a_3$)/version ($\beta$) according to the invention is, if appropriate, carried out in the presence of a catalyst. Preferably, bases, such as sodium amide, alkali metal alcoholate, such as sodium methylate or potassium methylate, or an amine, such as pyridine, piperidine or triethylamine, are used.

The reaction temperatures can be varied within a relatively wide range when the processes (A-$a_3$)/version ($\alpha$) and ($\beta$) according to the invention are carried out. In general, the processes are carried out at temperatures between 0° C. and 100° C., preferably between 20° C. and 80° C.

The processes (A-a$_3$)/version ($\alpha$) and ($\beta$) according to the invention are, in general, carried out at standard pressure. Gaseous reaction components are preferably used in a closed vessel.

To carry out the process (A-a$_3$)/version ($\alpha$) according to the invention, 1.0 to 5.0 moles, preferably 1.0 to 3.0 moles, of alkylating agent of the formula (VI) and, if appropriate, 1.0 to 5.0 moles, preferably 1.0 to 3.0 moles, of acid binder are employed per mole of dithiobenzoic acid of the formula (V).

To carry out the process (A-a$_3$)/version ($\beta$) according to the invention, 1.0 to 5.0 moles, preferably 1.0 to 3.0 moles, of olefine of the formula (VII) and, if appropriate, up to 1 mole, preferably 0.01 to 0.2 mole, of catalyst are employed per mole of dithiobenzoic acid of the formula (V).

The reaction and the work-up in the process (A-a$_3$)/version ($\alpha$) and ($\beta$) according to the invention are carried out according to known methods (cf. Houben-Weyl, Methoden der organischen Chemie [Methods of Organic Chemistry], vol. IX, page 760 and vol. E/5, pages 907 and 908, Georg Thieme Verlag Stuttgart 1955/1985).

Inert organic solvents are suitable as diluent for carrying out the process (A-a$_4$)/version ($\alpha$) and ($\beta$) according to the invention.

To these belong in particular aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethyl acetamide, N-methylformanilide, N-methylpyrrolidone or hexamethylphosphoric acid triamide, esters, such as ethyl acetate sulphoxides or sulphones, such as dimethyl sulphoxide or sulpholane or alcohols, such as methanol, ethanol or propanol.

The reaction temperatures can be varied within a relatively wide range when the process (A-a$_4$)/version ($\alpha$) according to the invention is carried out. In general, the process is carried out at temperatures between 0° C. and 100° C., preferably between 20° and 75° C.

The process (A-a$_4$)/version ($\alpha$) according to the invention is, in general, carried out under standard pressure.

To carry out the process (A-a$_4$)/version ($\alpha$) according to the invention, 1.0 to 5.0 moles, preferably 1.0 to 2.0 moles, of amine of the formula (VIIIa) or hydroxylamine of the formula (VIIIb) are employed per mole of dithiobenzoic acid derivative of the formula (Va).

The reaction temperature can be varied within a relatively wide range when the process (A-a$_4$)/version ($\beta$) according to the invention is carried out. In general, the process is carried out at temperatures between 0° C. and 100° C., preferably between +10° C. and +50° C. The process (A-a$_4$)/version ($\beta$) according to the invention is, in general, carried out under standard pressure.

To carry out the process (A-a$_4$)/version ($\beta$) according to the invention, 1.0 to 5.0 moles, preferably 1.0 to 2.0 moles, of hydrogen sulphide or its salts are employed per mole of benzimide chloride of the formula (IXa).

Inert organic solvents are suitable as diluent for carrying out the process (A-a$_4$) version ($\gamma$) according to the invention. Preferably toluene, xylene or benzene are used as diluents.

The reaction temperatures can be varied within a relatively wide range when the process (A-a$_4$)/version (-) according to the invention is carried out. In general, the process is carried out at temperatures between +20° C. and +150° C., preferably between +50° C. and +120° C.

The process (A-a$_4$)/version ($\gamma$) according to the invention is, in general, carried out under standard pressure.

To carry out the process (A-a$_4$)/version ($\gamma$) according to the invention, 1.0 to 5.0 moles, preferably 1.0 to 2.0 moles, of sulphurizing agents are employed per mole of benzamide of the formula (Ia).

The reaction is carried out and the products worked up according to known methods for processes (A-a$_4$)/version ($\alpha$), ($\beta$) and ($\gamma$) according to the invention (cf. Houben-Weyl, Methoden der organischen Chemie [Methods of Organic Chemistry], vol. E/5, pages 1249/1250, page 1251, pages 1243–1245, Georg Thieme Verlag Stuttgart 1985).

Inert organic solvents are suitable as diluents for carrying out the process (A-a$_5$)/version ($\alpha$) according to the invention. Preferably, the solvents mentioned for process (A-a$_1$) are used.

All conventional inorganic or organic bases are suitable as acid binder for carrying out the process (A-a$_5$)/version ($\alpha$) according to the invention. Preferably, the acid binders mentioned for process (A-a$_1$) are used.

The reaction temperatures can be varied within a relatively wide range when the process (A-a$_5$)/version ($\alpha$) according to the invention is carried out. In general, the process is carried out at temperatures between −20° C. and +100° C., preferably between 0° C. and +50° C.

The process (A-a$_5$)/version ($\alpha$) according to the invention is, in general, carried out under standard pressure.

To carry out the process (A-a$_5$)/version ($\alpha$) according to the invention, 1.0 to 5.0 moles, preferably 1.0 to 3.0 moles, of compound of the formula (III) and 1.0 to 5.0 moles, preferably 1.0 to 3.0 moles, of acid binder are employed per mole of benzimide chloride of the formula (IXb).

Inert organic solvents are suitable as diluent for carrying out the process (A-a$_5$)/version ($\beta$) according to the invention. Preferably, the solvents mentioned for process (A-a$_3$)/version ($\alpha$) are used.

All conventional inorganic or organic bases are suitable as acid binder for carrying out the process (A-a$_5$)/version ($\beta$) according to the invention. Preferably, the acid binders mentioned for process (A-a$_3$)/version ($\alpha$) are used.

If the process (A-a$_5$)/version ($\beta$) according to the invention is carried out in the absence of an acid binder, then the salts of the amino-thioesters with the anion L$^\ominus$ are obtained initially, from which the free compounds are obtained by addition of base.

The reaction temperatures can be varied within a relatively wide range when the process (A-a$_5$)/version ($\beta$) according to the invention is carried out. In general, the process is carried out at temperatures between 0° C. and 200° C., preferably between 20° C. and +180° C.

The process (A-a$_5$)/version ($\beta$) according to the invention is, in general, carried out under standard pressure.

To carry out the process (A-a$_5$)/version ($\beta$) according to the invention, 1.0 to 5.0 moles, preferably 1.0 to 3.0 moles, of alkylating agent of the formula (VI) and, if appropriate, 1.0 to 5.0 moles, preferably 1.0 to 3.0 moles, of acid binder are employed per mole of thiobenzamide of the formula (X).

Inert organic solvents are suitable as diluent for carrying out the process (A-a$_6$)/version ($\alpha$) according to the invention. Preferably, the solvents mentioned for process (A-a$_1$) are used.

All conventional inorganic or organic bases are suitable as acid binder for carrying out the process (A-a$_6$)/version ($\alpha$) according to the invention. Preferably, the acid binders mentioned for process (A-a$_1$) are used.

The reaction temperatures can be varied within a relatively wide range when the process (A-a$_6$)/version ($\alpha$) according to the invention is carried out. In general, the process is carried out at temperatures between $-20°$ C. and $+100°$ C., preferably between $0°$ C. and $+75°$ C.

The process (A-a$_6$)/version ($\alpha$) according to the invention is, in general, carried out under standard pressure.

To carry out the process (A-a$_6$)/version ($\alpha$) according to the invention, 1.0 to 5.0 moles, preferably 1.0 to 3.0 moles, of compound of the formula (III) and 1.0 to 5.0 moles, preferably 1.0 to 3.0 moles, of acid binder are employed per mole of hydroximyl halide of the formula (XIa).

The reaction is carried out and the product worked up according to known methods for the process (A-a$_6$)/version $\alpha$ according to the invention (cf. Houben-Weyl, Methoden der organischen Chemie [Methods of Organic Chemistry], vol. X/3, page 868, vol. X/4, pages 209 et seq. and vol. E/5, pages 828 and 1280, Georg Thieme Verlag Stuttgart 1965/1968/1985).

Inert organic solvents are suitable as diluent for carrying out the process (A-a$_6$)/version ($\beta$) according to the invention. Preferably, the solvents mentioned for process (A-a$_3$)/version ($\beta$) are used.

All conventional inorganic or organic bases are suitable as acid binder for carrying out the process (A-a$_6$)/version ($\beta$) according to the invention. Preferably the acid binders mentioned for process (A-a$_3$)/version ($\alpha$) are used. The reaction temperatures can be varied within a relatively wide range when the process (A-a$_6$)/version ($\beta$) according to the invention is carried out. In general, the process is carried out at temperatures between $+20°$ C. and $+200°$ C., preferably between $+50°$ C. and $+150°$ C.

The process (A-a$_6$)/version ($\beta$) according to the invention is, in general, carried out under standard pressure.

To carry out the process (A-a$_6$)/version ($\beta$) according to the invention, 1.0 to 5.0 moles, preferably 1.0 to 3.0 moles, of alkylating agent of the formula (VI) and, if appropriate, 1.0 to 5.0 moles, preferably 1.0 to 3.0 moles, of acid binder are employed per mole of hydroxamic acid of the formula (XIb).

The reaction is carried out and the product worked up according to known methods for the process (A-a$_6$)/version ($\beta$) according to the invention (cf. Houben-Weyl, Methoden der organischen Chemie [Methods of Organic Chemistry], vol. E/5, pages 827 and 1287, Georg Thieme Verlag Stuttgart 1985).

Inert organic solvents are suitable as diluent for carrying out the process (A-a$_6$)/version ($\gamma$) according to the invention.

To these belong particularly aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethyl acetamide, N-methylformanilide, N-methylpyrrolidone or hexamethylphosphoric acid triamide, esters, such as ethyl acetate, sulphoxides or sulphones, such as dimethyl sulphoxide or sulpholane, or alcohols, such as methanol, ethanol or propanol.

The reaction temperatures can be varied within a relatively wide range in the process (A-a$_6$)/version ($\gamma$) according to the invention. In general, the process is carried out at temperatures between $+30°$ C. and $+200°$ C., preferably between $+50°$ C. and $+120°$ C.

The process (A-a$_6$)/version ($\gamma$) according to the invention is, in general, carried out under standard pressure.

To carry out the process according to the invention, 1.0 to 5.0 moles, preferably 1.0 to 3.0 moles, of hydroxylamine of the formula (XII) are employed per mole of thiobenzoic acid ester of the formula (Ib).

The reaction is carried out and the product worked up according to known methods for the process (A-a$_6$)/version ($\gamma$) according to the invention (cf. Houben-Weyl, Methoden der organischen Chemie [Methods of Organic Chemistry], vol. E/5, pages 826 and 829, Georg Thieme Verlag Stuttgart 1985).

Inert organic solvents are suitable as diluents for carrying out the process (A-a$_7$)/version ($\alpha$) according to the invention. Preferably, the solvents mentioned for process (A-a$_7$)/version ($\beta$) are used.

The process (A-a$_7$)/version ($\alpha$) according to the invention is carried out in the presence of a catalyst. Preferably, metal salts, such as cadmium acetate, zinc chloride or zinc acetate, are used.

The reaction temperatures can be varied within a relatively wide range when the process (A-a$_7$)/version ($\alpha$) according to the invention is carried out. In general, the process is carried out at temperatures between $25°$ C. and $200°$ C., preferably between $50°$ C. and $150°$ C.

The process (A-a$_7$)/version ($\alpha$) according to the invention is, in general, carried out under standard pressure.

To carry out the process (A-a$_7$)/version ($\alpha$) according to the invention, 1.0 to 5.0 moles, preferably 1.0 to 3.0 moles, of 2- or 3-hydroxyalkylamine of the formula (XVII) and, 0.01 to 0.5 moles, preferably 0.05 to 0.3 moles, of catalyst are employed per mole of benzonitrile of the formula (XVI).

The reaction of the process (A-a$_7$)/version ($\alpha$) according to the invention is carried out according to known methods (cf. Angewandte Chemie 84, 343 (1972)).

Inert organic solvents are suitable as diluents for carrying out the process (A-a$_7$)/version ($\beta$) according to the invention. To these belong particularly aliphatic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones, such as acetone or butanone, nitriles, such as acetonitrile or propionitrile, amides, such as dimethylformamide, dimethyl acetamide, N-methylformanilide, N-methylpyrrolidone or hexamethylphosphoric acid triamide, esters, such as ethyl acetate, sulphoxides or sulphones, such as dimethyl sulphoxide or sulpholane, or alcohols, such as methanol, ethanol or propanol.

All conventional inorganic or organic bases are suitable as acid binder for carrying out the process (A-$a_7$)/version ($\beta$) according to the invention. Preferably, tertiary amines, such as triethylamine, pyridine, N,N-dimethylaniline, alkaline earth metal oxides, such as magnesium oxide and calcium oxide, alkali metal and alkaline earth metal carbonates, such as sodium carbonate, potassium carbonate or calcium carbonate, alkali metal hydroxides, alkali metal hydrides or alkali metal alcoholates, such as sodium hydroxide or potassium hydroxide, sodium hydride, sodium methylate or sodium t-butylate, are used.

The reaction temperatures can be varied within a relatively wide range when the process (A-$a_7$)/version ($\beta$) according to the invention is carried out. In general, the process is carried out at temperatures between 0° C. and 150° C., preferably between 20° C. and 120° C.

The process (A-$a_7$)/version ($\beta$) according to the invention is, in general, carried out under standard pressure.

To carry out the process (A-$a_7$)/version ($\beta$) according to the invention, 1.0 to 5.0 moles, preferably 1.0 to 3.0 moles, of $\alpha$-halocaronyl derivative of the formula (XV) and 1.0 to 5.0 moles, preferably 1.0 to 3.0 moles, of acid binder are employed per mole of thiobenzamide of the formula (Xa).

Inert organic solvents are suitable as diluent for carrying out the process (A-$a_7$)/version ($\gamma$) according to the invention. Preferably, the diluents mentioned for process (A-$a_6$)/version ($\beta$) are used.

All conventional inorganic or organic bases are suitable as acid binder for carrying out the process (A-$a_7$)/version ($\gamma$) according to the invention. Preferably, the acid binders mentioned for process (A-$a_6$)/version ($\beta$) are used.

The reaction temperatures can be varied within a relatively wide range when the process (A-$a_7$)/version ($\gamma$) according to the invention is carried out. In general, the process is carried out at temperatures between 30° C. and 200° C., preferably between 50° C. and 150° C.

The process (A-$a_7$)/version ($\gamma$) according to the invention is, in general, carried out under standard pressure.

To carry out the process (A-$a_7$)/version ($\delta$) according to the invention 1.0 to 5.0 moles, preferably 1.0 to 3.0 moles, of bifunctional alkylating agent of the formula (VIa) and 1.0 to 10.0 moles, preferably 1.0 to 6.0 moles, of acid binder are employed per mole of hydroxamic acid of the formula (XIb-1).

Inert organic solvents are suitable as diluent for carrying out the process (A-$a_7$)/version ($\delta$) according to the invention. Preferably, those mentioned for process (A-$a_7$)/version ($\beta$) are used.

All conventional inorganic or organic bases are suitable as acid binder for carrying out the process (A-$a_7$)/version ($\delta$) according to the invention. Preferably, tertiary amines, such as triethylamine, pyridine or N,N-dimethylaniline, alkaline earth metal oxides, such as magnesium oxide and calcium oxide, alkali metal carbonates and alkaline earth metal carbonates, such as sodium carbonate, potassium carbonate or calcium carbonate, alkali metal hydroxides, alkali metal hydrides or alkali metal alcoholates, such as sodium hydroxide or potassium hydroxide, sodium hydride, sodium methylate or potassium t-butylate, are used.

The reaction temperatures can be varied within a relatively wide range when the process (A-$a_7$)/version ($\delta$) according to the invention is carried out. In general, the process is carried out at temperatures between 0° C. and +200° C., preferably between +20° C. and +150° C.

The process (A-$a_7$)/version ($\delta$) according to the invention is, in general, carried out under standard pressure.

To carry out the process (A-$a_7$)/version ($\delta$) according to the invention, 1.0 to 5.0 moles, preferably 1.0 to 3.0 moles, of acylating agent of the formula (XIV) and, if appropriate, 1.0 to 5.0 moles, preferably 1.0 to 3.0 moles, of dehydrating agent are employed per mole of benzamide oxime of the formula (XIII).

A detailed description of the reaction conditions for process (A-$a_7$)/version ($\delta$) can be found in A. Weissberger, The Chemistry of Heterocyclic Compounds vol. 17, pages 245 et seq., Interscience Publisher (1962).

All conventional inert organic solvents are suitable as diluent for carrying out the process (B-$b_1$) according to the invention. Preferably, hydrocarbons, such as, for example, benzine, benzene, toluene and xylene, furthermore ethers, such as dioxane, glycol dimethyl ether and diglycol dimethyl ether, in addition nitriles, such as acetonitrile and also strongly polar solvents, such as dimethyl sulphoxide, sulpholane, dimethylformamide and N-methylpyrrolidone, or amines, such as pyridine or quinoline, are used.

All acid acceptors which can conventionally be used for this type of reactions are suitable as acid binder for carrying out the process (B-$b_1$) according to the invention. Preferably, alkali metal and alkaline earth metal oxides, hydroxides and carbonates, such as sodium hydroxide, potassium hydroxide, calcium oxide, sodium carbonate and potassium carbonate, furthermore alkali metal alcoholates, alkali metal amides and alkali metal hydrides, such as, for example, sodium methylate, sodium ethylate, potassium tert.-butylate, sodium amide and sodium hydride, as well as tertiary amines triethylamine, N,N-dimethylaniline, pyridine or N,N-dimethylaminopyridine, are used.

If bases, such as, for example, pyridine or quinoline, are used as solvents, then these can, with particular advantage, be simultaneously employed as acid binder in corresponding excess.

The reaction temperatures can be varied within a relatively wide range when the process (B-$b_1$) is carried out. In general, the process is carried out at temperatures between 0° C. and 200° C., preferably between 50° C. and 150° C.

The process (B-$b_1$) according to the invention is, in general, carried out under standard pressure.

To carry out the process (B-$b_1$) according to the invention, 0.5 to 10.0 moles, preferably 0.5 to 2.0 moles, of 4-hydroxy- or 4-mercaptobenzoic acid derivative of the formula (XIX) and 1.0 to 10.0 moles, preferably 1.0 to 3.0 moles, of acid binder are, in general, employed per mole of pyri(mi)dine derivative of the formula (XVIII). The reaction is carried out, the reaction products of the formula (I) are worked up and isolated in conventional fashion.

All conventional inert organic solvents are suitable as diluents for carrying out the process (B-$b_2$) according to the invention. Preferably, the solvents mentioned for process (B-b$_1$) are used.

All acid acceptors which can conventionally be used for such reactions are suitable as acid binder for carrying out the process (B-b$_2$) according to the invention. Preferably, the acid binders mentioned for process (B-b$_1$) are used.

The reaction temperatures can be varied within a relatively wide range when the process (B-b$_2$) according to the invention is carried out. In general, the process is carried out at temperatures between 0° C. and 200° C., preferably between 50° C. and 150° C.

In general, the process (B-b$_2$) is carried out under standard pressure.

To carry out the process (B-b$_2$) according to the invention, 0.5 to 10.0 moles, preferably 1.0 to 2.0 moles, of 4-halobenzoic acid derivative of the formula (XXI) and 1.0 to 10.0 moles, preferably 1.0 to 3.0 moles, of acid binder are employed per mole of 2-mercapto-pyri(mi)-dine derivative of the formula (XX). The reaction is carried out, the reaction products of the formula (I) are worked up and isolated according to generally conventional methods.

The solvents which are conventional for the respective reaction type are employed as diluent for carrying out the preparation process (C).

Thus, halogenation reactions (process C-c$_1$)) are preferably carried out in halogenated hydrocarbons, such as dichloromethane, chloroform, tetrachloromethane or chlorobenzene.

The reaction temperatures can be varied within a relatively wide range. In general, the reaction is carried out at temperatures between $-20°$ C. and $+150°$ C., preferably between 0° C. and $+100°$ C.

The halogenating agent is preferably employed in a stoichiometric amount or with an excess of up to 0.3 mole, and if appropriate, 0.01 to 0.1 mole, preferably 0.01 to 0.05 mole, of catalyst are added.

The reduction of nitro compounds to form amino compounds (process C-c$_2$), occurs using catalytically activated hydrogen, preferably in alcohols or cyclic ethers such as tetrahydrofuran or dioxane, as solvent.

The reaction temperatures can be varied within a relatively wide range. These are 0° C. to 150° C., preferably 10° C. to 100° C.

Raney nickel is preferred as catalyst, 0.01 to 0.1 mole being employed. Preferably, the reaction is carried out under pressure between 1 and 50 bar. The reduction using metals, such as iron, zinc or tin, metal salts in low valency states, such as iron-II salts, tin-II salts, or using compounds of sulphur in low valency states, such as sulphides, sulphites or dithionites, is preferably carried out in water, if appropriate as mixtures with alcohols, and (in the case of metallic reducing agents, in the simultaneous presence of alkalis or mineral acids. In the case of metallic reducing agents, the reaction can also be carried out in acetic acid.

The reaction temperatures are 0° to 120° C., preferably 20° to 100° C. At least 1 mole of reducing agent is employed, preferably in a suitable excess of 1.0 to 3.0 moles.

The acylation of compounds having an amino group in the phenyl part (process C-c$_3$), occurs under the conditions which are known in principle for this. All organic solvents which are inert towards acid halides or acid anhydrides and which are also stated, for example, for the preparation process (A-a$_1$), are suitable as diluent.

Alkali metal carbonates are alkaline earth metal carbonates or tertiary amines, such as triethylamine, N,N-dimethylaniline or pyridine, are used as acid binder.

The reaction temperatures can be varied within a relatively wide range. In general, the reaction is carried out between $-20°$ C. and $+150°$ C., preferably at 0° C. to $+100°$ C.

Substitution reactions of amino groups for halogen or cyano on the phenyl part (process (C-c$_4$) are carried out under the conditions which are known in principle for such reactions. A detailed description of this method, which is known as the Sandmeyer reaction, can be found in Houben-Weyl, Methoden der organischen Chemie [Methods of Organic Chemistry], vol. 5/3, pages 846 et seq., Georg Thieme Verlag Stuttgart 1985. For this, a diazonium salt solution which is generated from the amino compound in dilute mineral acid using nitrite is allowed to run into a copper-I salt solution. The reaction occurs with cleavage off of nitrogen. The initial temperature can vary between 0° C. and $+75°$ C. In general, the reaction is conducted to completion by warming to 70° C. to 100° C. If the mineral acid used has the same anion as the copper salt (for example Cl$^\ominus$), then 0.1 to 0.2 mole of copper salt are sufficient as catalyst, while in other cases, sulphuric acid, for example, is used to prepare the diazonium salt and at least the stoichiometric amount of the copper-I salt is required.

All conventional inert organic solvents are suitable as diluents for carrying out the process (D) according to the invention. Preferably, the solvents mentioned for process (B-b$_1$) are used.

If alcohols of the formula (XXII) in liquid form are used as reaction component, then these can be employed with particular advantage simultaneously as diluent, in appropriate excess.

All acid acceptors which can conventionally be used for such reactions are suitable as acid binder for carrying out the process (D) according to the invention. Preferably, the bases mentioned for process (B-b$_1$) are used. It is also possible to employ the amine of the formula (XXIII) simultaneously as acid binder, in appropriate excess.

The reaction temperatures can be varied within a relatively wide range when the process (D) according to the invention is carried out. In general, the process is carried out at temperatures between 0° C. and 150° C., preferably between 20° C. and 100° C.

The reactions with ammonia proceed more slowly, so that they must be carried out using gaseous ammonia in higher-boiling solvents at 80° C. to 150° C., or, however, the reactions are carried out in closed vessels under pressure.

To carry out the process (D) according to the invention, 1.0 to 5.0 moles, preferably 1.0 to 3.0 moles, of alcohol of the formula (XXII) or 1.0 to 5.0 moles, preferably 1.0 to 3.0 moles, of ammonia or amine of the formula (XXIII) and 1.0 to 5.0 moles, preferably 1.0 to 3.0 moles, of acid binder are employed per mole of pyri(mi)dyloxy- or -thiobenzoic acid derivative of the formula (If). The reaction is carried out, the reaction products are worked up and isolated according to methods which are known in principle.

The active compounds according to the invention can be used as defoliants, desiccants, agents for destroying broad-leaved plants and, especially, as weed-killers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver and Centaurea.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without tree plantings. Equally, the compounds can be employed for combating weeds in perennial cultures, for example afforestations, decorative tree plantings, fruit orchards, vineyards, citrus groves, nut orchards, banana plantations, coffee plantations, tea plantations, rubber plantations, oil palm plantations, cocoa plantations, soft fruit plantings and hop-fields, and for the selective combating of weeds in annual cultures.

In this case, the active compounds according to the invention can be particularly successfully employed for the selective combating of monocotyledon and dicotyledon weeds, preferably in monocotyledon crops, such as, for example, wheat.

In addition, the active compounds according to the invention engage in the metabolism of the plants and can therefore be used as growth regulators.

Experience to date of the mode of action of plant growth regulators has shown that an active compound can also exert several different actions on plants. The actions of the compounds depend essentially on the point in time at which they are used, relative to the stage of development of the plant, and on the amounts of active compound applied to the plants or their environment and the way in which the compounds are applied. In every case, growth regulators are intended to influence the crop plants in the particular manner desired.

The amount of leaf on plants can be controlled, under the influence of growth regulators, so that defoliation of the plants at a desired point in time is achieved. Such defoliation is of great importance in the mechanical harvesting of cotton, but is also of interest for faciliating harvesting in other crops, such as, for example, in viticulture. Defoliation of the plants can also be carried out to lower the transpiration of plants before they are transplanted. The active compounds can be converted to the customary formulations, such as solutions, emulsions, wettable powders, suspensions, powders, dusts, pastes, soluble powders, granules, suspension-emulsion concentrates, natural and synthetic substances impregnated with acitve compound, very fine capsules in polymeric substances and in coating compositions for seed, as well as ULV formulations.

These formulations are produced in known manner, for example by mixing the active compounds with extenders, that is liquid solvents and/or solid carriers, optionally with the use of surface-active agents, that is emulsifying agents and/or dispersing agents and/or foam-forming agents.

In the case of the use of water as an extender, organic solvents can, for example, also be used as auxiliary solvents. As liquid solvents, these are suitable in the main: aromatics, such as xylene, toluene or alkyl naphthalenes, chlorinated aromatics and chlorinated aliphatic hydrocarbons, such as chlorobenzenes, chloroethylenes or methylene chloride, aliphatic hydrocarbons, such as cyclohexane or paraffins, for example petroleum fractions, mineral and vegetable oils, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water.

As solid carriers there are suitable: for example ammonium salts and ground natural minerals, such as kaolins, clays, talc, chalk, quartz, attapulgite, montmorillonite or diatomaceous earth, and ground synthetic minerals, such as highly disperse silicic acid, alumina and silicates, as solid carriers for granules there are suitable: for example crushed and fractionated natural rocks such as calcite, marble, pumice, sepiolite and dolomite, as well as synthetic granules of inorganic and organic meals, and granules or organic material such as sawdust, coconut shells, maize cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkylsulphonates, alkylsulphates, arylsulphonates as well as albumin hydrolyzation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Further additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, maganese, boron, copper, cobalt, molybdenum and zinc.

The formulations in general contain between 0.1 and 95 percent by weight of active compound, preferably between 0.5 and 90%.

The active compounds according to the invention, as such or in the form of their formulations, can also be used, for combating weeds, as mixtures with known herbicides, finished formulations or tank mixes being possible.

Possible components for the mixtures are known herbicides, such as, for example, 1-amino-6-ethylthio-3-(2,2-dimethylpropyl)-1,3,5-triazine-2,4-(1H,3H)-dione or N-(2-benzothiazolyl)-N,N'-dimethyl-urea for combating weeds in cereals; 4-amino-3-methyl-6-phenyl-1,2,4-triazin-5-(4H)-one for combating weeds in sugar beet and 4-amino-6-(1,1-dimethylethyl)-3-methylthio-1,2,4-triazin-5(4H)-one for combating weeds in soya beans. Mixtures with N-benzothiazolyl-N-methyl-N'-methyl-urea, N,N-dimethyl-N'-(4-isopropylphenyl)-urea, N,N-dimethyl-N'-(3-chloro-4-methylphenyl)-urea, 2-chloro-N-{[(4-methoxy-6-methyl-1,3,5-triazin-2-yl)-amino]-carbonyl}-benzenesulphonamide, 2-chloro-4-ethylamino-6-isopropylamino)-1,3,5-triazine, 2-chloro-4-ethylamino-6-cyanopropylamino-1,3,5-triazine, 4-ethylamino-2-tert.-butylamino-6-methylthio-5-triazine, 4-amino-6-tert.-butyl-3-methylthio-4,5-dihydro-1,2,4-triazin-5-one, methyl 2-[4-(2,4-dichlorophenoxy)-phenoxy]-propionate, trimethylsilylmethyl 2-[4-(3,5-dichloropyrid-2-yloxy)phenoxy]propionate, 2,4-dichlorophenoxyacetic acid, 2,4-dichlorophenoxypropionic acid, (2-methyl-4-chlorophenoxy)acetic acid, (4-chloro-2-methyl-phenoxy)-propionic acid, 3,5-diiodo-4-hydroxybenzonitrile, methyl 5-(2,4-dichlorophenoxy)-2-nitrobenzoate, 3,6-dichloro-picolinic acid, 3-isopropyl-2,1,3-benzothiadiazin-4-one 2,2-dioxide and 6-chloro-3-phenyl-pyridazin-4-yl 5-octyl thiocarbonate are also, if appropriate, of advantage. Surprisingly, some mixtures also show a synergistic action.

Mixtures with other known active compounds, such as fungicides, insecticides, acaricides, nematicides, bird repellants, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying, atomizing or scattering. It is furthermore possible to apply the active compounds according to the ultra-low-volume process or to inject the active compound preparation or the active compound itself into the soil. The seed of the plants can also be treated.

The active compounds according to the invention can be applied either before or after emergence of the plants.

They can also be incorporated into the soil before sowing.

The amount of active compound used can vary within a substantial range. It depends essentially on the nature of the desired effect. In general, the amounts used are between 0.01 and 10 kg of active compound per hectare of soil surface, preferably between 0.05 and 5 kg per ha.

On use of the growth regulator, the active compounds according to the invention can also be present in the formulations in mixtures with other known active compounds, such as fungicides, insecticides, acaricides and herbicides, as well as in mixtures with fertilizers and other growth regulators.

The amounts used can also vary within a substantial range when used as growth regulator. In general, 0.01 to 50 kg, preferably 0.05 to 10 kg, of active compound are used per hectare of soil surface.

Regarding the time application, the growth regulators should be applied in a preferred period of time, the precise limitation of which depends on the climatic and vegetative circumstances.

The preparation and use of the active compounds according to the invention can be seen from the following examples.

PREPARATION EXAMPLES

Example 1

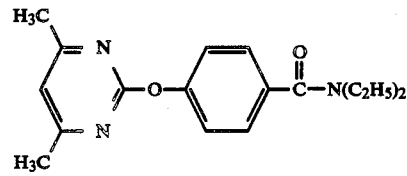

Process A-a₁

24.4 g (0.1 mol) of 4-(4,6-dimethyl-pyrimidyl-2-oxy)-benzoic acid are suspended in 200 ml of toluene. 10.1 g (0.1 mol) of triethylamine are added and 13.1 g (0.11 mol) of thionyl chloride are added dropwise at room temperature after about 30 minutes. The mixture is refluxed for 4 hours. The precipitate which deposits is filtered off under suction and the solution is concentrated in vacuo. The residue which remains is taken up in 150 ml of tetrachloromethane, the solution is decanted from insoluble components, stirred with charcoal, filtered and concentrated again. The residue is dissolved in 150 ml of tetrahydrofuran and treated dropwise at 10° to 15° C. with 14.6 g (0.2 mol) of diethylamine. The precipitate of dimethylamine hydrochloride is filtered off under suction and the solution is concentrated in vacuo. The residue is stirred with slightly acidified water, filtered off under suction, washed until neutral and dried.

25 g (83.6% of theory) of N,N-diethyl-4-(4,6-dimethylpyrimidyl-2-oxy)benzamide of melting point 95° to 96° C. (recrystallization from petroleum ether) are obtained.

Example 2

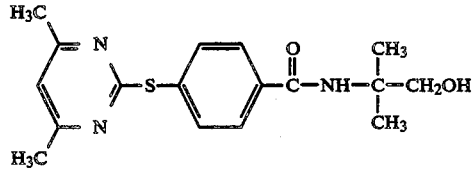

Process (A-a₁)

13 g (0.05 mol) of 4-(4,6-dimethyl-pyrimidyl-2-mercapto)-benzoic acid and 5.1 g (0.05 mol) of triethylamine are dissolved in 100 ml of tetrahydrofuran. 5.5 g (0.05 mol) of ethyl chloroformate are added dropwise with stirring and cooling at 10° to 15° C. The mixture is then stirred for 2 hours at room temperature and subsequently treated with 4.9 g (0.05 mol) of 2-amino-2-methyl-propanol. The mixture is then stirred for 1 hour at room temperature and subsequently refluxed for 2 hours and, after cooling, diluted with 500 ml of water. The crystals which have precipitated are filtered off under suction, stirred for 30 minutes in a 1% strength sodium hydroxide solution, filtered off under suction again, washed with water until neutral and dried.

10.5 g (63.5% of theory) of 4-(4,6-dimethyl-pyrimidyl-2-mercapto)-(2-methyl-3-hydroxy-propyl-2)-benzamide with melting point 90° to 91° C. (recrystallization from toluene) are obtained.

Example 3

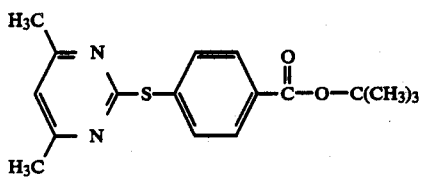

Process (A-a₁)

6.5 g (25 mmol) of 4-(4,6-dimethyl-pyrimidyl-2-mercapto)-benzoic acid are dissolved in 50 ml of absolute pyridine. 6.4 ml (50 mmol) of benzenesulphonyl chloride are added dropwise with cooling at 15° to 20° C. and the mixture is stirred for 1 hour at room temperature. After cooling in an ice bath, 2.4 ml (25 mmol) of tert.-butanol are added dropwise, the mixture is treated with 100 mg of Steglich base and stirred for 1 hour at room temperature. The solution is warmed for 6 hours at 60° C. and subsequently poured into ice water. The mixture is extracted using ether, the ether solution is dried, concentrated in vacuo and, as a solution in cyclohexane/ethyl acetate in the ratio 2:1, filtered through a column with silica gel.

After concentrating the eluate, 3.77 g (47.7% of theory) of tert.-butyl 4-(4,6-dimethyl-pyrimidyl-2-mercapto)-benzoate with melting point 75° to 77° C. (recrystallization from cyclohexane/n-hexane) are obtained.

Example 4

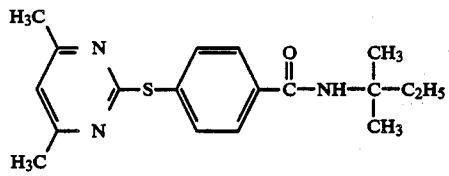

Process (A-a₁)

13 g (0.05 mol) of 4-(4,6-dimethyl-pyrimidyl-2-mercapto)-benzoic acid, 4.4 g (0.05 mol) of 1,1-dimethylpropylamine and 15.2 g (0.15 mol) of triethylamine are stirred in 200 ml of dichloromethane. 7.7 g (0.05 mol) of phosphoroxy chloride are added dropwise at room temperature. The mixture is refluxed for 1 hour and, after cooling, stirred into 500 ml of ice water. The organic layer is separated off, washed with water, approximately 1% strength sodium hydroxide solution and again with water, dried and concentrated in vacuo.

13.5 g (82% of theory) of N-(1,1-dimethyl-propyl)-4-(4,6-dimethyl-pyrimidyl-2-mercapto)-benzamide with melting point 129° to 130° C. (recrystallization from petroleum ether) are obtained.

Example 5

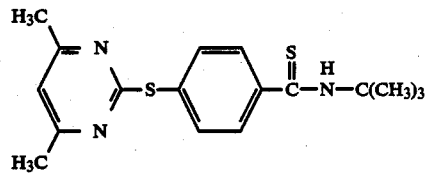

Process (A-a₄)/version γ

4.7 g (15 mmol) of N-tert.-butyl-4-(4,6-dimethyl-pyrimidyl-2-mercapto)-benzamide and 3.3 g (7.8 mmol) of Lawesson reagent are refluxed for 2 hours in 20 ml of absolute toluene. After cooling to room temperature, the solution is transferred onto silica gel and chromatographed using cyclohexane/ethyl acetate in the ratio 2:1.

After distilling off the solvent, 3.5 g (71% of theory) of N-tert.-butyl-4-(4,6-dimethyl-pyrimidyl-2-mercapto)-thiobenzamide with melting point 110° to 111° C. (recrystallization from toluene/petroleum ether) are obtained.

Example 6

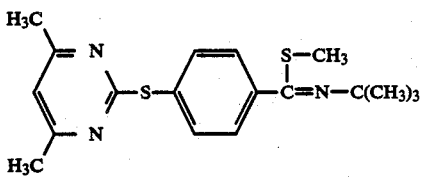

Process (A-a₅)/version β

0.6 g (20 mmol) of sodium hydride are initially introduced in 20 ml of absolute dimethylformamide under nitrogen. The solution of 6.62 g (20 mmol) of N-tert.-butyl-4-(4,6-dimethyl-pyrimidyl-2-mercapto)-thiobenzamide in 20 ml of absolute dimethylformamide is added dropwise at room temperatuure and the mixture is stirred until hydrogen evolution is no longer observed. 5.25 g (37.5 mmol) of methyl iodide are then added dropwise at room temperature with stirring and the mixture is stirred for a further 2 hours at room temperature. The mixture is poured into 250 ml of water, extracted using dichloromethane, the organic solution is dried and concentrated.

4.6 g (66.8% of theory) of N-tert.-butyl-4-(4,6-dimethyl-pyrimidyl-2-mercapto)-thiobenzimide methyl ester with melting point 88° to 90° C. (recrystallization from toluene/n-hexane) remain as residue.

Example 7

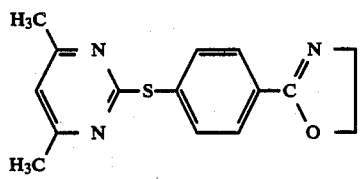

Process (A-a₇)/version α

7.42 g (30 mmol) of 4-(4,6-dimethyl-pyrimidyl-2-mercapto)-benzonitrile, 2.72 ml (45 mmol) of 2-hydroxyethylamine and 250 mg of anhydrous zinc chloride are warmed at 150° C. for 4 hours. After the reaction is complete, 30 ml of tetrahydrofuran are added, the mixture is poured onto water and extracted using dichloromethane. The organic layer is dried and concentrated in vacuo, and the residue is chromatographed using cyclohexane/ethyl acetate in the ratio 1:2.

3.5 g (40.8% of theory) of 2-[4-(4,6-dimethylpyrimidyl-2-mercapto-phenyl)]-1,3-oxazoline with melting point 98° to 99° C. (recrystallization from toluene/n-hexane) are obtained.

Example 8

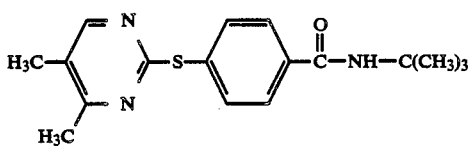

Process (B-b₁)

10.45 g (0.05 mol) of N-tert.-butyl-4-mercaptobenzamide are dissolved in 50 ml of sulpholane and treated with 2.8 g (0.05 mol) of potassium hydroxide powder in portions at room temperature. The mixture is stirred for 30 minutes at room temperature and 7.1 g (0.05 mol) of 2-chloro-4,5-dimethyl-pyrimidine are then added. The mixture is gradually heated to 110° C. and stirred for a further 5 hours at this temperature. After cooling, the mixture is poured into 1 liter of water. The aqueous layer is decanted and the semi-solid reaction product is taken up in toluene. The solution is washed once with approximately 1% strength sodium hydroxide solution and twice more with water, dried over sodium sulphate and concentrated in vacuo.

10.7 g (68% of theory) of N-tert.-butyl-4-(4,5-dimethyl-pyrimidyl-2-mercapto)-benzamide with melting point 127° to 128° C. (recrystallization from petroleum ether) remain as residue.

Example 9

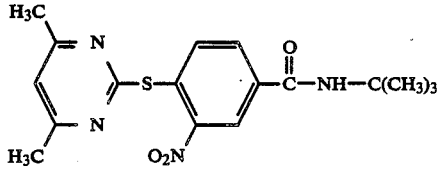

Process (B-b₂)

35.3 g (0.2 mol) of 2-mercapto-4,6-dimethyl-pyrimidine hydrochloride are suspended in 170 ml of sulpholane. 24.7 g (0.44 mol) of potassium hydroxide powder are added in portions at room temperature with stirring. The mixture is stirred for a further 30 minutes at room temperature and 51.3 g (0.2 mol) of 3-nitro-4-chloro-N-tert.-butyl-benzamide are then added. The mixture is stirred for 2 hours at 50° C. and for 4 hours at 120° C., subsequently cooled and stirred into 1 liter of ice water. The crystals which have precipitated are filtered off under suction and recrystal-lized from ethanol.

58.6 g (81.3% of theory) of 3-nitro-4-(4,6-dimethyl-pyrimidyl-2-mercapto-) N-tert.-butyl-benzamide with melting point 157° to 158° C. are obtained.

Example 10

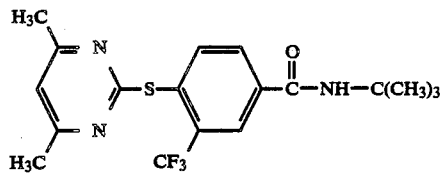

In a corresponding fashion, N-tert.-butyl-3-trifluoromethyl-4-(4,6-dimethyl-pyrimidyl-2-mercapto)-benzamide with melting point 131° C. (recrystallization from petroleum ether) are obtained from N-tert.-butyl-4-chloro-3-trifluoromethyl-benzamide according to process (B-b₂).

Example 11

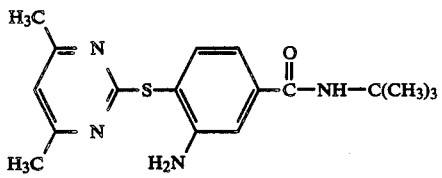

Process (C-c₁)

36 g (0.1 mol) of N-tert.-butyl-3-nitro-4-(4,6-dimethyl-pyrimidyl-2-mercapto)-benzamide are hydrogenated to exhaustion in 350 ml of dioxane in an autoclave with addition of 7 g of Raney nickel at 20° to 50° C. The catalyst is filtered off under suction and the solution is concentrated in vacuo. About 32 g (practically quantitative yield) of N-tert.-butyl-3-amino-4-(4,6-dimethyl-pyrimidyl-2-mercapto)-benzamide with melting point 182° to 183° C. (recrystallization from toluene) remain as residue.

Example 12

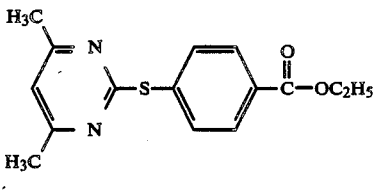

Process (B-b₁)

91 g (0.5 mol) of 4-mercapto-benzoic acid ethyl ester are dissolved in 250 ml of dimethyl sulphoxide. 28 g (0.5 mol) of powdered potassium hydroxide are added with stirring. When the slightly exothermic reaction has died down (30 minutes), 71.2 g (0.5 mol) of 2-chloro-4,6-dimethyl-pyrimidine are added in portions at room temperature and the mixture is gradually heated to 110° C. to 120° C. After stirring for 5 hours at this temperature, the mixture is cooled to room temperature and then diluted with 1.5 liter of water. The crystals which have precipitated are filtered off under suction and dried.

118 g (82% of theory) of ethyl 4-(4,6-dimethylpyrimidyl-2-mercapto)-benzoate with melting point 93° C. to 94° C. (recrystallization from petroleum ether) are obtaied.

Example 13

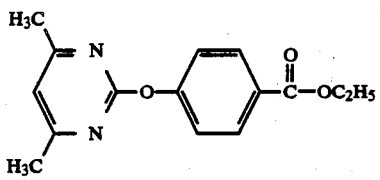

Melting point 95° C. to 96° C. (recrystallization from petroleum ether)

Process (B-b₁)

Ethyl 4-(4,6-dimethyl-pyrimidyl-2-oxy)-benzoate is obtained from ethyl 4-hydroxy-benzoate and 2-chloro-4,6-dimethylpyrimidine analogously to Example 12.

The pyri(mi)dyloxy- and -thiobenzoic acid derivatives of the formula (I) which are listed as formulae in the following Table 1 are obtained in corresponding fashion to the preparation examples and according to the general directions for the preparation:

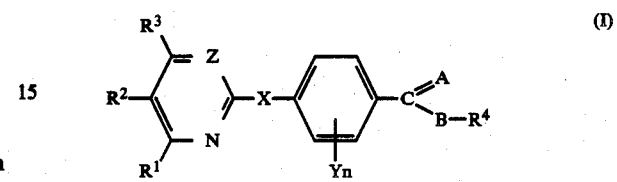

(I)

TABLE 1

| Example No. | Z | R¹ | R² | R³ | X | Y | A | B | R⁴ | melting point (°C.) |
|---|---|---|---|---|---|---|---|---|---|---|
| 14 | CH | CH₃ | H | H | S | — | O | NH | —C(CH₃)₃ | 133–134 |
| 15 | CH | CH₃ | H | CH₃ | S | — | O | NH | —C(CH₃)₃ | 142–143 |
| 16 | CH | CH₃ | CH₃ | Cl | S | — | O | NH | —C(CH₃)₃ | 150–152 |
| 16a | CH | H | H | H | S | — | O | NH | —C(CH₃)₃ | 106–108 |
| 17 | CH | H | H | CH₃ | S | — | O | NH | —C(CH₃)₃ | 45 |
| 18 | N | CH₃ | H | H | S | — | O | O | —C(CH₃)₃ | 104–105 |
| 19 | N | CH₃ | H | H | S | — | O | NH | —C(CH₃)₃ | |
| 20 | N | CH₃ | H | H | S | — | O | NH | $-\overset{CH_3}{\underset{CH_3}{C}}-C_2H_5$ | 88–90 |
| 21 | N | CH₃ | H | H | S | — | O | NH | $-\overset{CH_3}{\underset{CH_3}{C}}-CH(CH_3)_2$ | |
| 22 | N | CH₃ | H | H | S | — | O | NH | $-\overset{CH_3}{\underset{CH_3}{C}}-C\equiv CH$ | |
| 23 | N | CH₃ | H | H | S | — | O | NH | CH₃-cyclopentyl | 90–91 |
| 24 | N | CH₃ | H | H | S | — | O | NH | $-\overset{CH_3}{\underset{CH_3}{C}}-CN$ | 118–120 |
| 25 | N | CH₃ | H | H | S | — | O | NH | $-\overset{CH_3}{\underset{C_2H_5}{C}}-CN$ | 128–129 |
| 26 | N | CH₃ | H | H | S | — | S | NH | —C(CH₃)₃ | oil |
| 26a | N | CH₃ | H | H | S | 2-Cl | O | O | —C(CH₃)₃ | |
| 27 | N | CH₃ | H | H | S | 2-Cl | O | NH | —C(CH₃)₃ | |
| 28 | N | CH₃ | H | H | S | 3-Cl | O | NH | —C(CH₃)₃ | |
| 29 | N | CH₃ | H | H | S | 2-CH₃ | O | NH | —C(CH₃)₃ | |
| 30 | N | CH₃ | H | H | S | 3-CH₃ | O | NH | —C(CH₃)₃ | |
| 31 | N | CH₃ | H | H | S | 3-NO₂ | O | NH | —C(CH₃)₃ | 155–156 |

TABLE 1-continued

| No. | | | | | | | | | | m.p. |
|---|---|---|---|---|---|---|---|---|---|---|
| 32 | N | CH₃ | H | H | S | — | O | NH | —C(CH₃)₃ | 94 |
| 33 | N | CH₃ | H | Cl | S | — | O | NH | —C(CH₃)₃ | |
| 34 | N | CH₃ | H | OCH₃ | S | — | O | NH | —C(CH₃)₃ | |
| 35 | N | CH₃ | H | OCH(CH₃)₂ | S | — | O | NH | —C(CH₃)₃ | |
| 36 | N | CH₃ | H | O—CH₂—CH=CH₂ | S | — | O | NH | —C(CH₃)₃ | |
| 37 | N | CH₃ | H | O—CH₂—CH₂—OCH₃ | S | — | O | NH | —C(CH₃)₃ | 184 |
| 38 | N | CH₃ | H | NH₂ | S | — | O | NH | —C(CH₃)₃ | 70-72 |
| 39 | N | CH₃ | H | NH—CH₃ | S | — | O | NH | —C(CH₃)₃ | oil |
| 39a | N | CH₃ | H | NH—▷ (cyclopropyl) | S | — | O | NH | —C(CH₃)₃ | |
| 40 | N | CH₃ | H | NH—C₂H₅ | S | — | O | NH | —C(CH₃)₃ | oil |
| 41 | N | CH₃ | H | NH—CH₂—CH=CH₂ | S | — | O | NH | —C(CH₃)₃ | oil |
| 42 | N | CH₃ | H | NH—CH(CH₃)₂ | S | — | O | NH | —C(CH₃)₃ | 169 |
| 42a | N | CH₃ | H | —NH—C(CH₃)₃ | S | — | O | NH | —C(CH₃)₃ | |
| 43 | N | CH₃ | H | NH(CH₃)₂ | S | — | O | NH | —C(CH₃)₃ | |
| 44 | N | CH₃ | H | N(CH₂—CH=CH₂)₂ | S | — | O | NH | —C(CH₃)₃ | |
| 45 | N | CH₃ | H | pyrrolidin-1-yl | S | — | O | NH | —C(CH₃)₃ | |
| 46 | N | CH₃ | H | piperidin-1-yl | S | — | O | NH | —C(CH₃)₃ | |
| 47 | N | CH₃ | H | morpholin-4-yl | S | — | O | NH | —C(CH₃)₃ | |
| 48 | N | CH₃ | H | 4-methylpiperazin-1-yl | S | — | O | NH | —C(CH₃)₃ | |
| 49 | N | C₂H₅ | H | H | S | — | O | NH | —C(CH₃)₃ | 114-116 |
| 50 | N | (CH₃)₂CH | H | H | S | — | O | NH | —C(CH₃)₃ | 86-87 |
| 51 | N | H | CH₃ | H | S | — | O | O | —C(CH₃)₃ | 163-164 |
| 52 | N | H | CH₃ | H | S | — | S | NH | —C(CH₃)₃ | 155-157 |
| 53 | N | H | CH₃ | H | S | — | O | NH | —C(CH₃)₃ | |

TABLE 1-continued

| No. | | | | | | | | | mp/yield |
|---|---|---|---|---|---|---|---|---|---|
| 53a | N | H | CH₃ | | S | — | N | S—CH₃ | —C(CH₃)₃ | 80 |
| 53b | N | H | CH₃ | | S | — | N | S—C₂H₅ | —C(CH₃)₃ | 48 |
| 53c | N | H | CH₃ | | S | — | N | S—CH₂CH=CH₂ | —C(CH₃)₃ | 45 |
| 54 | N | H | C₂H₅ | | S | — | O | NH | —C(CH₃)₃ | 149–150 |
| 55 | N | H | C₃H₇ | | S | — | O | NH | —C(CH₃)₃ | 95–96 |
| 56 | N | H | CH(CH₃)₂ | | S | — | O | NH | —C(CH₃)₃ | 137–138 |
| 57 | N | H | C(CH₃)₃ | | S | — | O | NH | —C(CH₃)₃ | oil |
| 58 | N | CH₃ | CH₃ | | S | — | O | O | —C(CH₃)₃ | oil |
| 58a | N | CH₃ | CH₃ | | S | 3-CH₃ | O | O | —C(CH₃)₂C₂H₅ | 55 |
| 58b | N | CH₃ | CH₃ | | S | 3-CH₃ | O | O | —C(CH₃)₃ | 45 |
| 58c | N | CH₃ | CH₃ | | S | — | O | O | —C(CH₃)₂C₂H₅ | 50 |
| 59 | N | C₂H₅ | H | | S | — | O | O | —C(CH₃)₃ | |
| 59a | N | C₂H₅ | H | | S | 3-CH₃ | O | O | —C(CH₃)₃ | 89 |
| 59b | N | CH₃ | CH₃ | H | S | — | O | NH | 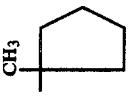 CH₃—C(CH₃)—CF₃ | 106–108 |
| 60 | N | CH₃ | CH₃ | H | S | — | O | NH | 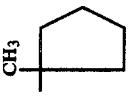 CH₃—C(CH₃)—C₂H₅ | 109–110 |
| 61 | N | CH₃ | CH₃ | H | S | — | O | NH | 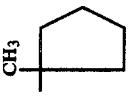 CH₃—C(CH₃)—CH(CH₃)₂ | 137–138 |
| 62 | N | CH₃ | CH₃ | H | S | — | O | NH | 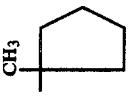 CH₃—C(CH₃)—C≡CH | 108–109 |
| 63 | N | CH₃ | CH₃ | H | S | — | O | NH | 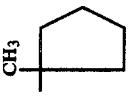 1-methylcyclopentyl | 125–126 |
| 64 | N | CH₃ | CH₃ | H | S | — | O | NH | 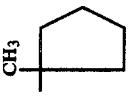 CH₃—C(C₂H₅)—CN | 125–126 |

TABLE 1-continued

| | | | | | | | | |
|---|---|---|---|---|---|---|---|---|
| 64a | N | CH₃ | CH₃ | H | S | — | O | NH | —C(CH₃)(CH₂—C(CH₃)₃)CH₃ | 148–149 |
| 65 | N | CH₃ | CH₃ | H | S | — | O | NH | —C(CH₃)(CN)C₃H₇ | 60–61 |
| 65a | N | CH₃ | CH₃ | H | S | — | O | NH | —C(CH₃)(CH₂—OCH₃)CH₃ | |
| 65b | N | CH₃ | CH₃ | H | S | 3-CH₃ | O | NH | —C(CH₃)₃ | 155 |
| 65c | N | CH₃ | CH₃ | H | S | 3-CH₃ | O | NH | —C(CH₃)₂C₂H₅ | 84 |
| 66 | N | CH₃ | CH₃ | H | S | — | S | NH | —C(CH₃)₃ | 144–145 |
| 66a | N | CH₃ | CH₃ | H | S | — | S | NH | —C(CH₃)(C₂H₅)CH₃ | 120 |
| 67 | N | CH₃ | CH₃ | H | S | — | S | NH | —C(CH₃)(CH₂—C(CH₃)₃)CH₃ | 124–125 |
| 67a | N | CH₃ | CH₃ | H | S | — | N | S—CH₃ | C(CH₃)₂C₂H₅ | 58 |
| 67b | N | CH₃ | CH₃ | H | S | — | N | S—CH₂—CH=CH₂ | —C(CH₃)₂C₂H₅ | oil |
| 68 | N | CH₃ | CH₃ | Cl | S | — | O | NH | —C(CH₃)₃ | 198 |
| 69 | N | CH₃ | CH₃ | NH₂ | S | — | O | NH | —C(CH₃)₃ | oil |
| 70 | N | CH₃ | C₂H₅ | H | S | — | O | O | —C(CH₃)₃ | 101 |
| 71 | N | CH₃ | C₂H₅ | H | S | — | O | NH | —C(CH₃)₃ | 52 |
| 71a | N | CH₃ | C₂H₅ | H | S | — | O | O | —C(CH₃)₃ | oil |
| 71b | N | CH₃ | C₂H₅ | H | S | 3-Cl | O | S | —C(CH₃)₃ | oil |
| 71c | N | CH₃ | C₂H₅ | H | S | — | O | S | —C(CH₃)₃ | 98 |
| 71d | N | CH₃ | C₂H₅ | H | S | 3-Cl | O | NH | —C(CH₃)₃ | 144 |
| 71e | N | CH₃ | C₂H₅ | H | S | 3-Cl | O | NH | —C(CH₃)₃ | 133–134 |
| 71f | N | CH₃ | C₂H₅ | H | S | 3-CH₃ | O | NH | —C(CH₃)₃ | 36 |
| 71g | N | CH₃ | CH(CH₃)₂ | H | S | — | O | O | —C(CH₃)₃ | |
| 72 | N | CH₃ | CH₃ | H | S | — | O | NH | —C(CH₃)₃ | 45 |
| 73 | N | C₂H₅ | C₂H₅ | H | S | 3-CH₃ | O | NH | —C(CH₃)₃ | 30 |
| 73a | N | C₂H₅ | C₂H₅ | H | S | 3-CH₃ | O | NH | —C(CH₃)₂C₂H₅ | 99–100 |
| 73b | N | C₂H₅ | C₂H₅ | H | S | — | O | NH | —C(CH₃)₃ | 161 |
| 74 | N | C₂H₅ | C₂H₅ | H | S | 3-CH₃ | O | NH | —C(CH₃)₃ | |
| 74a | N | C₃H₇ | C₂H₅ | H | S | — | O | NH | —C(CH₃)₃ | |
| 75 | N | CH(CH₃)₂ | CH₃ | H | S | — | O | NH | —C(CH₃)₃ | |
| 76 | N | CH₃ | CH₃ | H | S | — | O | NH | —C(CH₃)₃ | |
| 77 | N | —(CH₂)₃— | | H | S | — | O | NH | —C(CH₃)₃ | |

TABLE 1-continued

| | | | | | | | | |
|---|---|---|---|---|---|---|---|---|
| 78 | N | —(CH$_2$)$_4$— | | H | s | — | NH | —C(CH$_3$)$_3$ | |
| 79 | N | —CH=CH—CH=CH— | | H | s | — | NH | —C(CH$_3$)$_3$ | |
| 80 | N | —CH=CH—C(Cl)=CH— | | H | s | — | NH | —C(CH$_3$)$_3$ | |
| 80a | N | CH$_3$ | H | CH$_3$ | O | — | O | C(CH$_3$)$_3$ | 166-167 |
| 80b | N | CH$_3$ | H | CH$_3$ | O | — | S | C(CH$_3$)$_3$ | 127-128 |
| 81 | N | CH$_3$ | H | CH$_3$ | S | — | S | —C$_2$H$_5$ | 166-167 |
| 82 | N | CH$_3$ | H | CH$_3$ | S | — | S | —C(CH$_3$)$_3$ | 117-118 |
| 83 | N | CH$_3$ | H | CH$_3$ | O | — | NH | —CH$_3$ | 139-140 |
| 84 | N | CH$_3$ | H | CH$_3$ | O | — | NH | —C$_2$H$_5$ | |
| 85 | N | CH$_3$ | H | CH$_3$ | O | — | NH | —C$_3$H$_7$ | |
| 86 | N | CH$_3$ | H | CH$_3$ | O | — | NH | —CH(CH$_3$)$_2$ | |
| 87 | N | CH$_3$ | H | CH$_3$ | O | — | NH | —CH$_4$H$_9$ | |
| 88 | N | CH$_3$ | H | CH$_3$ | O | — | NH | —CH$_2$—CH(CH$_3$)$_2$ | |
| 89 | N | CH$_3$ | H | CH$_3$ | O | — | NH | —CH(CH$_3$)(C$_2$H$_5$) | 139-140 |
| 90 | N | CH$_3$ | H | CH$_3$ | O | — | NH | —C(CH$_3$)$_3$ | 170 |
| 91 | N | CH$_3$ | H | CH$_3$ | O | — | NH | —CH$_2$—C(CH$_3$)$_3$ | 147-148 |
| 92 | N | CH$_3$ | H | CH$_3$ | O | — | NH | —C(CH$_3$)(C$_2$H$_5$)(CH$_3$) | 144-145 |
| 93 | N | CH$_3$ | H | CH$_3$ | O | — | NH | —CH$_2$—CH(C$_2$H$_5$)(C$_4$H$_9$) | 95-96 |
| 94 | N | CH$_3$ | H | CH$_3$ | O | — | NH | —CH$_2$—CH=CH$_2$ | 104-105 |
| 95 | N | CH$_3$ | H | CH$_3$ | O | — | NH | —CH$_2$—C$_6$H$_5$ | 139-140 |
| 96 | N | CH$_3$ | H | CH$_3$ | O | — | NH | —CH$_2$—CH$_2$—C$_6$H$_5$ | 131-132 |
| 97 | N | CH$_3$ | H | CH$_3$ | O | — | NH | —CH(CH$_3$)—C$_6$H$_5$ | 178-179 |

| | 98 | 99 | 100 | 101 | 102 | 103 | 104 | 105 |
|---|---|---|---|---|---|---|---|---|
| | N | N | N | N | N | N | N | N |
| | CH₃ | CH₃ | CH₃ | CH₃ | CH₃ | CH₃ | CH₃ | CH₃ |
| | H | H | H | H | H | H | H | H |
| | CH₃ | CH₃ | CH₃ | CH₃ | CH₃ | CH₃ | CH₃ | CH₃ |
| | O | O | O | O | O | O | O | O |
| | — | — | — | — | — | — | — | — |
| | O | O | O | O | O | O | O | O |
| | NH | NH | NH | NH | NH | NH | NH | NH |
| R | 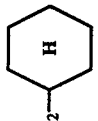 | —(CH₂)₃—OCH₃ | 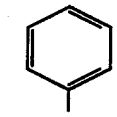 | 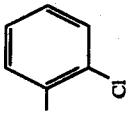 | 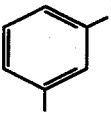 | 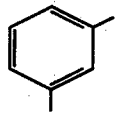 | 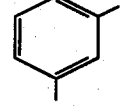 | 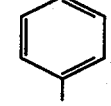 |
| m.p. | 168–169 | 72–73 | 153–154 | 119–120 | 123–124 | 171–172 | 114–115 | 160 |

| No. | X | R1 | R2 | R3 | | Y | | Z | Ar | mp |
|---|---|---|---|---|---|---|---|---|---|---|
| 106 | N | CH₃ | H | CH₃ | O | — | O | NH | 2-SCH₃-4-Cl-phenyl | 178–179 |
| 107 | N | CH₃ | H | CH₃ | O | — | O | NH | 3-NO₂-phenyl | 202–203 |
| 108 | N | CH₃ | H | CH₃ | O | — | O | NH | 2-CH₃-phenyl | 159–160 |
| 109 | N | CH₃ | H | CH₃ | O | — | O | NH | 4-CH₃-phenyl | 153–154 |
| 110 | N | CH₃ | H | CH₃ | O | — | O | NH | 3,4-diCl-phenyl | 160 |
| 111 | N | CH₃ | H | CH₃ | O | — | O | NH | 3-CN-phenyl | 151–152 |
| 112 | N | CH₃ | H | — | O | — | O | NH | 5-(furan-2-yl)methyl | 134–135 |

| No. | | | | | | | | | mp |
|---|---|---|---|---|---|---|---|---|---|
| 113 | N | CH₃ | H | CH₃ | — | O | NH | [2-methyl-thiazol-yl] | 165-166 |
| 114 | N | CH₃ | H | CH₃ | — | O | NCH₃ | CH₃ | 93-94 |
| 115 | N | CH₃ | H | CH₃ | — | O | NCH₃ | [cyclohexyl] | 120-121 |
| 116 | N | CH₃ | H | CH₃ | — | O | NCH₃ | [phenyl] | 171-172 |
| 117 | N | CH₃ | H | CH₃ | — | O | NC₃H₇ | C₃H₇ | 93-94 |
| 118 | N | CH₃ | H | CH₃ | — | O | NCH(CH₃)₂ | CH(CH₃)₂ | 91-92 |
| 119 | N | CH₃ | H | CH₃ | — | O | NC₄H₉ | C₄H₉ | oil |
| 120 | N | CH₃ | H | CH₃ | — | O | NCH₂—CH=CH₂ | CH₂—CH=CH₂ | 71-72 |
| 121 | N | CH₃ | H | CH₃ | — | O | | [pyrrolidin-1-yl] | 156-157 |
| 122 | N | CH₃ | H | CH₃ | — | O | | [morpholin-4-yl] | 110-111 |
| 123 | N | CH₃ | H | CH₃ | 3-Cl | O | O | —C₂H₅ | 117-118 |
| 124 | N | CH₃ | H | CH₃ | 3-Cl | O | NH | —C(CH₃)₃ | 199-200 |
| 125 | N | CH₃ | H | CH₃ | 3-Cl | O | NH | CH₃—C(C₂H₅)(CH₃)— | 184 |
| 126 | N | CH₃ | H | CH₃ | 3-Cl | O | NH | CH₃—C(C≡CH)(CH₃)— | 216-218 |

-continued

| No. | | | | | | 3-Cl | O | NH | | |
|---|---|---|---|---|---|---|---|---|---|---|
| 127 | N | CH₃ | H | CH₃ | O | 3-Cl | O | NH | ![1-methylcyclopentyl] | 196–198 |
| 128 | N | CH₃ | H | CH₃ | S | — | O | O | —C₂H₅ | 93–94 |
| 128a | N | CH₃ | H | CH₃ | S | — | O | O | —CH₂—C(CH₃)₂—CH₂—OCH₃ | 67 |
| 128b | N | CH₃ | H | CH₃ | S | — | O | O | —CH₂—C(CH₃)₂—CH₂—O—C₂H₅ | oil |
| 128c | N | CH₃ | H | CH₃ | S | — | O | O | —C₂H₄—O—C₂H₅ | oil |
| 129 | N | CH₃ | H | CH₃ | S | — | O | O | —CH(CH₃)₂ | 87–88 |
| 130 | N | CH₃ | H | CH₃ | S | — | O | O | —C(CH₃)₂—C₂H₅ | oil |
| 131 | N | CH₃ | H | CH₃ | S | — | O | O | —C(CH₃)₂—C₂H₅ | oil |
| 132 | N | CH₃ | H | CH₃ | S | — | O | O | —C(CH₃)₂—C₁₂H₂₅ | oil |
| 133 | N | CH₃ | H | CH₃ | S | — | O | O | —C(CH₃)₂—CH=CH₂ | 60–70 |
| 134 | N | CH₃ | H | CH₃ | S | — | O | O | —C(CH₃)₂—CH₂—CH=CH₂ | oil |
| 135 | N | CH₃ | H | CH₃ | S | — | O | O | —C(CH₃)₂—(CH₂)₃—CH(CH₃)—CH=CH₂ | oil |

-continued

| No. | | | | | | | | | R | mp |
|---|---|---|---|---|---|---|---|---|---|---|
| 136 | N | CH$_3$ | H | CH$_3$ | S | — | O | O | —C(CH$_3$)$_2$—C≡CH | 71–72 |
| 137 | N | CH$_3$ | H | CH$_3$ | S | — | O | O | —C(CH$_3$)(C$_2$H$_5$)—C≡CH | 73–74 |
| 138 | N | CH$_3$ | H | CH$_3$ | S | — | O | O | —C(CH$_3$)$_2$—C≡CCl | 90–91 |
| 139 | N | CH$_3$ | H | CH$_3$ | S | — | O | O | —C(CH$_3$)(CH(CH$_3$)$_2$)—C≡CH | 85–86 |
| 140 | N | CH$_3$ | H | CH$_3$ | S | — | O | O | —C(C$_2$H$_5$)$_2$—C≡CH | 90–91 |
| 141 | N | CH$_3$ | H | CH$_3$ | S | — | O | O | —C(CH$_3$)$_2$—CH$_2$—C≡CCl | oil |
| 142 | N | CH$_3$ | H | CH$_3$ | S | — | O | O | 1-methylcyclopentyl | 70–72 |
| 143 | N | CH$_3$ | H | CH$_3$ | S | — | O | O | 1-methylcyclohexyl | 64–65 |
| 144 | N | CH$_3$ | H | CH$_3$ | S | — | O | O | 1-ethynylcyclopentyl | 96–98 |

| No. | | | | | | | | | | mp |
|---|---|---|---|---|---|---|---|---|---|---|
| 145 | N | CH₃ | H | CH₃ | S | — | O | O | 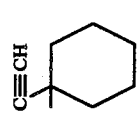 | 137-138 |
| 146 | N | CH₃ | H | CH₃ | S | — | O | O | 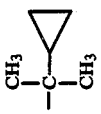 | 48-50 |
| 147 | N | CH₃ | H | CH₃ | S | — | O | O | 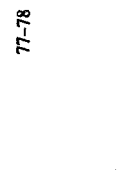 | 77-78 |
| 148 | N | CH₃ | H | CH₃ | S | — | O | O |  | 83-84 |
| 149 | N | CH₃ | H | CH₃ | S | — | O | O | CH₃—C(CN)—CF₃ | 67-68 |
| 150 | N | CH₃ | H | CH₃ | S | — | O | O | CH₃—C(CN)—C₂H₅ | 71-72 |
| 150a | N | CH₃ | H | CH₃ | S | — | O | O |  | oil |
| 150b | N | CH₃ | H | CH₃ | S | — | O | O |  | 72-73 |
| 151 | N | CH₃ | H | CH₃ | S | — | O | O | 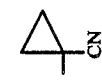 | 76-77 |

| | | | | | | | | | | |
|---|---|---|---|---|---|---|---|---|---|---|
| 151a | N | CH₃ | H | CH₃ | S | — | O | O |  | 104–105 |
| 152 | N | CH₃ | H | CH₃ | S | — | O | O | 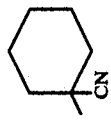 | 115–116 |
| 152a | N | CH₃ | H | CH₃ | S | — | O | O | 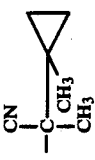 | 72 |
| 153 | N | CH₃ | H | CH₃ | S | — | O | O | 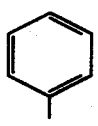 | 121–122 |
| 154 | N | CH₃ | H | CH₃ | S | — | O | O | 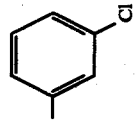 | 88–89 |
| 155 | N | CH₃ | H | CH₃ | S | — | O | O | 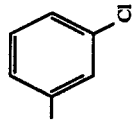 | 119–120 |
| 156 | N | CH₃ | H | CH₃ | S | — | O | O | 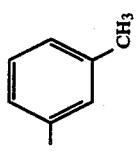 | 103–104 |
| 157 | N | CH₃ | H | CH₃ | S | — | O | O | 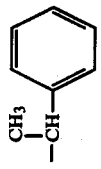 | oil |

| | | | | | | | |
|---|---|---|---|---|---|---|---|
| 158 | N | CH₃ | H | CH₃ | S | — | O |
| 159 | N | CH₃ | H | CH₃ | S | — | O |
 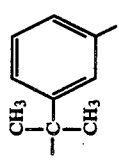
103-104
87-88

| No. | | | | | | | | | Substituent | mp |
|---|---|---|---|---|---|---|---|---|---|---|
| 160 | N | CH₃ | H | CH₃ | S | — | O | O | —C(CH₃)₂—CH₂—C₆H₅ | oil |
| 161 | N | CH₃ | H | CH₃ | S | — | O | O | —C(CH₃)₂—CH₂—C₆H₄Cl (4-Cl) | oil |
| 162 | N | CH₃ | H | CH₃ | S | — | O | O | —C(CH₃)₂—CH₂—CH₂—C₆H₅ | oil |
| 162a | N | CH₃ | H | CH₃ | S | — | O | O | —CH(CH₃)₂ | 70–71 |
| 163 | N | CH₃ | H | CH₃ | S | — | O | O | —C(CH₃)₃ | 69–70 |
| 163a | N | CH₃ | H | CH₃ | S | — | S | O | —C(CH₃)(CH₃)(C₂H₅) | 70–71 |
| 164 | N | CH₃ | H | CH₃ | S | — | S | O | 1-methylcyclopentyl | — |
| 165 | N | CH₃ | H | CH₃ | S | — | S | O | 1-methylcyclohexyl | — |
| 165a | N | CH₃ | H | CH₃ | S | — | S | O | —C(CH₃)₂—CH₂—N(morpholino) | oil |
| 166 | N | CH₃ | H | CH₃ | S | — | NH | O | —C(CH₃)₃ | 153–154 |
| 167 | N | CH₃ | H | CH₃ | S | — | NH | O | —CH(CH₃)—C(CH₃)₃ | 135–136 |

-continued

| No. | | | | | | | | | R | mp |
|---|---|---|---|---|---|---|---|---|---|---|
| 168 | N | CH₃ | H | CH₃ | S | — | O | NH | $-\overset{CH_3}{\underset{CH_3}{C}}-CH(CH_3)_2$ | 112–113 |
| 169 | N | CH₃ | H | CH₃ | S | — | O | NH | $-\overset{CH_3}{\underset{CH_3}{C}}-CH_2-C(CH_3)_3$ | 75–78 |
| 170 | N | CH₃ | H | CH₃ | S | — | O | NH | $-\overset{CH_3}{\underset{CH_3}{C}}-CH_2F$ | 145–146 |
| 171 | N | CH₃ | H | CH₃ | S | — | O | NH | $-\overset{CH_3}{C}H-CF_3$ | 154–156 |
| 172 | N | CH₃ | H | CH₃ | S | — | O | NH | $-\overset{CH_3}{\underset{CH_3}{C}}-CF_3$ | 119–121 |
| 173 | N | CH₃ | H | CH₃ | S | — | O | NH | $-\overset{CH_3}{\underset{CH_3}{C}}-CH=CH_2$ | 157–158 |
| 174 | N | CH₃ | H | CH₃ | S | — | O | NH | $-\overset{CH_3}{\underset{CH_3}{C}}-CH=CCl_2$ | |
| 175 | N | CH₃ | H | CH₃ | S | — | O | NH | $-\overset{CH_3}{\underset{CH_3}{C}}-C\equiv CH$ | 147–148 |
| 176 | N | CH₃ | H | CH₃ | S | — | O | NH | $-\overset{C_2H_5}{\underset{C_2H_5}{C}}-C\equiv CH$ | 138–139 |

-continued
| # | | | | | | | | | structure | mp |
|---|---|---|---|---|---|---|---|---|---|---|
| 176a | N | CH₃ | H | CH₃ | S | — | O | NH | 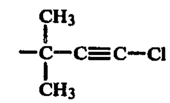 | oil |
| 177 | N | CH₃ | H | CH₃ | S | — | O | NH | 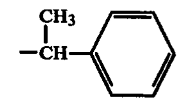 | 156–157 |
| 178 | N | CH₃ | H | CH₃ | S | — | O | NH | 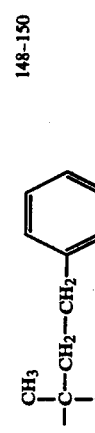 | 148–150 |
| 179 | N | CH₃ | H | CH₃ | S | — | O | NH | 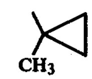 | 178–180 |
| 180 | N | CH₃ | H | CH₃ | S | — | O | NH | 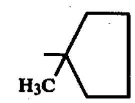 | 137–138 |
| 181 | N | CH₃ | H | CH₃ | S | — | O | NH | 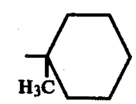 | 114–115 |
| 182 | N | CH₃ | H | CH₃ | S | — | O | NH | 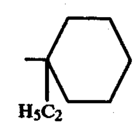 | 149–150 |
| 183 | N | CH₃ | H | CH₃ | S | — | O | NH | 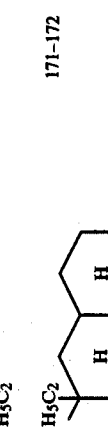 | 171–172 |
| 184 | N | CH₃ | H | CH₃ | S | — | O | NH | 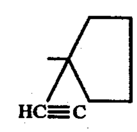 | |

| | | | | | | | | mp (°C) |
|---|---|---|---|---|---|---|---|---|
| 184 | N | CH₃ | H | CH₃ | S | — | O | NH | 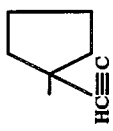 | |
| 185 | N | CH₃ | H | CH₃ | S | — | O | NH |  | 171–172 |
| 186 | N | CH₃ | H | CH₃ | S | — | O | NH |  | 104–106 |
| 187 | N | CH₃ | H | CH₃ | S | — | O | NH | 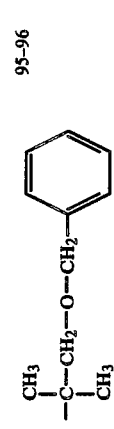 | 95–96 |
| 188 | N | CH₃ | H | CH₃ | S | — | O | NH | 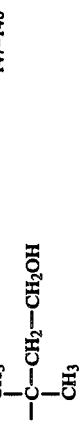 | 147–148 |
| 189 | N | CH₃ | H | CH₃ | S | — | O | NH |  | 119–120 |
| 190 | N | CH₃ | H | CH₃ | S | — | O | NH | 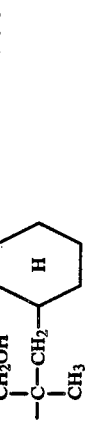 | 107–108 |
| 191 | N | CH₃ | H | CH₃ | S | — | O | NH |  | 179–180 |

-continued

| | | | | | | | | | | mp |
|---|---|---|---|---|---|---|---|---|---|---|
| 192 | N | CH₃ | H | CH₃ | S | — | O | NH | ![cyclohexyl with CH₃ and CH₂—CH₂—CH(CH₃)OH] | 124–125 |
| 193 | N | CH₃ | H | CH₃ | S | — | O | NH | CH₃—C(CH₃)₂—CH₂—N(CH₃)₂ | 96–97 |
| 194 | N | CH₃ | H | CH₃ | S | — | O | NH | CH₃—C(CH₃)₂—CH₂—(piperidinyl) | 108–110 |
| 195 | N | CH₃ | H | CH₃ | S | — | O | NH | CH₃—C(CH₃)₂—CH₂—(morpholinyl) | 150–152 |
| 196 | N | CH₃ | H | CH₃ | S | — | O | NH | CH₃—C(CH₃)₂—CH₂—N(CH₃)₃⁺ J⁻ | 66 (Decomp.) |
| 197 | N | CH₃ | H | CH₃ | S | — | O | NH | cyclohexyl-CH₃ | 115–116 |
| 198 | N | CH₃ | H | CH₃ | S | — | O | NH | H₃C—CH—CH₂—CH(OC₂H₅)₂; CH₃—C(CH₃)₂—COOH | 246–248 |
| 199 | N | CH₃ | H | CH₃ | S | — | O | NH | CH₃—C(=O)(CH₃)₂—C(O)—OC₂H₅ | 158–160 |

| No. | | | | | | | | R | m.p. |
|---|---|---|---|---|---|---|---|---|---|
| 200 | N | CH₃ | H | CH₃ | S | — | O | NH | cyclopentane-1-CH₃-1-COOC₂H₅ | 147-148 |
| 201 | N | CH₃ | H | CH₃ | S | — | O | NH | -C(CH₃)(CN)(CH₃) | 197 |
| 202 | N | CH₃ | H | CH₃ | S | — | O | NH | -C(CH₃)(CN)(C₂H₅) | 169-170 |
| 203 | N | CH₃ | H | CH₃ | S | — | O | NH | -C(CH₃)(C₃H₇)(CN) | |
| 204 | N | CH₃ | H | CH₃ | S | — | O | NH | -C(CH₃)(CH(CH₃)₂)(CN) | |
| 205 | N | CH₃ | H | CH₃ | S | — | O | NH | -C(CH₃)(C₃H₇)(CN) | 176-177 |
| 206 | N | CH₃ | H | CH₃ | S | — | O | NH | -C(CH₃)(C₆H₅)(CN) | <260 |
| 207 | N | CH₃ | H | CH₃ | S | — | O | NH | -C(CH₃)(CONH₂)(CH₃) | |
| 208 | N | CH₃ | H | CH₃ | S | — | O | NH | -C(CH₃)(CONHCH₃)(CH₃) | 184-186 |

| | | | | | | | | |
|---|---|---|---|---|---|---|---|---|
| 209 | N | CH₃ | H | CH₃ | S | — | O | NH | CH₃-C(CH₃)-C(=O)-N(CH₃)₂ | 220-222 |
| 209a | N | CH₃ | H | CH₃ | S | — | O | NH | CH₃-C(CH₃)-C(=O)-NH-C₆H₅ | 108-110 |
| 210 | N | CH₃ | H | CH₃ | S | — | O | NH | CH₃-C(C₂H₅)-CONH₂ | 155-156 |
| 211 | N | CH₃ | H | CH₃ | S | — | O | NH | C₂H₅-C(C₂H₅)-CONH₂ | 189-190 |
| 212 | N | CH₃ | H | CH₃ | S | — | O | NH | CH₃-C(CH₃-CH-C₂H₅)(CONH₂)-CH₂ | 183 |
| 213 | N | CH₃ | H | CH₃ | S | — | O | NH | C₃H₇-C(C₃H₇)-CONH₂ | 76-77 |
| 214 | N | CH₃ | H | CH₃ | S | — | O | NH | 3-Cl-C₆H₄ | 141-142 |

| No. | | | | | | | | Ar/R | m.p. |
|---|---|---|---|---|---|---|---|---|---|
| 215 | N | CH₃ | H | CH₃ | S | — | O | NH | 4-Cl-C₆H₄ | 165-166 |
| 216 | N | CH₃ | H | CH₃ | S | — | O | NH | 3,5-Cl₂-C₆H₃ | 151-152 |
| 217 | N | CH₃ | H | CH₃ | S | — | O | NH | 3-CH₃-C₆H₄ | 153-154 |
| 218 | N | CH₃ | H | CH₃ | S | — | O | N—CH₃ | C₆H₅ | 124-125 |
| 219 | N | CH₃ | H | CH₃ | S | — | O | N—CH₃ | cyclohexyl | 155-156 |
| 220 | N | CH₃ | H | CH₃ | S | — | O |  | 3-methylcyclohexyl |  |
| 221 | N | CH₃ | H | CH₃ | S | — | O |  | 2-methylpyrrolidinyl |  |
| 222 | N | CH₃ | H | CH₃ | S | — | O | NOH | 2-methylpiperidinyl, H | 190-192 |
| 222a | N | CH₃ | H | CH₃ | S | — | O | NOH | —C(CH₃)₃ | 156-158 |
| 223 | N | CH₃ | H | CH₃ | S | — | O | NOCH₃ | H | 160-162 |
| 223a | N | CH₃ | H | CH₃ | S | — | S | O | C₂H₅ | 70-71 |

TABLE-continued

| No. | | | | | | | | | | | mp |
|---|---|---|---|---|---|---|---|---|---|---|---|
| 224 | N | CH₃ | H | CH₃ | S | — | S | S | O | —C—(CH₃)₃ | |
| 225 | N | CH₃ | H | CH₃ | S | — | S | S | O | —C(CH₃)(C≡CH)(CH₃) | |
| 226 | N | CH₃ | H | CH₃ | S | — | S | S | O | —C(CH₃)(CN)(CH₃) | |
| 227 | N | CH₃ | H | CH₃ | S | — | S | S | O | cyclopentyl-CH₃ | |
| 228 | N | CH₃ | H | CH₃ | S | — | S | S | O | cyclohexyl-CH₃ | |
| 229 | N | CH₃ | H | CH₃ | S | — | S | S | S | —C(CH₃)₃ | |
| 230 | N | CH₃ | H | CH₃ | S | — | S | S | S | cyclopentyl-CH₃ | |
| 231 | N | CH₃ | H | CH₃ | S | — | S | S | S | cyclohexyl-CH₃ | |
| 232 | N | CH₃ | H | CH₃ | S | — | S | S | NH | —C(CH₃)(C₂H₅)(CH₃) | 102–103 |
| 233 | N | CH₃ | H | CH₃ | S | — | S | S | NH | —C(CH₃)(CH₂—C(CH₃)₃)(CH₃) | 81–82 |

-continued

| No. | | | | | | | | | m.p. (°C) |
|---|---|---|---|---|---|---|---|---|---|
| 234 | N | CH$_3$ | H | CH$_3$ | S | — | S | NH | 1-methylcyclopropyl | 121-122 |
| 235 | N | CH$_3$ | H | CH$_3$ | S | — | S | NH | 1-methylcyclopentyl | 101-102 |
| 236 | N | CH$_3$ | H | CH$_3$ | S | — | S | NH | 1-methylcyclohexyl | 99-100 |
| 237 | N | CH$_3$ | H | CH$_3$ | S | — | S | NH | —CH(CH$_3$)—C$_6$H$_5$ | 45-46 |
| 238 | N | CH$_3$ | H | CH$_3$ | S | — | S | NH | 3-Cl-C$_6$H$_4$— | 173-174 |
| 239 | N | CH$_3$ | H | CH$_3$ | S | — | S | NH | 4-Cl-C$_6$H$_4$— | 193-194 |
| 240 | N | CH$_3$ | H | CH$_3$ | S | — | S | NCH$_3$ | —C(CH$_3$)$_3$ | |
| 241 | N | CH$_3$ | H | CH$_3$ | S | — | S | N—C(CH$_3$)$_3$ | O | |
| 242 | N | CH$_3$ | H | CH$_3$ | S | — | S | O | —C(CH$_3$)$_3$ | oil |
| 243 | N | CH$_3$ | H | CH$_3$ | S | — | S | | N—CH$_2$ / O—CH—CH$_3$ ; N—C(CH$_3$)$_2$ / O—CH$_2$ | 68-69 |
| 244 | N | CH$_3$ | H | CH$_3$ | S | — | S | | N—CH—CH(CH$_3$)$_2$ / O—CH$_2$ | oil |

-continued

| | | | | | | | |
|---|---|---|---|---|---|---|---|
| 245 | N | CH₃ | H | CH₃ | S | — | ![structure with N-C(CH₃)(CH₂OH)-O-CH₂] | 124-125 |
| 246 | N | CH₃ | H | CH₃ | S | — | ![structure with cyclohexyl-CH, N-C(CH₃)(CH₂)-O-CH₂] | oil |
| 246a | N | CH₃ | H | CH₃ | S | — | ![structure with cyclohexyl, N-O-CH₂] | 103 |
| 246b | N | CH₃ | H | CH₃ | S | — | ![structure N-C(CH₃)-O-C(CH₃)(CH₃)] | 114 |
| 246c | N | CH₃ | H | CH₃ | S | — | ![structure N-CH₂-O-C(C₄H₉)(CH₃)] | oil |
| 246d | N | CH₃ | H | CH₃ | S | — | ![structure N-CH₂-O-C(CH₃)(CH₃9)] wait CH₃₉→CH₃ | 82 |
| 246e | N | CH₃ | H | CH₃ | S | — | ![structure N-CH(CH₃)-O-C(CH₃)(CH₃)] | 74 |
| 247 | N | CH₃ | H | CH₃ | S | — | ![structure N-CH₂-CH₂-O-CH₂] | 122-123 |

-continued

| | | | | | | | m.p. (°C) |
|---|---|---|---|---|---|---|---|
| 248 | N | CH₃ | H | CH₃ | S | — | N—CH₂—CH₂—O—CH₃ | 94-95 |
| 249 | N | CH₃ | H | CH₃ | S | — | N(CH₃)—CH(CH₃)—CH₂—O—CH₃ | 96-97 |
| 249a | N | CH₃ | H | CH₃ | S | — | N—CH₂—C(CH₃)₂—O—CH₃ | 101 |
| 250 | N | CH₃ | H | CH₃ | S | — | N(CH₃)—C(CH₃)₂—CH₂—O—CH₃ | 98-99 |
| 250a | N | CH₃ | H | CH₃ | S | — | N(CH₃)—CH₂—C(CH₃)₂—O—CH₃ | oil |
| 250b | N | CH₃ | H | CH₃ | S | 2-CH₃ | N(CH₃)—CH₂—CH₂—C(O)CH₃ | oil |
| 251  | N | CH₃ | H | CH₃ | S | —   | SCH₃       | C(CH₃)₃              | 88-90 |
| 251a | N | CH₃ | H | CH₃ | S | N   | SC₂H₅      | 65-67                | 69-70 |
| 251b | N | CH₃ | H | CH₃ | S | —   | SCH₂—CH=CH₂| C(CH₃)₃              | 78 |
| 251c | N | CH₃ | H | CH₃ | S | —   | S—C₃H₇-i   | C(CH₃)₃              | oil |
| 251d | N | CH₃ | H | CH₃ | S | —   | S—CH₂—CH=CH₂ | C(CH₃)₂—C₂H₅      | 89-90 |
| 251e | N | CH₃ | H | CH₃ | S | 3-CH₃ | S—CH₂—CH=CH₂ | C(CH₃)₂—CH(CH₃)₂ | |

4,871,387

-continued

| | | | | | | | | |
|---|---|---|---|---|---|---|---|---|
| 252 | N | CH₃ | H | CH₃ | S | — | ![N-C(CH₃)(CH₃)-S ring]  CH₃  CH₃ / N—S | 115–117 |
| 253 | N | CH₃ | H | CH₃ | S | — | CH₃ / N=S | 63–64 |
| 254 | N | CH₃ | H | CH₃ | S | — | CH(CH₃)₂ / N=S | |
| 255 | N | CH₃ | H | CH₃ | S | — | C(CH₃)₃ / N=S | 118–119 |
| 256 | N | CH₃ | H | CH₃ | S | — | CH₃ / N=S \ CH₃ | |
| 257 | N | CH₃ | H | CH₃ | S | — | NH / N—CH₃ | C(CH₃)₃ |
| 258 | N | CH₃ | H | CH₃ | S | — | NH / N—C(CH₃)₃ | C(CH₃)₃ |
| 259 | N | CH₃ | H | CH₃ | S | — | NCH₃ / NCH₃ | CH₃ |
| 260 | N | CH₃ | H | CH₃ | S | — | CH₃ \ N—N—H / CH₃ | |

| | | | | | | |
|---|---|---|---|---|---|---|
| 261 | N | CH₃ | H | CH₃ | S | — | 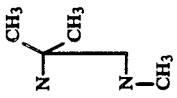 | |
| 261a | N | CH₃ | H | CH₃ | S | — | 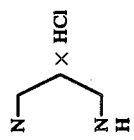 | <230° C. |

| No. | | | | | | | | | | mp |
|---|---|---|---|---|---|---|---|---|---|---|
| 262 | N | CH₃ | H | CH₃ | S | — | CH₃\N=⟨ ⟩NH | | | |
| 263 | N | CH₃ | H | CH₃ | S | — | ⟨ ⟩N-H | | | |
| 264 | N | CH₃ | H | CH₃ | S | — | N=⟨ ⟩N—C(CH₃)₃ | | | |
| 264 | N | CH₃ | H | CH₃ | S | — | N—OH | O | C(CH₃)₃ | 174 |
| 265 | N | CH₃ | H | CH₃ | S | — | N—OH | S | C(CH₃)₃ | |
| 266 | N | CH₃ | H | CH₃ | S | — | N—OH | NH | H | |
| 267 | N | CH₃ | H | CH₃ | S | — | N—OH | NH | C(CH₃)₃ | |
| 268 | N | CH₃ | H | CH₃ | S | — | NOCH₃ | O | C(CH₃)₃ | |
| 269 | N | CH₃ | H | CH₃ | S | — | NOCH₃ | S | C(CH₃)₃ | |
| 270 | N | CH₃ | H | CH₃ | S | — | NOCH₃ | NH | C(CH₃)₃ | |
| 271 | N | CH₃ | H | CH₃ | S | — | N—O—C(=N)—CH₃ | O | | 93–95 |
| 272 | N | CH₃ | H | CH₃ | S | — | N—O—C(=N)—CH(CH₃)₂ | O | | |
| 273 | N | CH₃ | H | CH₃ | S | — | NO—C(=N)—C(CH₃)₃ | O | | 100–102 |
| 274 | N | CH₃ | H | CH₃ | S | 2-F | O | NH | —C(CH₃)₃ | 138–139 |
| 275 | N | CH₃ | H | CH₃ | S | 2-Cl | O | NH | —C(CH₃)₃ | 175–176 |
| 276 | N | CH₃ | H | CH₃ | S | 3-Cl | O | NH | —C(CH₃)₃ | 161–162 |
| 277 | N | CH₃ | H | CH₃ | S | 3-Cl | S | NH | —C(CH₃)₃ | |
| 278 | N | CH₃ | H | CH₃ | S | 3-Br | O | NH | —C(CH₃)₃ | |
| 279 | N | CH₃ | H | CH₃ | S | 3,5-Cl₂ | O | NH | —C(CH₃)₃ | |
| 280 | N | CH₃ | H | CH₃ | S | 2-OCH₃ | O | NH | —C(CH₃)₃ | |
| 281 | N | CH₃ | H | CH₃ | S | 3-OCH₃ | O | NH | —C(CH₃)₃ | |
| 282 | N | CH₃ | H | CH₃ | S | 3-NH—C(=O)—CH₃ | O | NH | —C(CH₃)₃ | 181 |
| 283 | N | CH₃ | H | CH₃ | S | 3-NH—C(=O)—C(CH₃)₃ | O | NH | —C(CH₃)₃ | 181–182 |
| 284 | N | CH₃ | H | CH₃ | S | 3—N(COOCH₃)₂ | O | NH | —C(CH₃)₃ | 221 |

-continued

| No. | Z | R | R' | R'' | X | Subst. | | Y | Z' | mp |
|---|---|---|---|---|---|---|---|---|---|---|
| 285 | N | CH₃ | H | CH₃ | S | 3-NH-C(=O)-OC₆H₅ | O | NH | —C(CH₃)₃ | 180 |
| 286 | N | CH₃ | H | CH₃ | S | 2-CH₃ | O | NH | —C(CH₃)₃ | 75–76 |
| 287 | N | CH₃ | H | CH₃ | S | 3-CH₃ | O | O | —C(CH₃)₃ | 177–178 |
| 288 | N | CH₃ | H | CH₃ | S | 3-CH₃ | O | NH | —C(CH₃)₃ | 177–178 |
| 289 | N | CH₃ | Cl | CH₃ | S | — | O | NH | —C(CH₃)₃ | 98 |
| 289a | N | CH₃ | Cl | NH₂ | S | — | O | NH | —C(CH₃)₃ | 164 |
| 290 | N | CH₃ | Br | CH₃ | S | — | O | NH | —C(CH₃)₃ | |
| 291 | N | CH₃ | H | CF₃ | S | — | O | NH | —C(CH₃)₃ | |
| 292 | N | CH₃ | H | C₂H₅ | S | — | O | NH | —C(CH₃)₃ | |
| 293 | N | CH₃ | H | C₃H₇ | S | — | O | NH | —C(CH₃)₃ | |
| 294 | N | CH₃ | H | C₄H₉ | S | — | O | NH | —C(CH₃)₃ | |
| 295 | N | C₂H₅ | H | C₂H₅ | S | — | O | NH | —C₂H₅ | 74–76 |
| 296 | N | CH₃ | CH₃ | CH₃ | S | — | O | O | —C(CH₃)₃ | 66–67 |
| 297 | N | CH₃ | CH₃ | CH₃ | S | — | O | O | —C(CH₃)₃ | |
| 297a | N | CH₃ | CH₃ | CH₃ | S | — | O | O | —C(CH₃)(C₂H₅)CH₃ | 65 |
| 297b | N | CH₃ | CH₃ | CH₃ | S | — | O | O | —CH₂—CH₂—C(CH₃)₂—O—C₂H₅ | oil |
| 297c | N | CH₃ | CH₃ | CH₃ | S | — | O | O | —CH₂—C(CH₃)₂—O—CH₃ | 83 |
| 297d | N | CH₃ | CH₃ | CH₃ | S | 3-CH₃ | O | O | —CH₂—C(CH₃)₂—O—C₂H₅ | oil |
| 297e | N | CH₃ | CH₃ | CH₃ | S | — | O | O | —C(CH₃)₃ | 82 |
| 298 | N | CH₃ | CH₃ | CH₃ | S | — | O | NH | —C(CH₃)(C₂H₅)CH₃ | 186–188 |
| 299 | N | CH₃ | CH₃ | CH₃ | S | — | O | NH | —C(CH₃)(CH(CH₃)₂)CH₃ | 184–186 |
| 300 | N | CH₃ | CH₃ | CH₃ | S | — | O | NH | —C(CH₃)(C(CH₃)₃)CH₃ | 144–145 |
| 301 | N | CH₃ | CH₃ | CH₃ | S | — | O | NH | —C(CH₃)₂—C(CH₃)₃ | 148–149 |
| 302 | N | CH₃ | CH₃ | CH₃ | S | — | O | NH | —C(CH₃)(C≡CH)CH₃ | 172–174 |

-continued
| No. | | | | | | | | | m.p. |
|---|---|---|---|---|---|---|---|---|---|
| 303 | N | CH₃ | CH₃ | CH₃ | S | — | O | NH |  | 147-148 |
| 304 | N | CH₃ | CH₃ | CH₃ | S | — | O | NH | —C(CH₃)(CN)—C₂H₅ | 198-200 |
| 305 | N | CH₃ | CH₃ | CH₃ | S | — | S | NH | —C(CH₃)₃ | 179-180 |
| 306 | N | CH₃ | C₂H₅ | CH₃ | S | — | O | NH | —C(CH₃)₃ | 103-104 |
| 307 | N | CH₃ | —(CH₂)₃— | | S | — | O | NH | —C(CH₃)₃ | 197-198 |
| 308 | N | CH₃ | —(CH₂)₄— | | S | — | O | NH | —C(CH₃)₃ | |
| 309 | N | CH₃ | —CH=CH—CH=CH— | | S | — | O | NH | —C(CH₃)₃ | |
| 310 | N | CH₃ | H | CH₃ | S | — | O | NH | 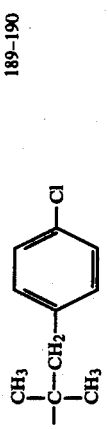 | 189-190 |
| 310a | N | CH₃ | H | CH₃ | S | 3-Cl | O | S | —C(CH₃)₃ | 43 |
| 311 | N | CH₃ | H | CH₃ | S | 3-Cl | O | NH |  | 193-194 |
| 312 | N | CH₃ | H | CH₃ | S | 3-Cl | O | NH | CH₃—C(C₂H₅)—CH₃ | 120 |
| 313 | N | CH₃ | H | CH₃ | S | 3-Cl | O | NH | CH₃—C(CH(CH₃)₂)—CH₃ | 91 |
| 314 | N | CH₃ | H | CH₃ | S | 3-Cl | O | NH | 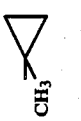 | 201 |
| 315 | N | CH₃ | H | CH₃ | S | 3-Cl | O | NH | 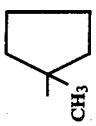 | 162 |

| No. | | | | | | | | | R | mp |
|---|---|---|---|---|---|---|---|---|---|---|
| 316 | N | CH₃ | H | CH₃ | S | 3-Cl | S | NH | ▽ (cyclopropyl) | 113 |
| 317 | N | CH₃ | H | CH₃ | S | 3-Cl | S | NH | -C(CH₃)(C₂H₅)CH₃ | 104 |
| 318 | N | CH₃ | H | CH₃ | S | 3-Cl | S | NH | -C(CH₃)(CH(CH₃)₂)CH₃ | 108 |
| 319 | N | CH₃ | H | CH₃ | S | 3-Cl | S | NH | 1-methylcyclopropyl | 113 |
| 320 | N | CH₃ | H | CH₃ | S | 3-Cl | S | NH | 1-methylcyclopentyl | 104 |
| 321 | N | CH₃ | H | CH₃ | S | 3-F | O | NH | -C(CH₃)₃ | 175 |
| 322 | N | CH₃ | H | CH₃ | S | 3-F | S | NH | -C(CH₃)₃ | 133 |
| 323 | N | CH₃ | H | CH₃ | S | 2-Cl | O | O | -C(CH₃)₃ | 65-66 |
| 324 | N | CH₃ | H | CH₃ | S | 2-Cl | O | O | -C(CH₃)(CH₃)CH₂-C≡C-Cl | oil |
| 325 | N | CH₃ | H | CH₃ | S | 2-Cl | O | O | -C(CH₃)(C≡C-Cl)CH₃ | oil |
| 326 | N | CH₃ | H | CH₃ | S | 2-Cl | O | NH | -C(CH₃)(C₂H₅)CH₃ | 106-107 |
| 327 | N | CH₃ | H | CH₃ | S | 2-Cl | O | NH | -C(CH₃)(C≡CH)CH₃ | 142-143 |

-continued

| No. | | | | | | | | | m.p. |
|---|---|---|---|---|---|---|---|---|---|
| 328 | N | CH₃ | H | CH₃ | S | | O | NH | —C(CH₃)₂—CN | 144-145 |
| 329 | N | CH₃ | H | CH₃ | S | 2-Cl | S | NH | —C(CH₃)₃ | 123 |
| 330 | N | CH₃ | H | CH₃ | S | 2-Cl | O | O | —C(CH₃)₃ | 99 |
| 331 | N | CH₃ | H | CH₃ | S | 3-Cl | O | O | —C(CH₃)₂—CH₂—C≡C—Cl | 53 |
| 332 | N | CH₃ | H | CH₃ | S | 3-Cl | O | O | —C(CH₃)₂—C≡C—Cl | 77 |
| 333 | N | CH₃ | H | CH₃ | S | 3-CH₃ | O | O | —C(CH₃)₂—CH₂—C≡C—Cl | oil |
| 334 | N | CH₃ | H | CH₃ | S | 3-CH₃ | O | O | —C(CH₃)₂—C≡C—Cl | 70-71 |
| 335 | N | CH₃ | H | CH₃ | S | 3-CH₃ | O | O | cyclopentyl-CH₃ | 59-60 |
| 336 | N | CH₃ | H | CH₃ | S | 3-CH₃ | O | S | —C(CH₃)₃ | 64-65 |
| 337 | N | CH₃ | H | CH₃ | S | 3-CH₃ | O | NH | —C(CH₃)₂—C₂H₅ | 94-95 |
| 338 | N | CH₃ | H | CH₃ | S | 3-CH₃ | O | NH | —C(CH₃)₂—CH(CH₃)₂ | 106 |
| 339 | N | CH₃ | H | CH₃ | S | 3-CH₃ | O | NH | cyclopropyl-CH₃ | 188 |

-continued

| No. | | | | | | | | | | mp |
|---|---|---|---|---|---|---|---|---|---|---|
| 340 | N | CH$_3$ | H | CH$_3$ | S | 3-CH$_3$ | O | NH | (1-methylcyclopentyl) | 133–134 |
| 341 | N | CH$_3$ | H | CH$_3$ | S | 3-CH$_3$ | O | NH | —C(CH$_3$)(CH$_3$)—C≡C—H | 123–124 |
| 342 | N | CH$_3$ | H | CH$_3$ | S | 3-CH$_3$ | O | NH | —C(CH$_3$)(CH$_3$)—CN | 207–208 |
| 343 | N | CH$_3$ | H | CH$_3$ | S | 3-CH$_3$ | S | NH | —C(CH$_3$)$_3$ | 169–170 |
| 344 | N | CH$_3$ | H | CH$_3$ | S | 3-CH$_3$ | S | NH | —C(CH$_3$)(C$_2$H$_5$)—CH$_3$ | 126–127 |
| 345 | N | CH$_3$ | H | CH$_3$ | S | 3-CH$_3$ | S | NH | —C(CH$_3$)(CH(CH$_3$)$_2$)—CH$_3$ | 112–113 |
| 346 | N | CH$_3$ | H | CH | S | 3-CH$_3$ | S | NH | (1-methylcyclopropyl) | 109 |
| 347 | N | CH$_3$ | CH$_3$ | CH$_3$ | S | 2-Cl | O | O | —C(CH$_3$)$_3$ | 95 |
| 348 | N | CH$_3$ | CH$_3$ | CH$_3$ | S | 2-Cl | O | NH | —C(CH$_3$)$_3$ | 145 |
| 349 | N | CH$_3$ | CH$_3$ | CH$_3$ | S | 2-Cl | S | NH | —C(CH$_3$)$_3$ | 124–125 |
| 350 | N | CH$_3$ | CH$_3$ | CH$_3$ | S | 3-Cl | O | O | —C(CH$_3$)$_3$ | 60 |
| 351 | N | CH$_3$ | CH$_3$ | CH$_3$ | S | 3-Cl | O | S | —C(CH$_3$)$_3$ | 58 |
| 352 | N | CH$_3$ | CH$_3$ | CH$_3$ | S | 3-Cl | O | NH | —C(CH$_3$)$_3$ | 196 |
| 353 | N | CH$_3$ | CH$_3$ | CH$_3$ | S | 3-Cl | O | NH | —C(CH$_3$)(C$_2$H$_5$)—CH$_3$ | 156 |
| 354 | N | CH$_3$ | C$_2$H$_5$ | CH$_3$ | S | — | O | O | —C(CH$_3$)$_3$ | 50 |

Preparation of the starting compounds

Example XXV-1

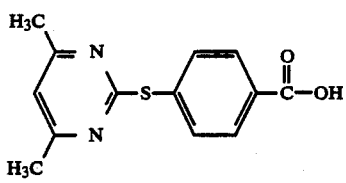

144 g (0.5 mol) of ethyl 4-(4,6-dimethyl-pyrimidyl-2-mercapto)-benzoate are suspended in 380 ml of ethanol. The solution of 40 g (1 mol) of sodium hydroxide in a little water is added dropwise at room temperature and the mixture allowed to stand for 2 hours at room temperature. Water is then added until a clear solution is produced and this is warmed for a further 30 minutes at 50° C. The solution is then diluted using 1 liter of water and acidified using hydrochloric acid. The crystals which have precipitated are filtered off under suction and dried.

123 g (94.6% of theory) of 4-(4,6-dimethylpyrimidyl-2-mercapto)-benzoic acid with melting point 179°-180° C. (recrystallization from toluene) are obtained.

In analogous fashion, the following are obtained:

Example XXV-2

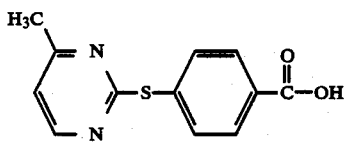

Melting point 185–186° C. (recrystallization from ethyl acetate)

Example XXV-3

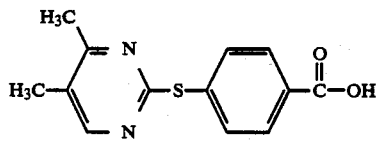

Melting point 197–198° C. (recrystallization from ethanol)

Example XXV-4

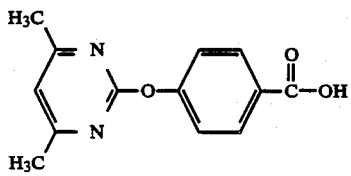

Melting point 170–171° C. (recrystallization from ethyl acetate)

Example XIII-1

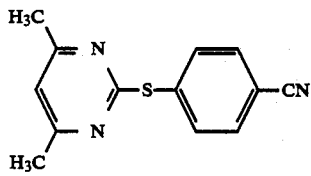

67.5 g (0.5 mol) of 4-mercapto-benzonitrile are dissolved in 250 ml of N-methylpyrrolidone. 28 g (0.5 mol) of powdered potassium hydroxide are added in portions at room temperature with stirring and, after 30 minutes, 71.2 g (0.5 mol) of 2-chloro-4,6-dimethyl-pyrimidine are added. The mixture is gradually heated to 120° C. and stirred for a further 4 hour at this temperature. After cooling to room temperature the mixture is diluted with 1.5 liters of water. The crystals which deposit are filtered off under suction and dried.

110 g (91.2% of theory) of 4-(4,6-dimethyl-pyrimidyl-2-mercapto)-benzonitrile with melting point 90° C. (recrystallization from petroleum ether) are obtained.

Example XVI-1

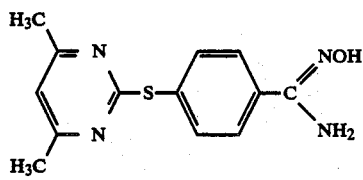

7.65 g (0.11 mol) of hydroxylammonium chloride are dissolved in a very little water. While cooling with ice, a solution of 6.16 g (0.11 mol) of potassium hydroxide in ethanol is added. After standing for 1 hour, the potassium chloride which has precipitated is filtered off under suction and 24.1 g (0.1 mol) of 4-(4,6-dimethyl-pyrimidyl-2-mercapto)-benzonitrile are added in portions to the solution at room temperature. This mixture is stirred for 15 hours at 60° C. to 80° C. and subsequently concentrated in vacuo. The residue is dissolved in dilute hydrochloric acid, the solution is filtered and neutralized using ammonia. The crystals which have precipitated are filtered off under suction, washed with water and dried in air.

21.4 g (78% of theory) of 4-(4,6-dimethyl-pyrimidyl-2-mercapto)-benzamide oxime with melting point 174° C. (decomp.) (after recrystallization from a little butanol) are obtained.

Example A

Post-emergence test

Solvent: 5 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

Test plants which have a height of 5–15 cm are sprayed with the preparation of the active compound in such a way as to apply the particular amounts of active compound desired per unit area. The concentration of the spray liquor is so chosen that the particular amounts of active compound desired are applied in 2,000 l of water/ha. After three weeks, the degree of damage to the plants is rated in % damage in comparison to the development of the untreated control. The figures denote:

0%=no action (like untreated control)
100%=total destruction

The compounds according to the preparation examples: 3,4,5,8,71,102,166,175,176,202 and 219, for example, show very good activity in the selective combating of monocotyledon and dicotyledon weeds in monocotyledon crops such as, for example, barley, wheat and maize in this test.

Example B

Defoliation and desiccation of the leaves of cotton
Solvent: 30 parts by weight of dimethylformamide
Emulsifier: 1 part by weight of polyoxyethylene sorbitane monolaurate To produce a suitable preparation of active compound, 1 part by weight of active compound is mixed with the stated amounts of solvent and emulsifier and the mixture is made up to the desired concentration with water.

Cotton plants are grown in a greenhouse until the 5th secondary leaf has unfolded completely. In this stage, the plants are sprayed with the preparations of active compound until dripping wet. After 1 week, the shedding of leaves and the desiccation of the leaves are rated, in comparison with the control plants.

The figures of merit have the following meanings:

0 denotes no desiccation of the leaves, no shedding of leaves

+ denotes slight desiccation of the leaves, slight shedding of leaves

++ denotes severe desiccation of the leaves, severe shedding of leaves

+++ denotes very severe desiccation of the leaves, very severe shedding of leaves.

The compounds according to preparation examples: 4, 167 and 202, for example, show a very good activity in this test.

It is understood that the specification and examples are illustrative but not limitative of the present invention and that other embodiments within the spirit and scope of the invention will suggest themselves to those skilled in the art.

What is claimed is:

1. A pyrimidyl-oxy- or -thio-benzoic acid derivative of the formula

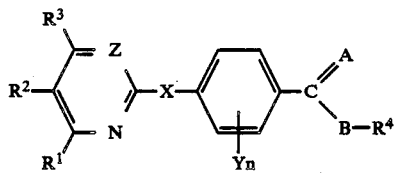

in which $R^1$, $R^2$ and $R^3$, each independently represent hydrogen; alkyl having 1 to 6 carbon atoms; alkenyl having 2 to 6 carbon atoms; unsubstituted $C_1$–$C_4$-alkoxy or $C_1$–$C_4$-alkoxy which is substituted by $C_2$–$C_4$-alkenyl or $C_1$–$C_2$-alkoxy; alkylamino or dialkylamino having 1 to 4 carbon atoms in each of the individual alkyl moieties, where, in the case of dialkylamino, the alkyl substituents can form a 5- to 6-membered heterocyclic ring with the nitrogen atom to which they are attached said heterocyclics being pyrrolidine, piperidine, morpholine and piperazine; amino; alkenylamino or dialkenylamino having 3 to 4 carbon atoms in each of the individual alkenyl moieties; or trifluoromethyl; or $R^1$ and $R^2$ and $R^3$ together represent a 5- or 6-membered saturated or unsaturated carbocyclic ring; with the proviso that at least one of the radicals $R^1$, $R^2$, or $R^3$ represents alkyl having 1 to 6 carbon atoms, trifluoromethyl or forms a part of the fused 5- or 6-membered carbocyclic ring, Z represents a nitrogen atom, X represents oxygen or sulphur, Y represents fluorine; chlorine; bromine; iodine; nitro; cyano; or amino; alkyl, alkoxy, haloalkyl, alkylcarbonylamino or alkoxycarbonylamino, in each case with 1 to 4 carbon atoms in the alkyl moiety and, in the case of haloalkyl having 1 to 5 halogen atoms, where halogen represents fluorine, chlorine, bromine and iodine; or phenoxycarbonylamino; where the Y's can be identical or different;

n represents an integer 0, 1, 2, 3 or 4,

A represents oxygen, sulphur, a radical $R^5$—N= or a radical $R^6$O—N=, where $R^5$ represents hydrogen; alkyl, hydroxyalkyl or alkoxyalkyl, in each case having 1 to 4 carbon atoms in the individual alkyl moieties; alkenyl having 3 to 4 carbon atoms; unsubstituted cycloalkyl having 3 to 7 carbon atoms or cycloalkyl having 3 to 7 carbon atoms which is substituted by fluorine, chlorine, bromine, $C_1$–$C_4$-alkyl or $C_1$–$C_4$-alkoxy; unsubstituted phenyl, benzyl or phenethyl or phenyl, benzyl or phenethyl which are substituted on the phenyl by fluorine, chlorine, bromine, iodine, $C_1$–$C_4$-alkyl, $C_1$–$C_4$-alkoxy, $C_1$–$C_4$-alkylthio, $C_1$–$C_4$-alkylsulphinyl, $C_1$–$C_4$-alkylsulphonyl, or halo-$C_1$–$C_4$-alkylsulphonyl, $R^6$ represents hydrogen or alkyl having 1 to 4 carbon atoms or alkenyl having 3 to 4 carbon atoms;

B represents oxygen, sulphur or a radical

where $R^7$ represents hydrogen; unsubstituted alkyl having 1 to 4 carbon atoms or alkyl having 1 to 4 carbon atoms which is substituted by fluorine, chlorine, bromine, iodine, cyano or a radical —D—$R^9$; or alkenyl having 2 to 4 carbon atoms, where D represents oxygen, sulphur, sulphinyl or sulphonyl and $R^9$ represents hydrogen; alkyl having 1 to 4 carbon atoms; alkenyl having 3 to 4 carbon atoms; unsubstituted phenyl, benzyl or phenethyl or phenyl, benzyl or phenethyl which are substituted on the phenyl by fluorine, chlorine, bromine, $C_1$–$C_4$-alkyl or $C_1$–$C_4$-alkoxy;

$R^4$ represents unsubstituted alkyl having 4 to 12 carbon atoms or substituted alkyl having 4 to 12 carbon atoms; unsubstituted or substituted alkenyl having up to 12 carbon atoms or unsubstituted or substituted alkinyl having up to 12 carbon atoms; wherein the alkyl, alkenyl and alkinyl substituents are selected from the group consisting of fluorine; chlorine; nitro; cyano; alkoximino having 1 to 4 carbon atoms in the alkyl moiety; unsubstituted cycloalkyl having 3 to 6 carbon atoms, or cycloalkyl having 3 to 6 carbon atoms which is substituted by $C_1$–$C_4$-alkyl, fluorine or chlorine; phenyl or phenyl which is substituted by fluorine, chlorine, bromine, nitro, trifluoromethyl, $C_1$–$C_4$-alkyl, $C_1$–$C_4$-alkoxy, $C_1$–$C_4$-alkylsulphinyl or $C_1$–$C_4$-alkylsulphonyl; a a radical —D—$R^9$; a radical

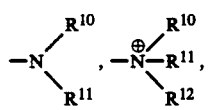

—CO—OR$^{13}$, —CO—NR$^{14}$R$^{15}$, —CS—NR$^{14}$R$^{15}$ or —SO$_2$—NR$^{14}$R$^{15}$;

where

R$^{10}$ represents hydrogen or alkyl having 1 to 4 carbon atoms,

R$^{11}$ represents alkyl having 1 to 4 carbon atoms; alkylsulphonyl having 1 to 4 carbon atoms or phenylsulphonyl or R$^{10}$ and R$^{11}$ together with the nitrogen to which they are attached can form a piperidinyl ring R$^{12}$ represents alkyl having 1 to 4 carbon atoms, R$^{13}$ represents alkyl having 1 to 4 carbon atoms, R$^{14}$ and R$^{15}$, each independently represent hydrogen or alkyl having 1 to 6 carbon atoms or R$^4$, furthermore, represents unsubstituted cycloalkyl having 3 to 8 carbon atoms or cycloalkyl having 3 to 8 carbon atoms which is substituted by fluorine, chlorine, C$_1$-C$_4$-alkyl, C$_1$-C$_4$-alkoxy, C$_2$-C$_4$-alkenyl or halo-C$_1$-C$_4$-alkyl where halo represents 1 to 5 fluorine or chlorine atoms; unsubstituted phenyl or phenyl which is substituted by fluorine, chlorine, bromine, C$_1$-C$_4$-alkyl, halo-C$_1$-C$_4$-alkyl where halo represents 1 to 5 fluorine or chlorine or bromine atoms; or a radical —D$^1$—R$^{17}$, where D$^1$ represents oxygen, sulphur, sulphinyl or sulphonyl, R$^{17}$ represents hydrogen, C$_1$-C$_4$-alkyl, halo-C$_1$-C$_4$-alkyl where halo represents 1 to 5 fluorine or chlorine atoms, C$_3$-C$_4$-alkenyl, a radical —CO—O—C$_1$-C$_4$-alkyl,

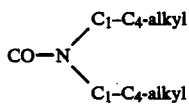

unsubstituted sulphonamide or sulphonamide which is mono- or disubstituted on the nitrogen by C$_1$-C$_4$-alkyl, R$^4$, furthermore, represents an unsubstituted or substituted 5- or 6-membered heterocycle which can contain 1 to 2 identical or different heteroatoms selected form oxygen, nitrogen or sulphur said heterocycles being furanylmethyl, thiazole, pyrrolidine, piperidine, morpholine and wherein the substituents are selected from the group consisting of fluorine, chlorine, bromine, iodine, C$_1$-C$_4$-alkyl, halo-C$_1$-C$_4$-alkyl where halo represents 1 to 5 identical or different fluorine, chlorine, bromine or iodine atoms, amino, alkylamino or dialkylamino having 1 to 4 carbon atoms in each of the individual alkyl moieties, nitro, cyano, the radical —D—R$^9$, the radical —CO—O(C$_1$-C$_4$-alkyl), CO—NH—C$_1$-C$_4$-alkyl or —CO—N(-C$_1$-C$_4$-alkyl)$_2$, or R$^4$, together with R$^5$, R$^6$, R$^7$ or R$^8$ and B forms a 5- or 6-membered ring selected from the group consisting of

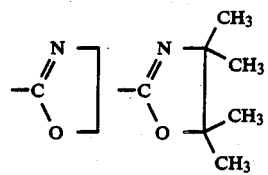

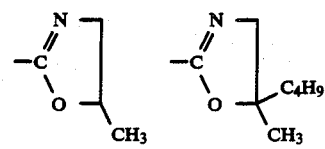

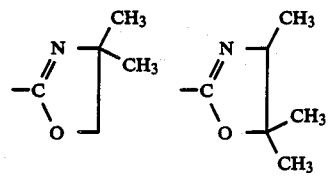

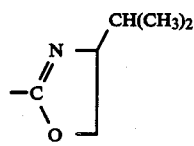

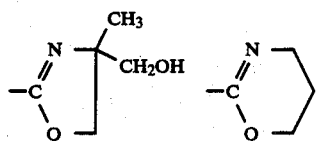

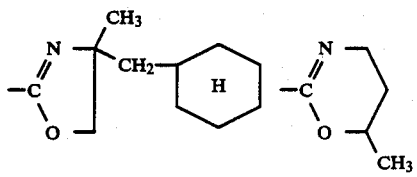

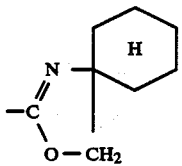

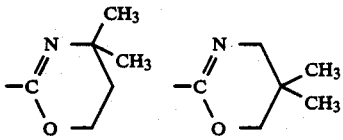

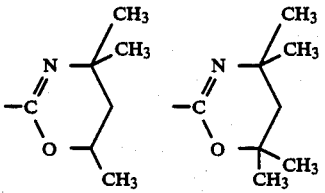

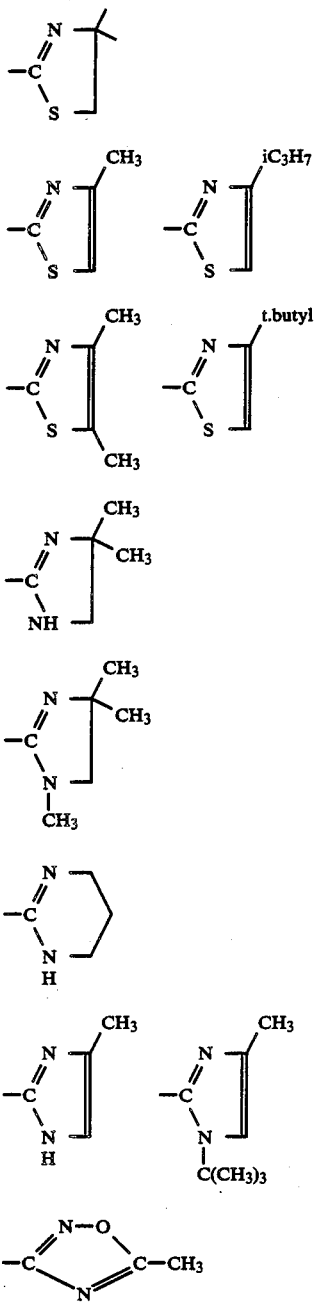

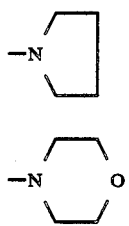

or

R[4] together with A and B, form a 5- or 6-membered ring selected from the group consisting of

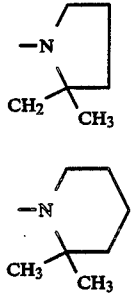

2. A pyrimidyl-oxy- and -thio-benzoic acid derivative according to claim 1, in which $R^1$, $R^2$ and $R^3$, each independently represent hydrogen; alkyl having 1 to 4 carbon atoms; unsubstituted $C_1$–$C_4$-alkoxy or $C_1$–$C_4$-alkoxy which is substituted by $C_2$–$C_4$-alkenyl or $C_1$–$C_2$-alkoxy; alkylamino, dialkylamino having 1 to 4 carbon atoms in each of the individual alkyl moieties; alkenylamino or dialkenylamino having 3 to 4 carbon atoms in each of the individual alkenyl moieties; alkenyl having 2 to 6 carbon atoms or trifluoromethyl; or $R^1$ and $R^2$ or $R^2$ and $R^3$ together represents a saturated or unsaturated 5- or 6-membered carbocyclic ring; with the proviso that at least one of the radicals $R^1$, $R^2$ or $R^3$ represents alkyl having 1 to 4 carbon atoms, trifluoromethyl or forms a part of the fused 5- or 6-membered carbocyclic ring;

Z represents a nitrogen atom;

X represents oxygen or sulphur;

Y represents fluorine; chlorine; bromine; iodine; nitro; amino; alkyl, alkoxy, haloalkyl, alkylcarbonylamino, alkoxycarbonylamino having, in each case, 1 to 3 carbon atoms in the alkyl moiety and in the case of haloalkyl, having 1 to 3 identical or different halo atoms where halo represents fluorine, chlorine, bromine or iodine or phenoxycarbonylamino, where the Y's can be identical or different n represents an integer 0, 1, 2, 3 or 4, A represents oxygen, sulphur, a radical $R^5$—N= or a radical $R^6$O—N=, where $R^5$ represents hydrogen, alkyl or hydroxyalkyl having 1 to 4 carbon atoms in each case; alkenyl having 3 to 4 carbon atoms;

unsubstituted cycloalkyl having 3 to 6 carbon atoms; cycloalkyl having 3 to 6 carbon atoms, which is mono- to tri-substituted, identically or differently, by fluorine, chlorine, bromine, $C_1$–$C_2$-alkyl or $C_1$–$C_2$-alkoxy, unsubstituted phenyl, benzyl or phenethyl or phenyl, benzyl or phenethyl which are mono- to tri-substituted, identically or differently, by fluorine, chlorine, bromine, iodine, $C_1$–$C_2$-alkyl, $C_1$–$C_2$-alkoxy, $C_1$–$C_2$-alkylthio, $C_1$–$C_2$-alkylsulphinyl, $C_1$–$C_2$-alkylsulphonyl or halo-$C_1$–$C_2$-alkylsulphonyl;

$R^6$ represents hydrogen or alkyl having 1 to 4 carbon atoms;

B represents oxygen, sulphur or a radical

—N—R[7], where
R$^7$ represents halogen, unsubstituted alkyl having 1 to 4 carbon atoms; alkyl having 1 to 4 carbon atoms wich is mono- to tri-substituted, identically or differently, by fluorine, chlorine, bromine, iodine, cyano, alkenyl having 2 to 4 carbon atoms or a radical —D—R$^9$.
where
D represents oxygen, sulphur or sulphonyl and
R$^9$ represents hydrogen, unsubstituted alkyl having 1 to 4 carbon atoms or alkenyl having 3 to 4 carbon atoms or alkyl having 1 to 4 carbon atoms or alkenyl having 3 to 4 carbon atoms, which are substituted by phenyl, benzyl or phenethyl or phenyl, benzyl or phenethyl which are substituted on the phenyl by fluorine, chlorine, bromine, C$_1$-C$_2$-alkyl or C$_1$-C$_2$-alkoxy;
R$^4$ represents unsubstituted alkyl having 4 to 10 carbon atoms; unsubstituted alkenyl or alkinyl having up to 10 carbon atoms or substituted alkyl having 4 to 10 carbon atoms, or substituted, alkenyl or alkinyl having up to 10 carbon atoms in each case, wherein the substituents on the alkyl, alkenyl and alkinyl are selected from the group consisting of fluorine; chlorine; cyano; alkoximinon having 1 to 4 carbon atoms in the alkyl part; unsubstituted cycloalkyl having 3 to 6 carbon atoms; cycloalkyl having 3 to 6 carbon atoms which is substituted by C$_1$-C$_4$-alkyl; unsubstituted phenyl; phenyl which is mono- or trisubstituted, identically or differently by fluorine, chlorine, bromine, iodine, nitro, trifluoromethyl, C$_1$-C$_2$-alkyl, C$_1$-C$_2$-alkoxy, C$_1$-C$_2$-alkylthio, C$_1$-C$_2$-alkylsulphinyl or C$_1$-C$_4$-alkylsulphonyl; a radical —D—R$^9$, a radical

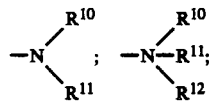

—CO—OR$^{13}$; —CO—NR$^{14}$R$^{15}$; or —CS—NR$^{14}$R$^{15}$
R$^{10}$ represents hydrogen or alkyl having 1 to 4, carbon atoms,
R$^{11}$ represents alkyl having 1 to 4 carbon atoms,
R$^{12}$ represents alkyl having 1 to 4 carbon atoms,
R$^{13}$ represents alkyl having 1 to 4 carbon atoms,
R$^{14}$ and R$^{15}$, each independently represents hydrogen or alkyl having 1 to 6 carbon atoms or
R$^4$, furthermore, represents unsubstituted cycloalkyl having 3 to 7 ring carbon atoms or cycloalkyl having 3 to 7 ring carbon atoms which is mono- to tri-substituted, identically or differently, by fluorine, chlorine or C$_1$-C$_4$-alkyl, C$_1$-C$_4$-alkoxy, C$_2$-C$_4$-alkenyl or halo-C$_1$-C$_2$-alkyl where halo represents 1 to 3 fluorine or chlorine atoms; unsubstituted phenyl or phenyl which is mono- to tri-, identically or differently substituted by fluorine, chlorine, bromine, C$_1$-C$_4$-alkyl, trifluoromethyl; or a radical

—D$^1$—R$^{17}$, where
D$^1$ represents oxygen, sulphur, sulphinyl or sulphonyl,
R$^{17}$ represents hydrogen or C$_1$-C$_4$-alkyl,
R$^4$, furthermore, represents an unsubstituted or substituted 5- or 6-membered heterocycle which can contain 1 to 2 identical or different heteroatoms selected from oxygen, nitrogen or sulphur said heterocycles being pyrrolidine, piperidine, morpholine, furan and thiazole and if substituted said heterocycle is mono- or tri-substituted, identically or differently, by fluorine; chlorine; bromine; iodine; C$_1$-C$_2$-alkyl; halo-C$_1$-C$_2$-alkyl where halo represents fluorine or chlorine, amino, alkylamino or dialkylamino having 1 to 2 carbon atoms in each individual alkyl moiety, by nitro, cyano, or a C$_1$-C$_4$-alkoxy radical, C$_1$-C$_4$-alkylthio radical or C$_1$-C$_4$-alkyl-sulphonyl radical.

3. A pyrimidyl-oxy- and -thio-benzoic acid derivative according to claim 1, in which R$^1$, R$^2$ and R$^3$, each independently represent hydrogen; alkyl having 1 to 4 carbon atoms; unsubstituted C$_1$-C$_4$-alkoxy or C$_1$-C$_4$-alkoxy which is substituted by C$_2$-C$_4$-alkenyl or C$_1$-C$_2$-alkoxy; alkylamino, dialkylamino having 1 to 4 carbon atoms in each of the individual alkyl moieties; amino; alkenyl-amino or dialkenylamino having 3 to 4 carbon atoms in each of the individual alkenyl moieties; alkenyl having 2 to 6 carbon atoms; trifluoromethyl, or R$^1$ and R$^2$ or R$^3$ together represent a saturated or unsaturated or 6-membered carbocyclic ring, with the proviso that at least one of the radicals R$^1$, R$^2$ or R$^3$ represents alkyl having 1 to 4 carbon atoms, trifluoromethyl or forms a part of the fused 5- or 6-membered carboxycyclic ring,
Z represents a nitrogen atom,
X represents oxygen or sulphur,
Y represents fluorine; chlorine; bromine; iodine; nitro; amino; alkyl, alkoxy, haloalkyl, alkylcarbonylamino, alkoxycarbonylamino having, in each case, 1 to 3 carbon atoms in the alkyl moiety and, in the case of haloalkyl, having 1 to 3 halo atoms where halo represents fluorine, chlorine, bromine and iodine; or phenoxycarbonylamino, where the Y's can be identical or different,
n represents an integer 0, 1, 2 or 3,
A represents oxygen or sulphur,
B represents oxygen, sulphur or a radical —N—R$^7$,
where
R$^7$ represents hydrogen, unsubstituted alkyl having 1 to 4 carbon atoms or alkyl, having 1 to 4 carbon atoms which is mono- to tri-substituted, identically or differently, by fluorine, chlorine, bromine, iodine, cyano or alkenyl having 2 to 4 carbon atoms,
R$^4$ represents unsubstituted alkyl having 4 to 10 carbon atoms, or alkenyl or alkinyl having up to 10 carbon atoms or mono- to penta-, identically or differently, substituted alkyl having 4 to 10 carbon atoms, alkenyl or alkinyl having up to 10 carbon atoms wherein the substituents on the alkyl, alkenyl or alkinyl are selected from the group consisting of fluorine; chlorine; cyano; alkoximino having 1 to 4 carbon atoms in the alkyl moiety; unsubstituted cycloalkyl having 3 to 6 carbon atoms or cycloalkyl having 3 to 6 carbon atoms which is substituted by C$_1$-C$_4$-alkyl; unsubstituted phenyl or phenyl which is substituted by fluorine, chlorine, bromine, iodine, nitro, trifluoromethyl, C$_1$-C$_2$-alkyl, C$_1$-C$_2$-alkoxy, C$_1$-C$_2$-alkylthio, C$_1$-C$_2$-alkylsulphinyl or C$_1$-C$_4$-alkylsulphonyl; a radical —D—R$^9$; a radical

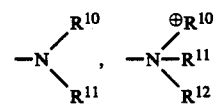

—CO—OR$^{13}$, —CO—NR$^{14}$R$^{15}$ or —CS—NR$^{14}$R$^{15}$, where
D represents oxygen, sulphur or sulphonyl and $R^9$ represents hydrogen; alkyl having 1 to 4 carbon atoms; alkenyl having 3 to 4 carbon atoms; unsubstituted phenyl, benzyl or phenethyl or phenyl, benzyl or phenethyl which are mono- to tri identically or differently substituted on the phenyl by fluorine, chlorine, bromine, $C_1$–$C_2$-alkyl or $C_1$–$C_2$-alkoxy, $R^{10}$ represents hydrogen or alkyl having 1 to 4 carbon atoms, $R^{11}$ represents alkyl having 1 to 4 carbon atoms, or $R^4$, furthermore, represents unsubstituted cycloalkyl having 3 to 6 carbon atoms or cycloalkyl having 3 to 6 carbon atoms which is mono- to tri-substituted, identically or differently, by fluorine, chlorine or $C_1$–$C_4$-alkyl, $C_1$–$C_4$-alkoxy, $C_2$–$C_4$-alkenyl or halo —$C_1$–$C_2$-alkyl where halo represents 1 to 3 fluorine or chlorine atoms; unsubstituted phenyl, benzyl or phenethyl or phenyl, benzyl or phenethyl which is mono- to tri-, identically or differently substituted on the phenyl by fluorine, chlorine bromine, $C_1$–$C_4$-alkyl or trifluoromethyl; or a radical —$D^1$—$R^{17}$, where $D^1$ represents oxygen, $R^{17}$ represents hydrogen or $C_1$–$C_4$-alkyl, $R^4$, furthermore, represents an unsubstituted or substituted 5- to 6-membered heterocycle which can contain 1 to 2 identical or different heteroatoms selected from oxygen, nitrogen or sulphur said heterocycles being pyrrolidine, piperidine, morpholine, furan and thiazole and if substituted the heterocycle is mono- to tri-substituted, identically or differently, by, fluorine; chlorine, bromine; iodine, $C_1$–$C_2$-alkyl, halo-$C_1$–$C_4$-alkyl, where halo represents 1 to 3 identical or different fluorine or chlorine atoms, amino; alkylamino or dialkylamino having 1 to 2 carbon atoms in each of the individual alkyl moieties; nitro; cyano; $C_1$–$C_4$-alkoxy; $C_1$–$C_4$-alkylthio or $C_1$–$C_4$-alkylsulphonyl.

4. A pyrimidyl-oxy- and -thiobenzoic acid derivative, according to claim 1, in which $R^1$, $R^2$ and $R^3$, independently of one another, in each case represent hydrogen; alkyl having 1 to 4 carbon atoms; unsubstituted $C_1$–$C_4$-alkoxy or $C_1$–$C_4$-alkoxy which is substituted by $C_2$–$C_4$-alkenyl or $C_1$–$C_2$-alkoxy; alkylamino, dialkylamino having 1 to 4 carbon atoms in each of the individual alkyl moieties; amino; alkenylamino or dialkenylamino having 3 to 4 carbon atoms in each of the individual alkenyl moieties; alkenyl having 2 to 6 carbon atoms or trifluoromethyl or $R^1$ and $R^2$ or $R^2$ and $R^3$ together represent a saturated or unsaturated 5- or 6-membered carbocyclic ring, with the proviso that at least one of the radicals $R^1$, $R^2$ or $R^3$ represent alkyl having 1 to 4 carbon atoms, trifluoromethyl or a part of the fused 5- or 6-membered carbocyclic ring, Z represents a nitrogen atom, X represents oxygen or sulphur, Y represents fluorine; chlorine; bromine; iodine; nitro; amino; alkyl, alkoxy, haloalkyl alkylcarbonylamino, alkoxycarbonylamino having 1 to 3 carbon atoms in the alkyl moieties in each case and, in the case of haloalkyl, having 1 to 3 halo atoms where halo represents fluorine, chlorine, bromine, or iodine; or phenoxycarbonylamino, where Y can be identical or different n represents an integer 0, 1, 2 or 3, A represents a radical $R^5$—N= or a radical $R^6$O—N=, where $R^5$ represents hydrogen; alkyl or hydroxyalkyl having 1 to 4 carbon atoms in each case or alkenyl having 3 to 4 carbon atoms, $R^6$ represents hydrogen or alkyl having 1 to 4 carbon atoms, B represents oxygen, sulphur or a radical

where $R^7$ represents hydrogen, unsubstituted alkyl having 1 to 4 carbon atoms or alkyl having 1 to 4 carbon atoms which is mono- to tri-substituted, identically or differently, by fluorine, chlorine, bromine, iodine or cyano; or alkenyl having 2 to 4 carbon atoms, $R^4$ represents unsubstituted alkyl having 4 to 10 carbon atoms or alkenyl or alkinyl having up to 10 carbon atoms or mono- to penta-, identically or differently, substituted alkyl having 4 to 10 carbon atoms, or alkenyl or alkinyl having up to 10 carbon atoms in each case, wherein the alkyl, alkenyl and alkinyl substituents are selected from the group consisting of fluorine; chlorine; cyano; alkoximino having 1 to 4 carbon atoms in the alkyl moiety; unsubstituted cycloalkyl having 3 to 6 carbon atoms or cycloalkyl having 3 to 6 carbon atoms which is mono- to tri-substituted, identically or differently, by $C_1$–$C_4$-alkyl, unsubstituted phenyl or phenyl which is mono- to tri-substituted, identically or differently, by fluorine, chlorine, bromine, iodine, nitro, trifluoromethyl, $C_1$–$C_2$-alkyl, $C_1$–$C_2$-alkoxy, $C_1$–$C_2$-alkylthio, $C_1$–$C_2$-alkyl-sulphinyl or $C_1$–$C_4$-alkyl-sulphonyl; or a radical —D—$R^9$, where D represents oxygen, sulphur or sulphonyl and $R^9$ represents hydrogen, alkyl having 1 to 4 carbon atoms, alkenyl having 3 to 4 carbon atoms, unsubstituted phenyl, benzyl or phenethyl or phenyl, benzyl or phenothyl which are mono- to tri-, identically or differently, substituted on the phenyl by fluorine, $R^4$, furthermore, represents unsubstituted cycloalkyl having 3 to 6 carbon atoms or cycloalkyl having 3 to 6 carbon atoms which is mono- to tri-substituted, identically or differently, by fluorine, chlorine or $C_1$–$C_4$-alkyl; unsubstituted phenyl or mono- to tri-, identically or differently, substituted phenyl, where the phenyl substituents are fluorine, chlorine, bromine, $C_1$–$C_4$-alkyl, or trifluoromethyl, or a radical —$O^1$—$R^{17}$, where $D^1$ represents oxygen, $R^{17}$ represents hydrogen or $C_1$–$C_4$-alkyl, $R^4$, furthermore, represents a 5- or 6-membered heterocycle which can contain 1 to 2 identical or different heteroatoms selected from oxygen, nitrogen or sulphur said heterocycles being pyrrolidine, piperidine, morpholine, furan and thiazole and which is optionally mono to tri-substituted, identically or differently, by fluorine, chlorine, bromine, iodine, $C_1$–$C_2$-alkyl, halo-$C_1$–$C_2$-alkyl where halo represents 1 to 3 identical or different fluorine or chlorine atoms, by amino; alkylamino or dialkylamino having 1 to 2 carbon atoms in each of the individual alkyl moieties; by nitro, cyano, $C_1$–$C_4$-alkoxy, $C_1$–$C_4$-alkylthio or $C_1$–$C_4$-alkylsulphonyl.

5. A pyrimidyl-oxy- or -thio-benzoic acid derivative according to claim 1, selected from
N-(1,1-dimethyl-propyl)-4-(4,6-dimethyl-pyrimidyl-2-mercapto)-benzamide,
N-tert.butyl-4-(4,5-dimethyl-pyrimidyl-2-mercapto)-benzamide,
N-tert.butyl-4-(4-methyl-5-ethyl-pyrimidyl-2-mercapto)-benzamide,
N-tert.butyl-4-(4,6-dimethyl-pyrimidyl-2-mercapto)-benzamide, and
tert.butyl-4(4,5,6-trimethyl-pyrimidyl-2-mercapto)benzoate.

6. A herbicidal composition comprising a herbicidally effective amount of at least one pyrimidyl-oxy- or -thio-benzoic acid derivative according to claim 1, and an agriculturally acceptable extender or carrier therefor.

7. A plant growth regulating composition comprising a plant growth regulating effective amount of at least one pyrimidyl-oxy- or -thio-benzoic acid derivative according to claim 1, and an agriculturally acceptable extender or carrier therefor.

8. A method for combating weeds comprising applying to said weeds or their habitat a herbicidally effective amount of pyrimidyl-oxy- or -thio-benzoic acid derivative according to claim 1.

9. A method for a controlling plant growth comprising applying to said plant or a habitat thereof a plant growth regulatory effective amount of a pyrimidyl-oxy- or -thio-benzoic acid according to claim 1.

* * * * *